United States Patent
Li et al.

(10) Patent No.: US 7,915,390 B2
(45) Date of Patent: Mar. 29, 2011

(54) ANTI-NOTCH3 AGONIST ANTIBODIES AND THEIR USE IN THE TREATMENT OF NOTCH3-RELATED DISEASES

(75) Inventors: Kang Li, San Diego, CA (US); Bin-Bing Stephen Zhou, Houston, TX (US); Wenjuan Wu, Carmel, IN (US); Sek Chung Fung, Houston, TX (US); Sanjaya Singh, Sandy Hook, CT (US)

(73) Assignee: Genentech, Inc., South San Francisco, CA (US)

( * ) Notice: Subject to any disclaimer, the term of this patent is extended or adjusted under 35 U.S.C. 154(b) by 183 days.

(21) Appl. No.: 11/874,682

(22) Filed: Oct. 18, 2007

(65) Prior Publication Data

US 2010/0111971 A9 May 6, 2010

Related U.S. Application Data

(60) Provisional application No. 60/852,861, filed on Oct. 19, 2006, provisional application No. 60/879,218, filed on Jan. 6, 2007, provisional application No. 60/875,597, filed on Dec. 18, 2006.

(51) Int. Cl.
*C12P 21/08* (2006.01)
*C07K 16/18* (2006.01)
*C07K 14/00* (2006.01)

(52) U.S. Cl. ............. 530/388.22; 530/387.1; 530/387.3; 530/387.7; 530/387.9; 530/388.8; 530/391.3; 530/350

(58) Field of Classification Search .................. 530/350, 530/387.1, 387.3, 387.9, 388.1, 388.22, 387.7, 530/388.8, 391.3
See application file for complete search history.

(56) References Cited

U.S. PATENT DOCUMENTS

| | | | |
|---|---|---|---|
| 5,648,464 | A | 7/1997 | Artavanis-Tsakonas et al. |
| 5,780,300 | A | 7/1998 | Artavanis-Tsakonas et al. |
| 5,786,158 | A | 7/1998 | Artavanis-Tsakonas et al. |
| 5,789,195 | A | 8/1998 | Artavanis-Tsakonas et al. |
| 6,083,904 | A | 7/2000 | Artavanis-Tsakonas et al. |
| 6,090,922 | A | 7/2000 | Artavanis-Tsakonas et al. |
| 6,149,902 | A | 11/2000 | Artavanis-Tsakonas et al. |
| 6,436,650 | B1 | 8/2002 | Artavanis-Tsakonas et al. |
| 6,692,919 | B1 | 2/2004 | Artavanis-Tsakonas et al. |
| 2002/0151487 | A1 | 10/2002 | Nickoloff et al. |
| 2003/0186290 | A1 | 10/2003 | Tournier-Lasserve et al. |
| 2004/0058443 | A1 | 3/2004 | Artavanis-Tsakonas et al. |
| 2004/0242482 | A1 | 12/2004 | Gehring et al. |
| 2005/0112121 | A1 | 5/2005 | Artavanis-Tsakonas et al. |
| 2005/0158859 | A1 | 7/2005 | Artavanis-Tsakonas et al. |
| 2005/0208027 | A1 | 9/2005 | Conboy et al. |
| 2006/0002924 | A1 | 1/2006 | Bodmer et al. |
| 2007/0003983 | A1 | 1/2007 | Artavanis-Tsakonas et al. |
| 2008/0107648 | A1 | 5/2008 | Noguera et al. |
| 2008/0131908 | A1 | 6/2008 | Li et al. |
| 2008/0226621 | A1 | 9/2008 | Fung et al. |

FOREIGN PATENT DOCUMENTS

| | | |
|---|---|---|
| FR | 2 777 285 A1 | 10/1999 |
| WO | 95/15982 | 6/1995 |
| WO | 00/20576 | 4/2000 |
| WO | 2006/068822 A1 | 6/2000 |
| WO | 02/24221 A2 | 3/2002 |
| WO | 2006/015375 A2 | 2/2006 |
| WO | 2006/017173 A1 | 2/2006 |
| WO | 2006/053063 A2 | 5/2006 |
| WO | 2008/057144 A2 | 5/2008 |
| WO | 2008/150525 A1 | 12/2008 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Rudikoff et al. (Proc. Natl. Acad. Sci. USA. 1982; 79 (6): 1979-1983).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Winkler et al. (J. Immunol. Oct. 15, 2000; 165 (8): 4505-4514).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Stancoviski et al. (Proceedings of the National Academy of Science USA. 1991; 88: 8691-8695).*
Xu et al. (Int. J. Cancer. 1993; 53: 401-408).*
Jiang et al. (J. Biol. Chem. Feb. 11, 2005; 280 (6): 4656-4662).*
Riemer et al. (Mol. Immunol. 2005; 42: 1121-1124).*
Greenspan et al. (Nature Biotechnology. 1999; 7: 936-937).*
George et al. (Circulation. 1998; 97: 900-906).*
Bellavia et al. (Oncogene. Sep. 1, 2008; 27 (38): 5092-8).*
Joutel et al., "Skin biopsy immunostaining with a Notch3 monoclonal antibody for CADASIL diagnosis" *Lancet* 358:2049-2051 (2001).
Jurynczyk et al., "Notch3 Inhibition in Myelin-Reactive T Cells Down-Regulates Protein Kinase Cθ and Attenuates Experimental Autoimmune Encephalomyelitis" *Journal of Immunology* 180(4):2634-2640 (2008).
Li et al., "Modulation of Notch Signaling by Antibodies Specific for the Extracellular Negative Regulatory Region of NOTCH3" *Journal of Biological Chemistry* 283(12):8046-8054 (Mar. 21, 2008).
Allenspach et al., "Notch signaling in cancer" *Cancer Biol Ther.* 1(5):466-76 (2002).

(Continued)

*Primary Examiner* — Stephen L Rawlings
(74) *Attorney, Agent, or Firm* — Danielle M. Pasqualone

(57) ABSTRACT

The present invention relates to agonist antibodies that specifically bind to Notch 3 and activate signaling. The present invention includes antibodies binding to an epitope comprising the first Lin12 domain. The present invention also includes uses of these antibodies to treat or prevent Notch 3 related diseases or disorders.

19 Claims, 18 Drawing Sheets

OTHER PUBLICATIONS

Anastasi et al., "Expression of activated Notch3 in transgenic mice enhances generation of T regulatory cells and protects against experimental autoimmune diabetes" *J Immunol.* 171(9):4504-11 (Nov. 2003).

Androutsellis-Theotokis et al., "Notch signalling regulates stem cell numbers in n vitro and in vivo" *Nature* 442:823-6 (Aug. 2006).

Artavanis-Tsakonas et al., "Notch Signaling" *Science* 268:225-232 (Apr. 14, 1995).

Artavanis-Tsakonas et al., "Notch Signaling: Cell Fate Control and Signal Integration in Development" *Science* 284:770-776 (1999).

Aster et al., "The folding and structural integrity of the first LIN-12 module of human Notch1 are calcium-dependent" *Biochemistry* 38(15):4736-42 (Apr. 1999).

Bellavia et al., "Combined expression of pTalpha and Notch3 in T cell leukemia identifies the requirement of preTCR for leukemogenesis" *Proc Natl Acad Sci U S A.* 99(5):3788-93 (Mar. 2002).

Bocchetta et al., "Notch-1 induction, a novel activity of SV40 required for growth of SV40-transformed human mesothelial cells" *Oncogene* 22(1):81-9 (Jan. 2003).

Bolos et al., "Notch signaling in development and cancer" *Endocr Rev.* 28(3):339-63 (May 2007).

Bray, "Notch signalling: a simple pathway becomes complex" *Nat Rev Mol Cell Biol.* 7(9):678-89 (Sep. 2006).

Buchler et al., "The Notch signaling pathway is related to neurovascular progression of pancreatic cancer" *Ann Surg.* 242(6):791-800 (Dec. 2005).

Chiba, "Notch signaling in stem cell systems" *Stem Cells* 24(11):2437-47 (Nov. 2006).

Coffman et al., "Expression of an extracellular deletion of Xotch diverts cell fate in Xenopus embryos" *Cell* 73(4):659-71 (May 1993).

Davies et al., "Affinity improvement of single antibody VH domains: residues in all three hypervariable regions affect antigen binding" *Immunotechnology* 2:169-179 (1996).

Domenga et al., "Notch3 is required for arterial identity and maturation of vascular smooth muscle cells" *Genes Dev.* 18(22):2730-5 (Nov. 2004).

Ellisen et al., "TAN-1, the human homolog of the *Drosophila* notch gene, is broken by chromosomal translocations in T lymphoblastic neoplasms" *Cell* 66(4):649-61 (Aug. 1991).

Fan et al., "Notch pathway inhibition depletes stem-like cells and blocks engraftment in embryonal brain tumors" *Cancer Research* 66(15):7445-52 (Aug. 2006).

Flynn et al., "The role of Notch receptor expression in bile duct development and disease" *J Pathol.* 204(1):55-64 (Sep. 2004).

Fre et al., "Notch signals control the fate of immature progenitor cells in the intestine" *Nature* 435:964-8 (Jun. 2005).

Gordon et al., "Structural basis for autoinhibition of Notch" *Nat Struct Mol Biol.* 14(4):295-300 (Apr. 2007).

Haruki et al., "Dominant-negative Notch3 receptor inhibits mitogen-activated protein kinase pathway and the growth of human lung cancers" *Cancer Research* 65(9):3555-61 (May 2005).

Hedvat et al., "Insights into extramedullary tumour cell growth revealed by expression profiling of human plasmacytomas and multiple myeloma" *Br J Haematol.* 122(5):728-44 (Sep. 2003).

Heller et al., "Amino Acids at the Site of V.-J. Recombination Not Encoded by Germline Sequences" *Journal of Experimental Medicine* 166:637-646 (1987).

Holt et al., "Domain antibodies: proteins for therapy" *Trends Biotechnol.* 21(11):484-490 (Nov. 2003).

Houde et al., "Overexpression of the NOTCH ligand JAG2 in malignant plasma cells from multiple myeloma patients and cell lines" *Blood* 104(12):3697-704 (Dec. 2004).

Hu et al., "Overexpression of activated murine Notch1 and Notch3 in transgenic mice blocks mammary gland development and induces mammary tumors" *Am J Pathol.* 168(3):973-90 (Mar. 2006).

Jang et al., "Notch signaling as a target in multimodality cancer therapy" *Curr Opin Mol Ther.* 2(1):55-65 (Feb. 2000).

Joutel et al., "Notch signalling pathway and human diseases" *Semin Cell Dev Biol.* 9(6):619-25 (Dec. 1998).

Joutel et al., "Notch3 mutations in CADASIL, a hereditary adult-onset condition causing stroke and dementia" *Nature* 383:707-10 (Oct. 1996).

Jundt et al., "Jagged1-induced Notch signaling drives proliferation of multiple myeloma Cells" *Blood* 103(9):3511-5 (May 2004).

Kadesch, "Notch signaling: a dance of proteins changing partners" *Exp Cell Res.* 260(1):1-8 (Oct. 2000).

Kidd et al., "Sequence of the notch locus of *Drosophila melanogaster*: relationship of the encoded protein to mammalian clotting and growth factors" *Mol Cell Biol.* 6(9):3094-108 (Sep. 1986).

Kopczynski et al., "Delta, a *Drosophila* neurogenic gene, is transcriptionally complex and encodes a protein related to blood coagulation factors and epidermal growth factor of vertebrates" *Genes Dev.* 2:1723-35 (1988).

Leong et al., "Recent insights into the role of Notch signalingin tumorigenesis" *Blood* 107(6):2223-33 (Mar. 2006).

Lu et al., "Selection of potential markers for epithelial ovarian cancer with gene expression arrays and recursive descent partition analysis" *Clin Cancer Res.* 10(10):3291-300. (May 2004).

Mailhos et al., "Delta4, an Endothelial Specific Notch Ligand Expressed at Sites of Physiological and Tumor Angiogenesis" *Differentiation* 69:135-144 (2001).

Malecki et al., "Leukemia-associated mutations within the NOTCH1 heterodimerization domain fall into at least two distinct mechanistic classes" *Mol Cell Biol.* 26(12):4642-51 (Jun. 2006).

Nam et al., "Notch signaling as a therapeutic target" *Curr Opin Chem Biol.* 6(4):501-9 (Aug. 2002).

Park et al., "Notch3 gene amplification in ovarian cancer" *Cancer Research* 66(12):6312-8 (Jun. 2006).

Rao et al., "K Chain Variable Regions from Three Galactan Binding Myeloma Proteins" *Biochemistry* 17(25):5555-5559 (1978).

Reya et al., "Stem cells, cancer, and cancer stem cells" *Nature* 414:105-11 (2001).

Rudikoff et al., "K chain joining segments and structural diversity of antibody combining sites" *Proc. Natl. Acad. Sci. USA* 77(7):4270-4274 (1980).

Sanchez-Irizarry et al., "Notch subunit heterodimerization and prevention of ligand-independent proteolytic activation depend, respectively, on a novel domain and the LNR repeats" *Mol Cell Biol.* 24(21):9265-73 (2004).

Screpanti et al., "Notch, a unifying target in T-cell acute lymphoblastic leukemia?" *Trends Mol Med.* 9(1):30-5 (Jan. 2003).

Shimizu et al., "Physical interaction of Delta1, Jagged1, and Jagged2 with Notch1 and Notch3 receptors" *Biochem Biophys Res Commun.* 276(1):385-9 (Sep. 2000).

Sullivan and Bicknell, "New molecular pathways in angiogenesis" *British Journal of Cancer* 89(2):228-231 (Jul. 21, 2003).

Sweeney et al., "Notch 1 and 3 receptor signaling modulates vascular smooth muscle cell growth, apoptosis, and migration via a CBF-1/RBP-Jk dependent pathway" *FASEB J.* 18(12):1421-3 (Sep. 2004).

Swiatek et al., "Notch1 is essential for postimplantation development in mice" *Genes Dev.* 8(6):707-19 (Mar. 1994).

Taichman et al., "Notch1 and Jagged1 expression by the developing pulmonary vasculature" *Dev Dyn.* 225(2):166-75 (Oct. 2002).

Thelu et al., "Notch signalling is linked to epidermal cell differentiation level in basal cell carcinoma, psoriasis and wound healing" *BMC Dermatol.* 2:7 (Apr. 2002).

Vacca et al., "Notch3 and pre-TCR interaction unveils distinct NF-kappaB pathways in T-cell development and leukemia" *EMBO Journal* 25(5):1000-8 (Mar. 2006).

van Es et al., "Notch/gamma-secretase inhibition turns proliferative cells in intestinal crypts and adenomas into goblet cells" *Nature* 435:959-63 (Jun. 2005).

van Limpt et al., "Phox2B mutations and the Delta-Notch pathway in neuroblastoma" *Cancer Lett.* 228:59-63 (Oct. 2005).

Vardar et al., "Nuclear magnetic resonance structure of a prototype Lin12-Notch repeat module from human Notch1" *Biochemistry* 42(23):7061-7 (Jun. 2003).

Von Boehmer, "Notch in lymphopoiesis and T cell polarization" *Nat Immunol.* 6(7):641-2 (Jul. 2005).

Weijzen et al., "Activation of Notch-1 signaling maintains the neoplastic phenotype in human Ras-transformed cells" *Nat Med.* 8(9):979-986 (Sep. 2002).

Weng et al., "Activating mutations of NOTCH1 in human T cell acute lymphoblastic leukemia" *Science* 306(5694):269-271 (Oct. 8, 2004).

Wharton et al., "Nucleotide sequence from the neurogenic locus notch implies a gene product that shares homology with proteins containing EGF-like repeats" *Cell* 43:567-81 (Dec. 1985).

Xu et al., "Regions of *Drosophila* Notch that contribute to ligand binding and the modulatory influence of Fringe" *J Biol Chem.* 280(34):30158-65 (Aug. 2005).

Yabe et al., "Immunohistological localization of Notch receptors and their ligands Delta and Jagged in synovial tissues of rheumatoid arthritis" *J Orthop Sci.* 10(6):589-94 (Nov. 2005).

Yochem et al., "The Caenorhabditis elegans lin-12 gene encodes a transmembrane protein with overall similarity to *Drosophila* Notch" *Nature* 335:547-50 (Oct. 1988).

Zeng et al., "Crosstalk between tumor and endothelial cells promotes tumor angiogenesis by MAPK activation of Notch signaling" *Cancer Cell* 8(1):13-23 (Jul. 2005).

Zweidler-McKay et al., "Notch signaling is a potent inducer of growth arrest and apoptosis in a wide range of B-cell malignancies" *Blood* 106(12):3898-906 (Dec. 2005).

* cited by examiner

FIGURE 1

Amino Acid Sequence of Human Notch 3 (NP_ 000426)

```
   1 MGPGARGRRR RRRPMSPPPP PPPVRALPLL LLLAGPGAAA PPCLDGSPCA NGGRCTQLPS
  61 REAACLCPPG WVGERCQLED PCHSGPCAGR GVCQSSVVAG TARFSCRCPR GFRGPDCSLP
 121 DPCLSSPCAH GARCSVGPDG RFLCSCPPGY QGRSCRSDVD ECRVGEPCRH GGTCLNTPGS
 181 FRCQCPAGYT GPLCENPAVP CAPSPCRNGG TCRQSGDLTY DCACLPGFEG QNCEVNVDDC
 241 PGHRCLNGGT CVDGVNTYNC QCPPEWTGQF CTEDVDECQL QPNACHNGGT CFNTLGGHSC
 301 VCVNGWTGES CSQNIDDCAT AVCFHGATCH DRVASFYCAC PMGKTGLLCH LDDACVSNPC
 361 HEDAICDTNP VNGRAICTCP PGFTGGACDQ DVDECSIGAN PCEHLGRCVN TQGSFLCQCG
 421 RGYTGPRCET DVNECLSGPC RNQATCLDRI GQFTCICMAG FTGTYCEVDI DECQSSPCVN
 481 GGVCKDRVNG FSCTCPSGFS GSTCQLDVDE CASTPCRNGA KCVDQPDGYE CRCAEGFEGT
 541 LCDRNVDDCS PDPCHHGRCV DGIASFSCAC APGYTGTRCE SQVDECRSQP CRHGGKCLDL
 601 VDKYLCRCPS GTTGVNCEVN IDDCASNPCT FGVCRDGINR YDCVCQPGFT GPLCNVEINE
 661 CASSPCGEGG SCVDGENGFR CLCPPGSLPP LCLPPSHPCA HEPCSHGICY DAPGGFRCVC
 721 EPGWSGPRCS QSLARDACES QPCRAGGTCS SDGMGFHCTC PPGVQGRQCE LLSPCTPNPC
 781 EHGGRCESAP GQLPVCSCPQ GWQGPRCQQD VDECAGPAPC GPHGICTNLA GSFSCTCHGG
 841 YTGPSCDQDI NDCDPNPCLN GGSCQDGVGS FSCSCLPGFA GPRCARDVDE CLSNPCGPGT
 901 CTDHVASFTC TCPPGYGGFH CEQDLPDCSP SSCFNGGTCV DGVNSFSCLC RPGYTGAHCQ
 961 HEADPCLSRP CLHGGVCSAA HPGFRCTCLE SFTGPQCQTL VDWCSRQPCQ NGGRCVQTGA
1021 YCLCPPGWSG RLCDIRSLPC REAAAQIGVR LEQLCQAGGQ CVDEDSSHYC VCPEGRTGSH
1081 CEQEVDPCLA QPCQHGGTCR GYMGGYMCEC LPGYNGDNCE DDVDECASQP CQHGGSCIDL
1141 VARYLCSCPP GTLGVLCEIN EDDCGPGPPL DSGPRCLHNG TCVDLVGGFR CTCPPGYTGL
1201 RCEADINECR SGACHAAHTR DCLQDPGGGF RCLCHAGFSG PRCQTVLSPC ESQPCQHGGQ
1261 CRPSPGPGGG LTFTCHCAQP FWGPRCERVA RSCRELQCPV GVPCQQTPRG PRCACPPGLS
1321 GPSCRSFPGS PPGASNASCA AAPCLHGGSC RPAPLAPFFR CACAQGWTGP RCEAPAAAPE
1381 VSEEPRCPRA ACQAKRGDQR CDRECNSPGC GWDGGDCSLS VGDPWRQCEA LQCWRLFNNS
1441 RCDPACSSPA CLYDNFDCHA GGRERTCNPV YEKYCADHFA DGRCDQGCNT EECGWDGLDC
1501 ASEVPALLAR GVLVLTVLLP PEELLRSSAD FLQRLSAILR TSLRFRLDAH GQAMVFPYHR
1561 PSPGSEPRAR RELAPEVIGS VVMLEIDNRL CLQSPENDHC FPDAQSAADY LGALSAVERL
1621 DFPYPLRDVR GEPLEPPEPS VPLLPLLVAG AVLLLVILVL GVMVARRKRE HSTLWFPEGF
1681 SLHKDVASGH KGRREPVGQD ALGMKNMAKG ESLMGEVATD WMDTECPEAK RLKVEEPGMG
1741 AEEAVDCRQW TQHHLVAADI RVAPAMALTP PQGDADADGM DVNVRGPDGF TPLMLASFCG
1801 GALEPMPTEE DEADDTSASI ISDLICQGAQ LGARTDRTGE TALHLAARYA RADAAKRLLD
1861 AGADTNAQDH SGRTPLHTAV TADAQGVFQI LIRNRSTDLD ARMADGSTAL ILAARLAVEG
1921 MVEELIASHA DVNAVDELGK SALHWAAAVN NVEATLALLK NGANKDMQDS KEETPLFLAA
1981 REGSYEAAKL LLDHFANREI TDHLDRLPRD VAQERLHQDI VRLLDQPSGP RSPPGPHGLG
2041 PLLCPPGAFL PGLKAAQSGS KKSRRPPGKA GLGPQGPRGR GKKLTLACPG PLADSSVTLS
2101 PVDSLDSPRP FGGPPASPGG FPLEGPYAAA TATAVSLAQL GGPGRAGLGR QPPGGCVLSL
2161 GLLNPVAVPL DWARLPPPAP PGPSFLLPLA PGPQLLNPGT PVSPQERPPP YLAVPGHGEE
2221 YPVAGAHSSP PKARFLRVPS EHPYLTPSPE SPEHWASPSP PSLSDWSEST PSPATATGAM
2281 ATTTGALPAQ PLPLSVPSSL AQAQTQLGPQ PEVTPKRQVL A   (SEQ ID NO 1)
```

FIGURE 2A  Amino acid sequence Comparison of Notch1, 2, 3 and 4.

```
1     - - - - - - - - - - - - - - - M P P L A P L I C L     Notch1.pro
1     - - - - - - - - - - - - M P A L R P A L L W A L I A L   Notch2.pro
1     M G P G A R G R R R R R P M S P P P P P P P V R A L P L L  Notch3.pro
1     - - - - - - - - - - - - - - M Q P P S L L L L I L L     Notch4.pro 12    A L L P A L A A R - - G P R C S Q P G E T C L N G G K C E A   Notch1.pro
16    W L C C A A P A H - - A L Q C R D G Y E P C V N E G M C V T   Notch2.pro
31    L L L A G P G A A - - A P P C L D G - S P C A N G G R C T Q   Notch3.pro
13    L L L C V S V V R P R G L L C G S F P E P C A N G G T C L S   Notch4.pro 40    A N - G T E A C V G G A F V G P R C Q D P N P C L - S T P   Notch1.pro
44    Y H N G T G Y C K C P E G F L G E Y C Q H R D P C E - K N R   Notch2.pro
58    L P S R E A A C L C P P G W V G E R C Q L E D P C H - S G P   Notch3.pro
43    L S L G Q G T C Q C A P G F L G E T C Q F P D P C Q N A Q L   Notch4.pro 68    C K N A G T C H V V D R R - - G V A D Y A - - - - - - - - C   Notch1.pro
73    C Q N G G T C V A Q A M L - - G K A T - - - - - - - - - - C   Notch2.pro
87    C A G R G V C Q S S V V A - - G T A R - - - - - - - - - - -   Notch3.pro
73    C Q N G G S C Q A L L P A P L G L P S S P S P L T P S F L C   Notch4.pro 88    S C A L G F S G P L C L T P L D N A C L T N - P C R N G G T   Notch1.pro
91    R C A S G F T G E D C Q Y S T S H P C F V S R P C L N G G T   Notch2.pro
104   - - - - - - - - - - - - - - - - - - - - - - - - - - - -   Notch3.pro
103   T C L P G F T G E R C Q A K L E D P C P P S - F C S K R G R   Notch4.pro 117   C D L I T L T E Y K C R C P P G W S G K S C Q Q A D P C A S   Notch1.pro
121   C H M L S R D T Y E C T C Q V G F T G K E C Q W T D A C L S   Notch2.pro
104   - - - - - - - - F S C R C P R G F R G P D C S L P D P C L S   Notch3.pro
132   C H I Q A S G R P Q C S C M P G W T G E Q C Q L R D F C S A   Notch4.pro 147   N P C A N G G Q C L P - F E A S Y I C H C P P S F H G F T C   Notch1.pro
151   H P C A N G S T C T T - V A N Q F S C K C L T G F T G Q K C   Notch2.pro
126   S P C A H G A R C S V G P D G R F L C S C P P G Y Q G R S C   Notch3.pro
162   N P C V N G G V C L A - T Y P Q I Q C H C P P G F E G H A C   Notch4.pro 176   R Q D V N E C G Q K P G L C R H G G T C H N E V G S Y R C V   Notch1.pro
180   E T D V N E C D - I P G H C Q H G G T C L N L P G S Y Q C Q   Notch2.pro
156   R S D V D E C R - V G E P C R H G G T C L N T P G S F R C Q   Notch3.pro
191   E R D V N E C F Q D P G P C P K G T S C H N T L G S F Q C L   Notch4.pro 206   C R A T H T G P N C E R P Y V P C S P S P C Q N G G T C R P   Notch1.pro
209   C P Q G F T G Q Y C D S L Y V P C A P S P C V N G G T C R Q   Notch2.pro
185   C P A G Y T G P L C E N P A V P C A P S P C R N G C T C R Q   Notch3.pro
221   C P V G Q E G P R C E L R A G P C P P R G C S N G G T C Q L   Notch4.pro 236   T G D - - - V T H E C A C L P G F T G Q N C E E N I D D C P   Notch1.pro
239   T G D - - - F T F E C N C L P G F E G S T C E R N I D D C P   Notch2.pro
215   S G D - - - L T Y D C A C L P G F E G Q N C E V N V D D C P   Notch3.pro
251   M P E K D S T F H L C L C P P G F I G P G C E V N P D N C V   Notch4.pro 263   G N C K N G G A C V D G V N T Y N C R C P P E W T G Q Y C   Notch1.pro
266   N H R C Q N G G V C V D G V N T Y N C R C P P Q W T G Q F C   Notch2.pro
242   G H R C L N G G T C V D G V N T Y N C Q C P P E W T G Q F C   Notch3.pro
281   S H Q C Q N G G T C Q D G L D T Y T C L C P E T W T G W D C   Notch4.pro 293   T E D V D E C Q L M - P N A C Q N G G T C H N T H G G Y N C   Notch1.pro
296   T E D V D E C L L Q - P N A C Q N G G T C A N R N G G Y G C   Notch2.pro
272   T E D V D E C Q L Q - P N A C H N G G T C F N L G G H S C   Notch3.pro
311   S E D V D E C E A Q G P P H C R N G G T C Q N S A G S F H C   Notch4.pro
```

FIGURE 2B

```
322  V C V N G W T G E D C S E N I D D C A S A A C F H G A T C H   Notch1.pro
325  V C V N G W S G D D C S E N I D D C A F A S C T P G S T C I   Notch2.pro
301  V C V N G W T G E S C S Q N I D D C A T A V C F H G A T C H   Notch3.pro
341  V C V S G W G G T S C E E N L D D C I A A T C A P G S T C I   Notch4.pro 352  D R V A S F Y C E C P E G R T G L L C H L N D A C I S N P C   Notch1.pro
355  D R V A S F S C M C P E G K A G L L C H L D D A C I S N P C   Notch2.pro
331  D R V A S F Y C A C P M G K T G L L C H L D D A C V S N P C   Notch3.pro
371  D R V G S F S C L C P P G R T G L L C H L E D M C L S Q P C   Notch4.pro 382  N E G S N C D T N P V N G K A I C T C P S G Y T G P A C S Q   Notch1.pro
385  H K G A L C D T N P L N G Q Y I C T C P Q G Y K G A D C T E   Notch2.pro
361  H E D A I C D T N P V N G R A I C T C P P G F T G G A C D Q   Notch3.pro
401  H G D A Q C S T N P L T G S T L C L C Q P G Y S G P T C H Q   Notch4.pro 412  D V D E C S L G - - - A N P C E H A G K C I N T L G S F E C   Notch1.pro
415  D V D E C A M A N - - S N P C E H A G K C V N T D G A F H C   Notch2.pro
391  D V D E C S I G - - - A N P C E H L G R C V N T Q G S F L C   Notch3.pro
431  D L D E C L M A Q Q G P S P C E H G G S C L N T P G S F N C   Notch4.pro 439  Q C L Q G Y T G P R C E I D V N E C V S N P C Q N D A T C L   Notch1.pro
443  E C L K G Y A G P R C E M D I N E C H S D P C Q N D A T C L   Notch2.pro
418  Q C G R G Y T G P R C E T D V N E C L S G P C R N Q A T C L   Notch3.pro
461  L C P P G Y T G S R C E A D E N E C L S Q P C H P G S T C L   Notch4.pro 469  D Q I G E F Q C I C M P G Y E G V H C E V N T D E C A S S P   Notch1.pro
473  D K I G G F T C L C M P G F K G V H C E L E I N E C Q S N P   Notch2.pro
448  D R T G Q F T C T C M A G F T G T Y C E V D I D E C Q S S P   Notch3.pro
491  D L L A T F H C L C P P G L E G Q L C E V E T N E C A S A P   Notch4.pro 499  C L H G R C L D K I N E F Q C E C P T G F T G H L C Q Y D     Notch1.pro
503  C V N N G Q C V D K V N R F Q C L C P P G F T G P V C Q I D   Notch2.pro
478  C V N G G V C K D R V N G F S C T C P S G F S G S T C Q L D   Notch3.pro
521  C L N H A D C H D L L N G F Q C I C L P G F S G T R C E E D   Notch4.pro 529  V D E C A S T P C K N G A K C L D C P N T Y T C V C T E G Y   Notch1.pro
533  I D D C S S T P C L N G A K C I D H P N G Y E C Q C A T G F   Notch2.pro
508  V D E C A S T P C R N G A K C V D Q P D G Y E C R C A E G F   Notch3.pro
551  I D E C R S S P C A N G G Q C Q D Q P - - - - - - - - - - -   Notch4.pro 559  T G T H C E V D I D E C D P D P C H Y G S C K D G V A T F T   Notch1.pro
563  T G V L C E E N I D N C D P D P C H H G Q C Q D G I D S Y T   Notch2.pro
538  E G T L C D R N V D D C S P D P C H H G R C V D G I A S F S   Notch3.pro
570  - - - - - - - - - - - - - - - - - - - - - - G A F H         Notch4.pro 589  C L C R P G Y T G H H C E T N I N E C S S Q P C R H G G T C   Notch1.pro
593  C T C N P G Y M G A I C S D Q I D F C Y S S P C L N D G R C   Notch2.pro
568  C A C A P G Y T G T R C E S Q V D E C R S Q P C R H G G K C   Notch3.pro
574  C K C L P G F E G P R C Q T E V D F C L S D P C P V G A S C   Notch4.pro 619  Q D R D N A Y L C F C L K G T T G P N C E I N L D D C A S S   Notch1.pro
623  I D L V N G Y Q C N C Q P G T S G V N C E I N F D D C A S N   Notch2.pro
598  L D L V D K Y L C R C P S G T T G V N C E V N I D D C A S N   Notch3.pro
604  L D L P G A F F C L C P S - - - - - - - - - - - - - - - - -   Notch4.pro 649  P C D S G T C L D K I D G Y E C A C E P G Y T G S M C N I N   Notch1.pro
653  P C I H G I C M D G I N R Y S C V C S P G F T G Q R C N I D   Notch2.pro
628  P C T F G V C R D G I N R Y D C V C Q P G F T G P L C N V E   Notch3.pro
617  - - - - - - - - - - - - - - - - - G F T G Q L C E V P       Notch4.pro
```

FIGURE 2C

```
679   I D E C A G N P C H N G G T C E D G I N G F T C R C P E G Y   Notch1.pro
683   I D E C A S N P C R K G A T C I N C V N G F R C I C P E G P   Notch2.pro
658   I N E C A S S P C G E G G S C V D G E N G F R C L C P P G S   Notch3.pro
627   L - - C A P N L C Q P K Q I C K D Q K D K A N C L C P D G -   Notch4.pro 709   H D P T C L S E V N E C N S N P C V H G A C R D S L N G Y K   Notch1.pro
713   H H P S C Y S Q V N E C L S N P C I H G N C T G G L S G Y K   Notch2.pro
688   L P P L C L P P S H P C A H E P C S H G I C Y D A P G G F R   Notch3.pro
654   - S P G C A P P E D N C T - - - C H H G H C Q R S S - - - -   Notch4.pro 739   C D C D P G W S G T N C - - D L N N E C E S N P C V N G G   Notch1.pro
743   C L C D A G W V G I N C - - E V D K N E C L S N P C Q N G G   Notch2.pro
718   C V C E P G W S G P R C S Q S L A R D A C E S Q P C R A G G   Notch3.pro
676   C V C D V G W T G P E C - - E A E L G G C I S A P C A H G G   Notch4.pro 767   T C K D M T S G Y V C T C R E G F S G P N C Q T N I N E C A   Notch1.pro
771   T C D N L V N G Y R C T C K K G F K G Y N C Q V N I D E C A   Notch2.pro
748   T C S S D G M G F H C T C P P G V Q G R C C E L - - - - - -   Notch3.pro
704   T C Y P Q P S G Y N C T C P T - - - - - - - - - - - - - -   Notch4.pro 797   S N P C L N Q G T C I D D V A G Y K C N C L P Y T G A T C   Notch1.pro
801   S N P C L N Q G T C F D D I S G Y T C H C V L P Y T G K N C   Notch2.pro
772   - - - - - - - - - - - - - - - - - - - - - - - - - - - -   Notch3.pro
719   - - - - - - - - - - - - - - - - - - - - - - - - - - - -   Notch4.pro 827   E V V L A P C A P S P C R N G G E C R Q S E D Y E S F S C V   Notch1.pro
831   Q T V L A P C S P N P C E N A A V C K E S P N F E S Y T C L   Notch2.pro
772   - - - L S P C T P N P C E H G G R C E S A P G - Q L P V C S   Notch3.pro
719   - - - - - - - - - - - - - - - - - - - - - - - - - - - -   Notch4.pro 857   C P T G W Q A G Q T C E V D I N E C V L - S P C R H G A S C   Notch1.pro
861   C A P G W Q G - Q R C T I D I D E C I S - K P C M N H G L C   Notch2.pro
798   C P Q G W Q G - P R C Q Q D V D E C A G P A P C G P H G I C   Notch3.pro
719   - - - - - - - - - - - - - - - - - - - - - - - - - - - -   Notch4.pro 886   Q N T H G G Y R C H C Q A G Y S G R N C E T D I D D C R P N   Notch1.pro
889   H N T Q G S Y M C E C P P G F S G M D C E E D I D D C L A N   Notch2.pro
827   T N L A G S F S C T C H G G Y T G P S C D Q D I N D C D P N   Notch3.pro
719   - - - - - - - - - - - - G Y T G P T C S E E M T A C H S G   Notch4.pro 916   P C H N G G S C T D G I N T A F C D C L P G F R G T F C E E   Notch1.pro
919   P C Q N G G S C M D G V N T F S C L C L P G F T G D K C Q T   Notch2.pro
857   P C L N G G S C Q D G V G S F S C S C L P G F A G P R C A R   Notch3.pro
736   P C L N G G S C N P S P G G Y Y C T C P P S H T G P Q C Q T   Notch4.pro 946   D I N E C A S D P C R N G A N C T D C V D S Y T C T C P A G   Notch1.pro
949   D M N E C L S E P C K N G G T C S D Y V N S Y T C K C Q A G   Notch2.pro
887   D V D E C L S N P C G P G - T C T D H V A S F T C T C P P G   Notch3.pro
766   S T D Y C V S A P C - - - - - - - - - - - - - - - - - -   Notch4.pro 976   F S G I H C E N N T P D C T E S S C F N G G T C V D G I N S   Notch1.pro
979   F D G V H C E N N I N E C T E S S C F N G G T C V D G I N S   Notch2.pro
916   Y G G F H C E Q D L P D C S P S S C F N G G T C V D G V N S   Notch3.pro
776   - - - - - - - - - - - - - - - - F N G G T C V N R P G T   Notch4.pro 1006  F T C L C P P G F T G S Y C Q H D V N - E C D S Q P C L H G   Notch1.pro
1009  F S C L C P V G F T G S F C L H E I N - E C S S H P C L N E   Notch2.pro
946   F S C L C R P G Y T G A H C Q H E A D - P C L S R P C L H G   Notch3.pro
788   F S C L C A M G F Q G P R C E G K L R P S C A D P C R N R   Notch4.pro
```

FIGURE 2D

```
1035  G T C Q D G C G S Y R C T C P Q G Y T G P N C Q N L V H W C   Notch1.pro
1038  G T C V D G L G T Y R C S C P L G Y T G K N C Q T L V N L C   Notch2.pro
975   G V C S A A H P G F R C T C L E S F T G P Q C Q T L V D W C   Notch3.pro
818   A T C Q D S P Q G P R C L C P T G Y T G G S C Q T L M D L C   Notch4.pro 1065  D S S P C K N G G K C W Q T H T Q Y R C E C P S G W T G L Y   Notch1.pro
1068  S R S P C K N K G T C V Q K K A E S Q C L C P S G W A G A Y   Notch2.pro
1005  S R Q P C Q N G G R C V Q T G - - A Y C L C P P G W S G R L   Notch3.pro
848   A Q K P C P R N S F C L Q T G P S F H C L C L Q G W T G P L   Notch4.pro 1095  C D V P S V S C E V A A Q R G V D V A R L C Q H G G L C V   Notch1.pro
1098  C D V P N V S C D I A A S R R G V L V E H L C Q H S G V C I   Notch2.pro
1033  C D I R S L P C R E A A Q I G V R L E Q L C Q A G G Q C V   Notch3.pro
878   C N L P L S S C Q K A A L S Q G I D V S S L C H N G G L C V   Notch4.pro 1125  D A G N T H H C R C Q A G Y T G S Y C E D L V D E C S P S P   Notch1.pro
1128  N A G N T H Y C Q C P L G Y T G S Y C E E Q L D E C A S N P   Notch2.pro
1063  D E D S S H Y C V C P E G R T G S H C E Q E V D P C L A Q P   Notch3.pro
908   D S G P S Y F C H C P P G F Q G S L C Q D H V N P C E S R P   Notch4.pro 1155  C Q N G A T C T D Y L G G Y S C K C V A G Y H G V N C S E E   Notch1.pro
1158  C Q H G A T C S D F I G G Y R C E C V P G Y Q G V N C E Y E   Notch2.pro
1093  C Q H G G T C R G Y M G G Y M C E C L P G Y N G D N C E D D   Notch3.pro
938   C Q N G A T C M A Q P S G Y L C Q C A P G Y D G Q N C S K E   Notch4.pro 1185  I D E C L S H P C Q N G C T C L D L P N T Y K C S C P R G T   Notch1.pro
1188  V D E C Q N Q P C Q N G G T C I D L V N H F K C S C P P G T   Notch2.pro
1123  V D E C A S Q P C Q H G C S C I D L V A R Y L C S C P P G T   Notch3.pro
968   L D A C Q S Q P C E N - - - - - - - - - - - - - - - - -       Notch4.pro 1215  Q G V H C E I N V D D C N P P V D P V S R S P K C F N N G T   Notch1.pro
1218  R G L L C E E N I D D C - - - - - - A R G P H C L N C G Q     Notch2.pro
1153  L G V L C E I N E D D C G P G - P P L D S G P R C L H N G T   Notch3.pro
979   - - - - - - - - - - - - - - - - - - - - - - - H G T         Notch4.pro 1245  C V D Q V G G Y S C T C P P G F V G E R C E G D V N E C L S   Notch1.pro
1241  C M D R I G G Y S C R C L P G F A G E R C E G D I N E C L S   Notch2.pro
1182  C V D L V G G F R C T C P P G Y T G L R C E A D I N E C R S   Notch3.pro
982   C T P K P G G F H C A C P P G F V G L R C E G D V D E C L D   Notch4.pro 1275  N P C D A R G T Q N C V Q R V N - D F E C E R A G H T G R     Notch1.pro
1271  N P C S S E G S L D C I Q L T N - D Y L C V C R S A F T G R   Notch2.pro
1212  G A C H A A H T R D C L Q D P G G F R C L C H A G F S G P     Notch3.pro
1012  Q P C H P T G T A A C H S L A N - A F Y C Q C L P G H T G Q   Notch4.pro 1304  R C E S V I N G C K G K P C K N G G T C A V A S N T A R G -   Notch1.pro
1300  H C E T F V D V C P Q M P C L N G G T C A V A S N M P D G -   Notch2.pro
1242  R C Q T V L S P C E S Q P C Q H G G Q C R P S P G P G G L     Notch3.pro
1041  W C E V E I D P C H S Q P C F H G G T C E A T A G S P L G -   Notch4.pro 1333  - F I C K C P A G F E G A T C E N D A R T C G S L R C L N G   Notch1.pro
1329  - F I C R C P P G F S G A R C Q S - - - S C G Q V K C R K G   Notch2.pro
1272  T F T C H C A Q P F W G P R C E R V A R S C R E L Q C P V G   Notch3.pro
1070  - F I C H C P K G F E G P T C S H R A P S C G F H H C H H G   Notch4.pro 1362  G T C I S G P R S - - - P T C L C L G P F T G P E C Q F P A   Notch1.pro
1355  E Q C V H T A S G - - - P R C F C P S P R D - - - C E S G C   Notch2.pro
1302  V P C Q Q T P R G - - - P R C A C P P G L S G P S C R S F P   Notch3.pro
1099  G L C L P S P K P G F P P R C A C L S G Y G G P D C L T P P   Notch4.pro
```

FIGURE 2E

```
1389  S S P - - - - - - C L G G N P C Y N Q G T C E P T S - - E S    Notch1.pro
1379  A S - - - - - - - - - S P C Q H G G S C H P Q R - - Q P        Notch2.pro
1329  G S P P G A S N A S C A A A P C L H G G S C R P A P - - L A    Notch3.pro
1129  A P K G - - - - - - C G P P S P C L Y N G S C S E T T G L G G  Notch4.pro 1411  P F Y R C L C P A K F N G L L C H T L D Y S F G G G A G R D    Notch1.pro
1396  P Y Y S C Q C A P P F S G S R C E L Y T - - - - - - - - - -    Notch2.pro
1357  P F F R C A C A Q G W T G P R C E A P A - - - - - - - - - A    Notch3.pro
1154  P G F R C S C P H S S P G P R C Q K P G - - - - - - - - - -    Notch4.pro 1441  I P P P L I E A C E L P E C Q E D A G N K V C S L Q C N N      Notch1.pro
1416  A P P S T P P A T C L S Q Y C A D K A R D G V C D E A C N S    Notch2.pro
1378  A P E V S E P R C P R A A C Q A K R G D Q R C D R E C N S      Notch3.pro
1174  - - - - A K G - - - - - - C E G R S G D G A C D A G C S G      Notch4.pro 1471  H A C C W D C G D C S L N F N D P W K N C T Q S L Q C W K Y    Notch1.pro
1446  H A C Q W D G G D C S L T M E N P W A N C S S P L P C W D Y    Notch2.pro
1408  P G C G W D G G D C S L S V G D P W R Q C - E A L Q C W R L    Notch3.pro
1193  P G G N W D G G D C S L G V P D P W K G C P S H S R C W L L    Notch4.pro 1501  F S D G H C D S Q C N S A G C L F D G F D C Q R A - - E G Q    Notch1.pro
1476  I N N - Q C D E L C N T V E C L F D N F E C Q G N - - S K T    Notch2.pro
1437  F N N S R C D P A C S S P A C L Y D N F D C H A G G R E R T    Notch3.pro
1223  F R D G Q C H P Q C D S E E C L F D G Y D C E T P - - - P A    Notch4.pro 1529  C N P L Y D Q Y C K D H F S D G H C D Q G C N S A E C E W D    Notch1.pro
1503  C K - - Y D K Y C A D H F K D N H C D Q G C N S E F C G W D    Notch2.pro
1467  C N P V Y E K Y C A D H F A D G R C D Q G C N T E F C G W D    Notch3.pro
1250  C T P A Y D Q Y C H D H F H N G H C E K G C N T A E C G W D    Notch4.pro 1559  G L D C A E H V P E R L A A G T L V V V V L M P F E Q L R N    Notch1.pro
1531  G L D C A A D Q P E N L A E G T L V I V V L M P P E Q L L Q    Notch2.pro
1497  G L D C A S E V P A L L A R G V L V L T V L L P P E E L L R    Notch3.pro
1280  G G D C R P E D G D P F W G P S L A L L V L S P P A L D Q      Notch4.pro 1589  S S F H F L R E L S R V L H T N V V F K R D A H G Q Q M I F    Notch1.pro
1561  D A R S F L R A L G T L L H T N L R I K R D S Q G E L M V Y    Notch2.pro
1527  S S A D F L Q R L S A I L R T S L R F R L D A H G Q A M V F    Notch3.pro
1310  Q L F A L A R V L S L T L R V G L W V R K D R D G R D M V Y    Notch4.pro 1619  P Y Y G R E E E L R K H P I K R A A E G W A A P D A L L G Q    Notch1.pro
1591  P Y Y G E K S A A M K K - - - - - - Q - - - - - - - - R        Notch2.pro
1557  P Y H R P S P G S E P R - - - - - - - - - - - - - - -          Notch3.pro
1340  P Y P C A R A E E K L C - - - - - - - G T R D P T Y Q E R      Notch4.pro 1649  V K A S L L P G G S E G G R R R R E L D P M D V R G S I V Y    Notch1.pro
1605  M T R S L P G E - - - - - - Q E - - - Q E V A G S K V F        Notch2.pro
1569  A R R E L A P - - - - - - - - - - - E V I G S V V M            Notch3.pro
1362  A A P Q T Q P L G - - - - - - - - K E T D S L S A G F V V V    Notch4.pro 1679  L E I D N R Q C V Q - - A S S Q C F Q S A T D V A A F L G A    Notch1.pro
1625  L E I D N R Q C V Q - - D S D H C F K N T D A A A L L A S      Notch2.pro
1584  L E I D N R L C L Q S P E N D H C F P D A Q S A A D Y L G A    Notch3.pro
1384  M G V D L S R C G P D H P A S R C P W D P G L L I R F L A A    Notch4.pro 1707  L A S L G S L N - - I P Y K I E A V Q S E T V E P P P P - -    Notch1.pro
1653  H A I Q G T L S - - Y P - - L V S V V S E S L T P - - - -      Notch2.pro
1614  L S A V E R L D - - F P Y P L R D V R G E P L E P P E - - -    Notch3.pro
1414  M A A V G A L E P L L P G P L A V H P A G T A P P A N Q        Notch4.pro
```

FIGURE 2F

```
1733  - A Q L H F M Y V A A A A F V L L F F V G C G V L L S R K R    Notch1.pro
1674  - E R T Q L L Y L L A V A V V I I L F I I L L G V I M A K R    Notch2.pro
1639  - P S V P L L P L L V A G A V L L L V I L V L G V M V A R R    Notch3.pro
1444  L P W P V L C S P V A G V I L L A L G A L L V L Q L I R R R    Notch4.pro 1762  R R Q H G Q L W F P E G F K V S - E A S K - - K K R R E P L    Notch1.pro
1703  K R K H G S L W L P E G F T L R R D A S N - - H K R R E P V    Notch2.pro
1668  K R E H S T L W F P E G F S L E K D V A S G H K G R R E P V    Notch3.pro
1474  R R E H G A L W L P P G F T R R P R T Q S A P H R R R P P L    Notch4.pro 1789  C E D S V G L K P L K N - A S D G A L M D D N Q N E - - W G    Notch1.pro
1731  G Q D A V G L K N L S V Q V S E A N L I G T G T S E H W V D    Notch2.pro
1698  G Q D A L G M K N M A K - - - G E S L M G E V A T D - W M D    Notch3.pro
1504  G E D S I G L K A L K P - - - - - K A E V D E D G - V V M    Notch4.pro 1816  D E D L E T K K F R F E E P V V L P D L D D Q T D H R Q W T    Notch1.pro
1761  D E G P Q P K K V K A E D E A L L S E E D D P I D R R P W T    Notch2.pro
1724  T E C P E A K R L K V E E P C M G - - A E E A V D C R Q W T    Notch3.pro
1527  C S G P E - - - - E G E E V G Q A E E T G P P S T C Q L W S    Notch4.pro 1846  Q Q H L D A A D L R - M S A M A P T P P Q G E V D A D C M D    Notch1.pro
1791  Q Q H L E A A D I R R T P S L A L T P P Q A E Q E V D V L D    Notch2.pro
1752  Q H H L V A A D I R V A P A M A L T P P Q G D A D A D G M D    Notch3.pro
1553  L S G G C G A L P Q - - - A A M L T P P Q - E S E M E A P D    Notch4.pro 1875  V N V R G P D G F T P L M I A S C G G G L E T G N S E E -     Notch1.pro
1821  V N V R G P D G C T P L M L A S L R G G S S D L S D E D E D    Notch2.pro
1782  V N V R G P D G F T P L M L A S F C G G A L E P M P T E E D    Notch3.pro
1579  L D T R G P D G V T P L M S A V C C G - E V Q S G T F Q G -   Notch4.pro 1904  - - E E D A P A V I S D F I Y Q G A S L H N Q T D R T G E T    Notch1.pro
1851  - A E D S S A N T I T D L V Y Q G A S L Q A Q T D R T G E M    Notch2.pro
1812  E A D E T S A S I I S D L I C Q G A Q L G A R T D R T G E T    Notch3.pro
1607  - A W L G C P E P W E P L L D G G A C P Q A H T V G T G E T    Notch4.pro 1932  A L H L A A R Y S R S D A A K R L L E A S A D A N I Q D N M    Notch1.pro
1880  A L H L A A R Y S R A D A A K R L L D A G A D A N A Q D N M    Notch2.pro
1842  A L H L A A R Y A R A D A A K R L L D A G A D T N A Q D H S    Notch3.pro
1636  P L H L A A R F S R P T A A R R L L E A G A N P N Q P D R A    Notch4.pro 1962  G R T P L H A A V S A D A Q G V F Q I L I R N R A T D L D A    Notch1.pro
1910  G R C P L H A A V A A D A Q G V F Q I L I R N R V T D L D A    Notch2.pro
1872  G R T P L H T A V T A D A Q G V F Q I L I R N R S T D L D A    Notch3.pro
1666  G R T P L H A A V A A D A R E V C Q L L L R S R Q T A V D A    Notch4.pro 1992  R M H D G T T P L I L A A R L A V E G M L E D L I N S H A D    Notch1.pro
1940  R M N D G T T P L I L A A R L A V E G M V A E L I N C Q A D    Notch2.pro
1902  R M A D G S T A L I L A A R L A V E G M V E E L I A S H A D    Notch3.pro
1696  R T E D G T T P L M L A A R L A V E D L V E E L I A A Q A D    Notch4.pro 2022  V N A V D D L G K S A L H W A A A V N N V D A A V L L K N    Notch1.pro
1970  V N A V D D H G K S A L H W A A A V N N V E A T L L L L K N    Notch2.pro
1932  V N A V D E L G K S A L H W A A A V N N V E A T L A L L K N    Notch3.pro
1726  V G A R D K W G K T A L H W A A A V N N A R A A R S L L Q A    Notch4.pro 2052  G A N K D M Q N N R E E T P L F L A A R E G S Y E T A K V L    Notch1.pro
2000  G A N R D M Q D N K E E T P L F L A A R E G S Y E A A K I L    Notch2.pro
1962  G A N K D M Q D S K E E T P L F L A A R E G S Y E A A K L L    Notch3.pro
1756  G A D K D A Q D N R E Q T P L F L A A R E G A V E V A Q L L    Notch4.pro
```

FIGURE 2G

```
2082  L D H F A N R D I T D H M D R L P R D I A Q E R M H H D I V   Notch1.pro
2030  L D H F A N R D I T D H M D R L P R D V A R D R M H H D I V   Notch2.pro
1992  L D H F A N R E I T D H L D R L P R D V A Q E R L H Q D I V   Notch3.pro
1786  L G L G A A R E L R D Q A G L A P A D V A H Q R N H W D L L   Notch4.pro 2112  R L L D E Y N L V R S P Q L H G A P L G G T P T L S P P L C   Notch1.pro
2060  R L L D E Y N V T P S P - - P G T V L - - T S A L S P V I C   Notch2.pro
2022  R L L D Q P S G P R S P - - P G P H G - - - - - L G P L L C   Notch3.pro
1816  T L L E G A G P P E A R - - - - - - - - - - - - - - - - - -   Notch4.pro 2142  S P N G Y L G S L K P G V Q G - K K V R K P S S K - - - - -   Notch1.pro
2086  G P N R S F L S L K H T P M G - K K S R R P S A K S T M P T   Notch2.pro
2045  P P G A F L P G L K A A C S G S K K S R R P P G K - - - - -   Notch3.pro
1828  - - - - - - - - H K A T P C R E A G P F P R A R - - - - -   Notch4.pro 2166  G L A C G S K E A K D L K - A R R K S Q D G K G C L L D S   Notch1.pro
2115  S L P N L A K E A K D A K G S R R K S L S E K V Q L S E S   Notch2.pro
2070  - - - - A G L G P Q G P R G R C K K L T L A C P G P L A D S   Notch3.pro
1844  - - - - - - - - - - - - - - - - - - T - - - - - - - - V   Notch4.pro 2195  S G M L S P V D S L E S P H G Y L S D V A S P P L L P S P -   Notch1.pro
2145  S V T L S P V D S L E S P H T Y V S D T T S S P M I T S P G   Notch2.pro
2096  S V T L S P V D S L D S P R P F G G P P A S P G G F P - - -   Notch3.pro
1846  S V S V P P H G G G A L P R C R T L S A G A G P R G G - - -   Notch4.pro 2224  F Q Q S P S V P L N H L P G M P D T H L G I G H L N V A A K   Notch1.pro
2175  I L Q A S P N P M L A T A A P P A P V H A Q H A L S F S N L   Notch2.pro
2123  - - - - - - - - - - - - - - - - L E G P Y A A A T A T A   Notch3.pro
1873  - - - - - - - - - - - - - - - - - - G A C L Q A R T W S   Notch4.pro 2254  P E M A A L G G G G R L A F F T G P P R L S H L P V A S G T   Notch1.pro
2205  H E M Q P L A H G A S T V L P S V S Q L L S H H H I V S - -   Notch2.pro
2135  V S L A Q L G G P G R A G L G R Q P P - - - - - - - - - -   Notch3.pro
1883  V D L A A R G G G A Y S H C R S L S G - - - - - - - - - -   Notch4.pro 2284  S T V L G S S S G G A L N F T V G G S T S L N G Q C E W L S   Notch1.pro
2233  - - - P G S G S A G S L S R - - - - L H P V P V P A D W M N   Notch2.pro
2154  - - - - - G G C V L S L G L - - - - L N P V A V P L D W A R   Notch3.pro
1902  - - - - - V G A G G - - - - - - - - - G - - - - - - - - -   Notch4.pro 2314  R L Q S G M V P N Q Y N P L R C S V A P G P L S T Q A P S L   Notch1.pro
2256  R M E V N E T - - Q Y N E M F G M V L A P A E G T H P G - -   Notch2.pro
2175  - - - - - - - - - - - - - L P P P A P P G P S - - - - -   Notch3.pro
1908  - - - - - - - - - - - - - - - P T P R G R R - - - - -   Notch4.pro 2344  Q H G M V G P L H S S L A A S A L S Q M M S Y Q G L P S T R   Notch1.pro
2282  - - - - - - - - I A - - P - - - - - - - - - Q S R   Notch2.pro
2185  - - - - - - - - - - - - - - - - - - - F L L P   Notch3.pro
1915  - - - - - - - - - - - - - - - - - - - - - -   Notch4.pro 2374  L A T Q P H L V Q T Q Q V Q P Q N L Q M Q Q N L Q P A N I   Notch1.pro
2288  P P E G K H I T T P R E F L P - I V T F Q - - L I P K - -   Notch2.pro
2189  L A P G P Q L L N P G T P V S P - - - - - - - - - - -   Notch3.pro
1915  - - - - - F S A G M R G P R - - - - - - - - - - - -   Notch4.pro 2404  Q Q Q Q S L Q P P P P P Q P H L G V S S A A S G H L G R S   Notch1.pro
2313  - - - G S I A Q P A G A P Q P Q S T C P P A V A G P L P T M   Notch2.pro
2205  - - - - Q E R P P P Y L A V P G H G E E Y P V A G - L - -   Notch3.pro
1924  - - - - - P N P A I M R G R Y G V A A G R G G - - - -   Notch4.pro
```

FIGURE 2H

```
2434   F  L  S  G  E  P  S  Q  A  D  V  Q  P  L  G  P  S  S  L  A  V  H  T  I  L  P  Q  E  S  P   Notch1.pro
2340   Y  Q  I  -  -  P  -  -  -  -  E  M  A  R  L  P  S  V  A  F  P  T  A  M  M  P  Q  Q  D  G  Q   Notch2.pro
2226   -  -  -  -  -  -  -  -  -  -  -  -  -  A  H  S  S  P  P  K  A  R  F  L  R  -  -  -  -    Notch3.pro
1942   -  -  -  -  -  -  -  -  -  -  -  -  -  -  -  -  -  -  -  -  -  -  -  -  -  -  -  -  -  -   Notch4.pro 2464   A  L  P  T  S  L  P  S  S  L  V  P  P  V  T  A  A  Q  F  L  T  P  P  S  Q  H  S  Y  S  S   Notch1.pro
2365   V  A  Q  T  I  L  P  A  Y  H  P  F  P  A  S  V  G  K  Y  P  T  P  P  S  Q  H  S  Y  A  S   Notch2.pro
2238   -  V  P  S  E  H  P  Y  L  T  P  S  P  E  S  P  E  H  W  A  S  P  P  P  S  L  S  D  W   Notch3.pro
1942   -  -  -  -  -  -  -  -  -  -  R  V  S  T  D  D  W  P  C  W  V  A  L  G  A  C  G   Notch4.pro 2494   P  -  -  V  D  N  T  P  S  H  Q  L  Q  V  P  -  E  H  P  F  L  T  P  S  P  E  S  P  D  Q   Notch1.pro
2395   S  N  A  A  E  R  T  P  S  H  S  G  H  L  Q  G  E  H  P  Y  L  T  P  S  P  E  S  P  D  Q   Notch2.pro
2267   S  -  -  -  E  S  T  P  S  P  A  T  A  T  G  -  -  -  A  M  A  T  T  G  A  L  P  A  Q   Notch3.pro
1960   S  -  -  A  S  N  I  P  -  -  -  -  -  -  I  P  P  -  -  P  C  L  T  P  S  P  E  R  G  S  P   Notch4.pro 2521   -  W  S  S  S  P  H  S  N  V  S  D  W  S  E  G  V  S  P  T  S  M  Q  S  Q  I  A   Notch1.pro
2425   -  W  S  S  S  P  H  S  -  A  S  D  W  S  D  V  T  T  S  P  T  P  G  G  A  G  G  G  Q   Notch2.pro
2291   P  L  P  L  S  V  P  S  S  L  A  Q  A  Q  T  Q  L  G  P  Q  P  E  V  T  P  K  R  Q  V  L   Notch3.pro
1981   Q  L  D  C  G  P  P  A  L  Q  E  M  P  I  N  Q  G  G  E  G  K  K   Notch4.pro 2550   R  I  P  E  A  F  K   Notch1.pro
2453   R  G  P  G  T  H  M  S  E  P  P  H  N  N  M  Q  V  Y  A   Notch2.pro
2321   A   Notch3.pro
2002        Notch4.pro
```

FIGURE 3 Statistics of amino acid alignment for Notch1-4

Percent of identity

|  | 1 | 2 | 3 | 4 |  |
|---|---|---|---|---|---|
| 1 |  | 56.1 | 52.7 | 42.6 | 1 |
| 2 | 64.9 |  | 52.7 | 42.5 | 2 |
| 3 | 73.0 | 72.9 |  | 43.4 | 3 |
| 4 | 102.0 | 102.4 | 99.3 |  | 4 |
|  | 1 | 2 | 3 | 4 |  |

Divergence

FIGURE 4A mAb 256A-13 heavy chain variable region sequence

SQVQLQQSGAELAKPGTSVKMACKASGYTFTTHWMNWVKQRPGQGLEWIGTINPSNDFTDCN
                                    CDR-H1                          CDR-H2

QKFKDKAILTADKSSSTAYMQLSSLTSEDSAIYYCASGLTARAWFAYWGQGTLVTVSAA
                                                CDR-H3

(SEQ ID NO: 2)

FIGURE 4B mAb 256A-13 light chain (kappa) variable region sequence

RATISCRASQSVTTSNYSYMHWFQQKPGQPPKLLIKYASNLDSGVPARFSGSGSGTDFTLNI
       CDR-L1                         CDR-L2

HPVEEEDTATFYCQHSWEIPYTFGGGTNLEIKRADAAPTV    (SEQ ID NO: 3)
            CDR-L3

FIGURE 5 LIGAND INDEPENDENT NOTCH3 SIGNALING
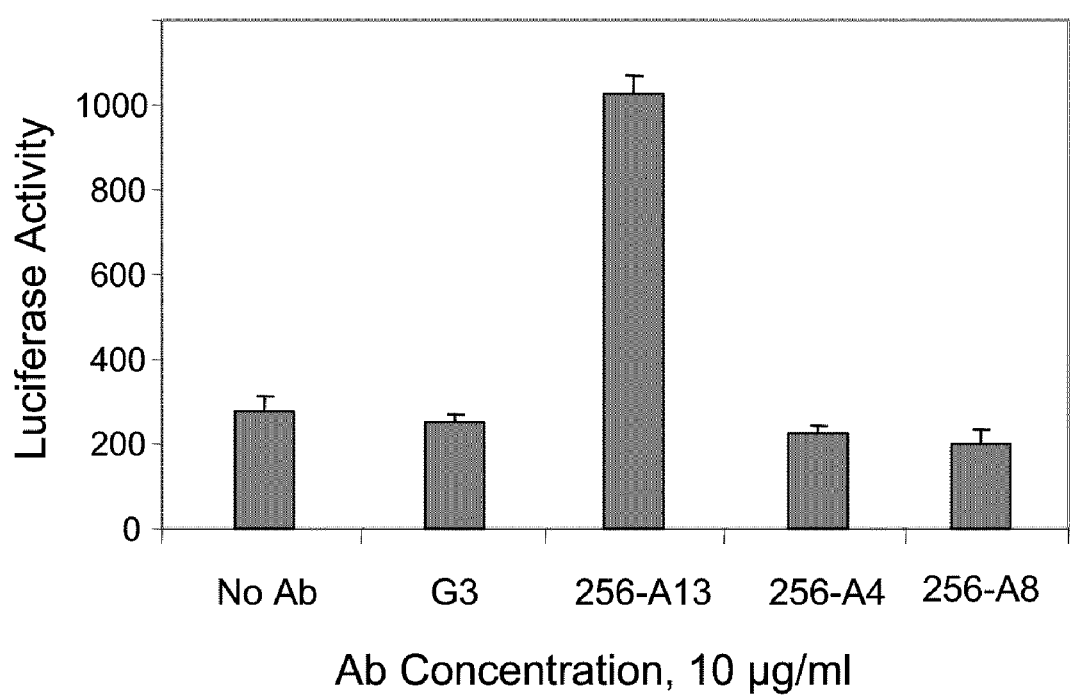

FIGURE 6  METALLOPROTEASE CLEAVAGE OF NOTCH3
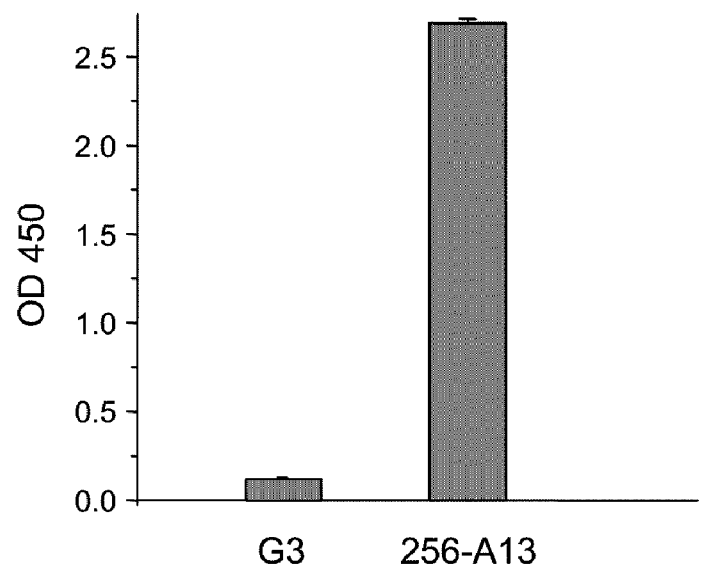

FIGURE 7 NOTCH3/Fc PROTEIN CONSTRUCTS FOR EPITOPE MAPPING
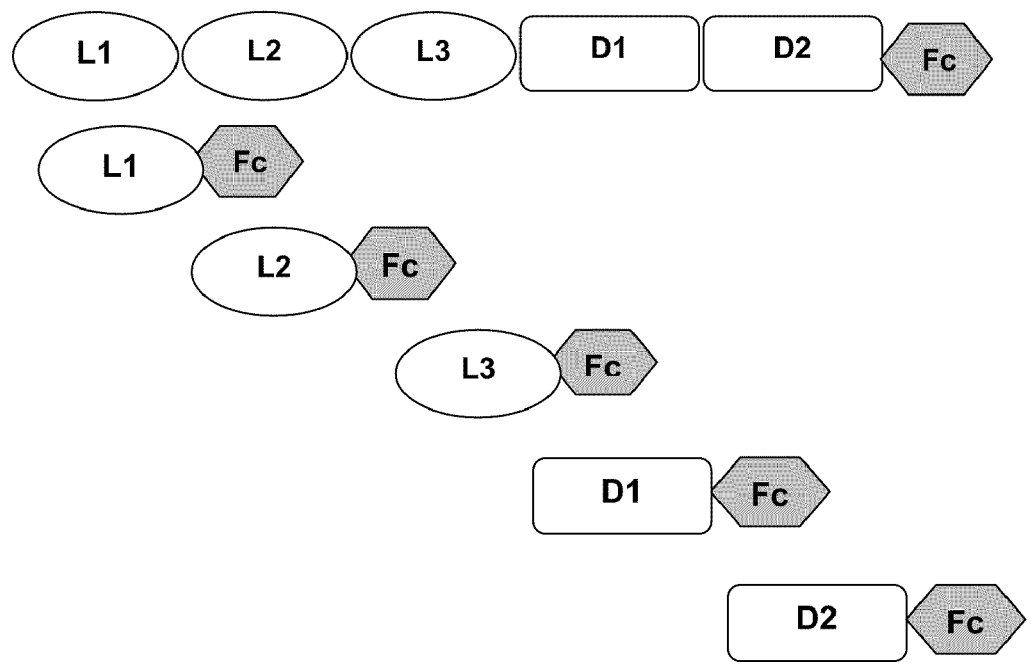

FIGURE 8A

```
1    A T G G G T C C A G G T G C A A G A G G    N3-leader Tanox.
1    A T G G G G C C G G G G G C C C G T G G    N3-leader NCBI.s 21   T A G A A G G C G T A G A A G G A G A C    N3-leader Tanox.
21   C C G C C G C C G C C G C C G T C G C C    N3-leader NCBI.s 41   C A A T G A G C C A C C T C C T C C G      N3-leader Tanox.
41   C G A T G T C G C C G C C A C C G C C A    N3-leader NCBI.s 61   C C A C C T C C A G T G A G A G C A C T    N3-leader Tanox.
61   C C G C C A C C C G T G C G G G C G C T    N3-leader NCBI.s 81   G C C T T T G C T G T T G C T G C T G G    N3-leader Tanox.
81   G C C C C T G C T G C T G C T G C T A G    N3-leader NCBI.s 101  C T G G A C C T G G T G C A G C A G C T    N3-leader Tanox.
101  C G G G C C G G G G C T G C A G C C       N3-leader NCBI.s 121  C C T C C T T G C C T G G A C              N3-leader Tanox.
121  C C C C C T T G C C T G G A C              N3-leader NCBI.s
```

FIGURE 8C
EPRCPRAACQ AKRGDQRCDR ECNSPGCGWD GGDCSLSVG (SEQ ID NO 10)

FIGURE 8D
AKRGDQRCDR ECNSPGCGWD GGDCSLSVG (SEQ ID NO 11)

FIGURE 10 Summary of subdomain swap and amino acid (aa) cluster swap sequence in first LIN12 domain and Mab binding strength in ELISA assays

| Expression constructs | Sequence ID | Wild type and swapped sequences of Notch3 1st LIN12 (L1) domain | 256A-13 | G3 | Hu-Fc | % of difference |
|---|---|---|---|---|---|---|
| Notch3-L1 | 10 | EPRCPRAACQAKRGDQRCDRECNSPGCGWDGGDCSLSVG | +++ | - | +++ | 0 |
| L1-sub1 | 14 | -EACELPE------------------------------- | +++ | - | +++ | 15.34 |
| L1-sub2 | 15 | ----------EDAGNKVCS-------------------- | + | - | +++ | 17.95 |
| L1-aa swap1 | 17 | ----------EDA-------------------------- | +++ | - | ++ | 20.51 |
| L1-aa swap2 | 18 | --------------NKV---------------------- | +++ | - | ++ | 7.69 |
| L1-sub3 | 16 | -------------------LQCNNHACGWDGGDCSLNFN | + | - | +++ | 7.69 |
| L1-aa swap3 | 19 | -------------------SLQ----------------- | - | - | +++ | 7.69 |
| L1-aa swap4 | 20 | -----------------------NHA------------- | +++ | - | +++ | 7.69 |
| L1-aa swap5 | 21 | ------------------------------------NFN | +++ | - | +++ | 7.69 |

In these ELISA experiments, binding of Mab 256A-13 to Notch3-LD/Fc (L1) was used as positive control, i.e. 100% binding. Binding read-out to swap recombinant proteins were compared to that of positive standard. +++ : >50% of standard binding; ++: 10-40% of standard binding; +: 10% to minimum positive signal. -: no binding, i.e. Mab G3 mean binding read-out +/- 3 X standard error. Mab G3 is a human IgG1 control Mab used as negative control.

FIGURE 11 Alanine scanning peptides for epitope mapping of 256A-13

| Expression constructs | Sequence ID | Wild type and swapped sequences of Notch3 1st LIN12 (L1) domain |
|---|---|---|
| Notch3-L1 | 10 | EPRCPRAACQAKRGDQRCDRECNSPGCGWDGGDCSLSVG |
| AA-scan 1 | 22 | AACQAAAGDQRC |
| AA-scan 2 | 23 | ACQAKAADQRCD |
| AA-scan 3 | 24 | CQAKRAAQRCDR |
| AA-scan 4 | 25 | QAKRGAARCDRE |
| AA-scan 5 | 26 | AKRGDAACDREC |
| AA-scan 6 | 27 | KRGDQAADRECN |
| AA-scan 7 | 28 | RGDQRAARECNS |
| AA-scan 8 | 29 | GDQRCAAECNSP |
| AA-scan 9 | 30 | DQRCDAACNSPG |
| AA-scan 10 | 31 | QRCDRAANSPGC |
| AA-scan 11 | 32 | RCDREAASPGCG |
| AA-scan 12 | 33 | CDRECAAPGCGW |
| AA-scan 13 | 34 | DRECNAAGCGWD |
| AA-scan 14 | 35 | RECNSAACGWDG |
| AA-scan 15 | 36 | ECNSPAAGWDGG |
| AA-scan 16 | 37 | CNSPGAAWDGGD |

ANTI-NOTCH3 AGONIST ANTIBODIES AND THEIR USE IN THE TREATMENT OF NOTCH3-RELATED DISEASES

CROSS-REFERENCE TO RELATED APPLICATIONS

This application claims the benefit of U.S. Provisional Application No. 60/852,861, filed Oct. 19, 2006, and U.S. Provisional Application No. 60/879,218, filed Jan. 6, 2007, the disclosures of which are incorporated herein by reference in their entirety. This application also claims the benefit of U.S. Provisional Application No. 60/875,597, filed Dec. 18, 2006.

FIELD OF THE INVENTION

The present invention relates to anti-Notch3 agonist antibodies and their use in the amelioration, treatment, or prevention of a Notch3-related disease or disorder.

BACKGROUND OF THE INVENTION

The Notch gene was first described in 1917 when a strain of the fruit fly *Drosophila melanogaster* was found to have notched wing blades (Morgan, *Am Nat* 51:513 (1917)). The gene was cloned almost seventy years later and was determined to be a cell surface receptor playing a key role in the development of many different cell types and tissues in *Drosophila* (Wharton et al., *Cell* 43:567 (1985)). The Notch signaling pathway was soon found to be a signaling mechanism mediated by cell-cell contact and has been evolutionarily conserved from *Drosophila* to human. Notch receptors have been found to be involved in many cellular processes, such as differentiation, cell fate decisions, maintenance of stem cells, cell motility, proliferation, and apoptosis in various cell types during development and tissue homeostasis (See review Artavanis-Tsakonas, et al., *Science* 268:225 (1995)).

Mammals possess four Notch receptor proteins (designated Notch1 to Notch4) and five corresponding ligands (designated Delta Like-1 (DLL-1), Delta Like-3 (DLL-3), Delta Like-4 (DLL-4), Jagged-1 and Jagged-2). The mammalian Notch receptor genes encode ~300 kD proteins that are cleaved during their transport to the cell surface and exist as heterodimers. The extracellular portion of the Notch receptor has thirty-four epidermal growth factor (EGF)-like repeats and three cysteine-rich Notch/LIN12 repeats. The association of two cleaved subunits is mediated by sequences lying immediately N-terminal and C-terminal of the cleavage site, and these two subunits constitute the Notch heterodimerization (HD) domains (Wharton, et al., *Cell* 43:567 (1985); Kidd, et al., *Mol Cell Biol* 6:3431 (1986); Kopczynski, et al., *Genes Dev* 2:1723 (1988); Yochem, et al., *Nature* 335:547 (1988)).

At present, it is still not clear how Notch signaling is regulated by different receptors or how the five ligands differ in their signaling or regulation. The differences in signaling and/or regulation may be controlled by their expression patterns in different tissues or by different environmental cues. It has been documented that Notch ligand proteins, including Jagged/Serrate and Delta/Delta-like, specifically bind to the EGF repeat region and induce receptor-mediated Notch signaling (reviewed by Bray, *Nature Rev Mol Cell Biol.* 7:678 (2006), and by Kadesch, *Exp Cell Res.* 260:1 (2000)). Among the EGF repeats, the 10th to 12th repeats are required for ligand binding to the Notch receptor, and the other EGF repeats may enhance receptor-ligand interaction (Xu, et al., *J Biol Chem.* 280:30158 (2005); Shimizu, et al., *Biochem Biophys Res Comm.* 276:385 (2000)). Although the LIN12 repeats and the dimerization domain are not directly involved in ligand binding, they play important roles in maintaining the heterodimeric protein complex, preventing ligand-independent protease cleavage and receptor activation (Sanche-Irizarry, et al., *Mol Cell Biol.* 24:9265 (2004); Vardar et al., *Biochem.* 42:7061 (2003)).

Normal stem cells from many tissues including intestinal and neuronal stem cells depend on Notch signaling for self-renewal and fate determination (Fre, et al., *Nature,* 435: 964 (2005); van Es, et al., *Nature,* 435: 959 (2005); Androutsellis-Theotokis, et al., *Nature,* 442: 823 (2006)). Therefore, the Notch3 agonistic antibody could have application in degenerative diseases. CADASIL (cerebral autosomal dominant arteriopathy with subcortical infarcts and leukoencephalopathy) causes a type of stroke and dementia whose key features include recurrent subcortical ischaemic events and vascular dementia. CADASIL has been found to be associated with a mutant gene localized to chromosome 19 (Joutel, et al., *Nature* 383:707 (1996)). Joutel et al. identified mutations in CADASIL patients that cause serious disruption of the Notch 3 gene, indicating that Notch3 could be the defective protein in CADASIL patients. Unfortunately, this highly incapacitating and often lethal disease has remained largely undiagnosed or misdiagnosed as multiple sclerosis and Alzheimer's disease. Current studies would tend to demonstrate that it is a condition that is much more widespread than first thought.

An additional example of a Notch 3 related disease is familial hemiplegic migraine (FHM), the dominant autosomal form of migraine with aura, located in the same region of chromosome 19 as the Notch3 gene. It should be noted that more than 30% of patients suffering from CADASIL also suffer from migraine with aura. However, the latter is observed in only about 5% of the population and this observation led to the discovery of Notch3 gene involvement in the mechanism of this condition. Similarly, familial paroxytic ataxia has been linked to a gene located in the same region of chromosome 19 and Notch3 has been implicated in this condition. Other conditions and diseases that have been linked to Notch3 include Alagille syndrome (Flynn, et al., *J Pathol* 204:55 (2004)).

Ongoing research studies are currently being pursued to identify other diseases and conditions linked to Notch3 expression and/or signaling deficiencies. In view of the large number of human diseases associated with the Notch 3 signaling pathway, it is important that new ways of preventing and treating these diseases be identified. The current invention provides novel anti-Notch 3 agonist antibodies useful for this unmet medical need.

SUMMARY OF THE INVENTION

The present invention provides novel agonist antibodies and fragments thereof that specifically bind to an epitope of the human Notch3 receptor in the LIN12 domain. Another aspect of the invention includes the epitope binding site and antibodies that bind this same epitope as the antibodies of the present invention. The antibodies of the present invention activate Notch3-mediated signaling through the Notch3 receptor independent of ligand binding.

The invention includes the amino acid sequences of the variable heavy and light chain of the antibodies and their corresponding nucleic acid sequences. Another embodiment of the invention includes the CDR sequences of these antibodies.

Another embodiment of the present invention includes the cell lines and vectors harboring the antibody sequences of the present invention.

The present invention also includes the epitope recognized by the agonist antibodies of the invention. The present invention also includes antibodies that bind this epitope. The embodiments include a Notch 3 epitope comprising the Lin 12 domain having at least 80%, 85%, 90%, or 95% sequence identity with SEQ ID NO. 10. More particularly, the Notch 3 epitope comprises SEQ ID NO 11. The present invention includes agonist antibodies that bind this epitope.

Another embodiment of the present invention is the use of these antibodies for the preparation of a medicament or composition for the treatment of Notch 3 related diseases and disorders associated with e.g., receptor inactivation.

Another embodiment of the preset invention is the use of these antibodies in the treatment of Notch 3 related diseases or disorders associated with e.g. receptor inactivation comprising the activation of said defects by, e.g., activating Notch 3 signaling independent of ligand binding. Notch 3 related disorders may include, but not limited to, CADASIL, familial hemiplegics migraine (FHM), familial paroxytic ataxia, Alagille syndrome and other degenerative diseases.

BRIEF DESCRIPTION OF THE FIGURES

FIG. 1 depicts the amino acid sequence of Notch3. The EGF repeat region extends from amino acid residue 43 to 1383; the LIN12 domain extends from amino acid residue 1384 to 1503; and the dimerization domain extends from amino acid residue 1504 to 1640.

FIG. 2 (A-H) depicts the amino acid sequence comparison between human Notch 1 (SEQ ID NO:39), Notch 2 (SEQ ID NO:40), Notch 3 (SEQ ID NO:1), and Notch 4 (SEQ ID NO:41).

FIG. 3 depicts the percent identity of Notch 1, Notch 2, Notch 3, and Notch 4.

FIGS. 4A and 4B depict the heavy and light chain variable region sequences of anti-Notch3 monoclonal antibody MAb 256A-13 (SEQ ID NO:2 and SEQ ID NO:3, respectively), with the following CDR regions underlined: CDR-H1 (SEQ ID NO:4), CDR-H2 (SEQ ID NO:5), CDR-H3 (SEQ ID NO:6), CDR-L1 (SEQ ID NO:7), CDR-L2 (SEQ ID NO:8) and CDR-L3 (SEQ ID NO:9).

FIG. 5 depicts a luciferase reporter assay of Example 5 showing activating effects by anti-Notch3 MAbs on the Notch3 receptor.

FIG. 6 depicts the impact of Notch3 agonistic antibodies on metalloprotease cleavage of Notch3.

FIG. 7 depicts Notch3-Fc fusion protein constructs for epitope mapping of the binding site of 256A-13.

FIGS. 8A and 8B depict the comparison of the engineered Notch3 leader peptide coding sequence (SEQ ID NO:42, upper row in FIG. 8A) to the native Notch3 leader peptide coding sequence (NCBI GenBank Accession No. NM_000435) (SEQ ID NO:43, lower row in FIG. 8A) showing the changes of nucleotides (FIG. 8A) and the translated amino acid sequence of the engineered Notch leader peptide sequence (SEQ ID NO:44, FIG. 8B). FIG. 8C depicts the LIN12 domain (SEQ ID NO:10) and FIG. 8D depicts a sub-domain epitope of LIN12 (SEQ ID NO:11).

FIG. 10 depicts the amino acid sequences used in the Notch3 LIN12 domain epitope mapping of the MAb 256A-13.

FIG. 11 depicts the Alanine scanning peptides for linear epitope mapping of 256A-13.

DETAILED DESCRIPTION

Figure 9:
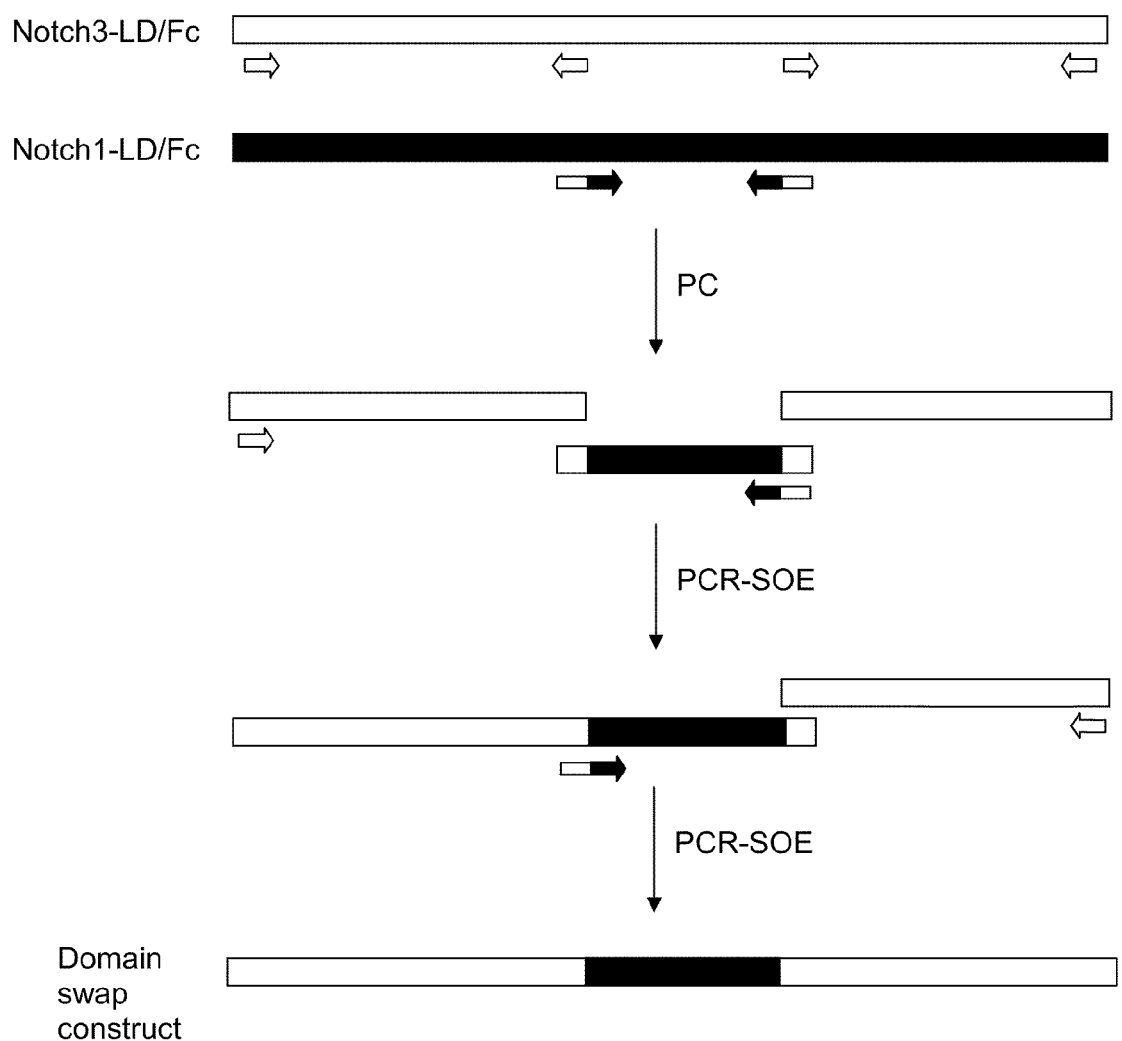
FIG. 9 depicts the generation of domain swap construct by PCR-SOE method. Arrow bars represent PCR primers. Open bar, Notch3 sequence. Filled bar, Notch1 sequence.

This invention is not limited to the particular methodology, protocols, cell lines, vectors, or reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly dictates otherwise, e.g., reference to "a host cell" includes a plurality of such host cells. Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

All patents and publications mentioned herein are incorporated herein by reference to the extent allowed by law for the purpose of describing and disclosing the proteins, enzymes, vectors, host cells, and methodologies reported therein that might be used with the present invention. However, nothing herein is to be construed as an admission that the invention is not entitled to antedate such disclosure by virtue of prior invention.

DEFINITIONS

Terms used throughout this application are to be construed with ordinary and typical meaning to those of ordinary skill in the art. However, Applicants desire that the following terms be given the particular definition as defined below.

The phrase "substantially identical" with respect to an antibody chain polypeptide sequence may be construed as an antibody chain exhibiting at least 70%, or 80%, or 90%, or 95% sequence identity to the reference polypeptide sequence. The term with respect to a nucleic acid sequence may be construed as a sequence of nucleotides exhibiting at least about 85%, or 90%, or 95%, or 97% sequence identity to the reference nucleic acid sequence.

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software.

The term "antibody" is used in the broadest sense, and specifically covers monoclonal antibodies (including full length monoclonal antibodies), polyclonal antibodies, and multispecific antibodies (e.g., bispecific antibodies), and antibody fragments so long as they exhibit the desired biological activity. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. The antibodies of the invention can be of any type (e.g., IgG, IgE, IgM, IgD, IgA and IgY), class (e.g., IgG1, IgG2, IgG3, IgG4, IgA1 and IgA2) or subclass. Native antibodies and immunoglobulins are usually heterotetrameric glycoproteins of about 150,000 Daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end.

As used herein, "anti-Notch3 antibody" means an antibody which binds specifically to human Notch3 in such a manner so as to activate Notch 3 signaling independent of ligand.

The term "variable" in the context of variable domain of antibodies, refers to the fact that certain portions of the variable domains differ extensively in sequence among antibodies and are used in the binding and specificity of each particular antibody for its particular target. However, the variability is not evenly distributed through the variable domains of antibodies. It is concentrated in three segments called complementarity determining regions (CDRs; i.e., CDR1, CDR2, and CDR3) also known as hypervariable regions both in the light chain and the heavy chain variable domains. The more highly conserved portions of variable domains are called the framework (FR). The variable domains of native heavy and light chains each comprise four FR regions, largely a adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies (see Kabat, et al. Sequences of Proteins of Immunological Interest, National Institute of Health, Bethesda, Md. (1987)). As used herein, numbering of immunoglobulin amino acid residues is done according to the immunoglobulin amino acid residue numbering system of Kabat, et al., unless otherwise indicated.

The term "antibody fragment" refers to a portion of a full-length antibody, generally the target binding or variable region. Examples of antibody fragments include F(ab), F(ab'), F(ab')$_2$ and Fv fragments. The phrase "functional fragment or analog" of an antibody is a compound having qualitative biological activity in common with a full-length antibody. For example, a functional fragment or analog of an anti-Notch3 antibody is one which can bind to a Notch3 receptor in such a manner so as to prevent or substantially reduce the ability of the receptor to bind to its ligands or initiate signaling. As used herein, "functional fragment" with respect to antibodies, refers to Fv, F(ab) and F(ab')$_2$ fragments. An "Fv" fragment consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. However, even a single variable domain (or half of an Fv comprising only three CDRs specific for a target) has the ability to recognize and bind target, although at a lower affinity than the entire binding site.

"Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding.

The term "diabodies" refers to small antibody fragments with two antigen-binding sites, which fragments comprise a heavy chain variable domain ($V_H$) connected to a light chain variable domain ($V_L$) in the same polypeptide chain. By using a linker that is too sort to allow pairing between the two domains on the same chain, the domains are forced to pair with the complementary domains of another changing and create two antigen-binding sites.

The F(ab) fragment contains the constant domain of the light chain and the first constant domain (CH1) of the heavy chain. F(ab') fragments differ from F(ab) fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, which the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison, et al., *Proc Natl Acad Sci USA* 81:6851 (1984)). Monoclonal antibodies are highly specific, being directed against a single target site. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using the well known techniques. The parent monoclonal antibodies to be used in accordance with the present invention may be made by the hybridoma method first described by Kohler, et al., *Nature* 256:495 (1975), or may be made by recombinant methods.

"Humanized" forms of non-human (e.g., murine) antibodies are chimeric immunoglobulins, immunoglobulin chains or fragments thereof (such as Fv, Fab, Fab', F(ab')$_2$ or other target-binding subsequences of antibodies) which contain minimal sequence derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region (Fc), typically that of a human immunoglobulin template chosen.

The terms "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included. The "host cells" used in the present invention generally are prokaryotic or eukaryotic hosts.

"Transformation" of a cellular organism, cell, or cell line with DNA means introducing DNA into the target cell so that the DNA is replicable, either as an extrachromosomal element or by chromosomal integration. "Transfection" of a cell or organism with DNA refers to the taking up of DNA, e.g., an expression vector, by the cell or organism whether or not any coding sequences are in fact expressed. The terms "transfected host cell" and "transformed" refer to a cell in which DNA was introduced. The cell is termed "host cell" and it may be either prokaryotic or eukaryotic. Typical prokaryotic host cells include various strains of E. coli. Typical eukaryotic host cells are mammalian, such as Chinese hamster ovary or cells of human origin. The introduced DNA sequence may be from the same species as the host cell of a different species from the host cell, or it may be a hybrid DNA sequence, containing some foreign and some homologous DNA.

The term "vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the invention is intended to include such other forms of vectors which serve equivalent function as and which are, or become, known in the art.

"Mammal" for purposes of treatment refers to any animal classified as a mammal, including human, domestic and farm animals, nonhuman primates, and zoo, sports, or pet animals, such as dogs, horses, cats, cows, etc.

The word "label" when used herein refers to a detectable compound or composition which can be conjugated directly or indirectly to a molecule or protein, e.g., an antibody. The label may itself be detectable (e.g., radioisotope labels or fluorescent labels) or, in the case of an enzymatic label, may catalyze chemical alteration of a substrate compound or composition which is detectable.

As used herein, "solid phase" means a non-aqueous matrix to which the antibody of the present invention can adhere. Example of solid phases encompassed herein include those formed partially or entirely of glass (e.g., controlled pore glass), polysaccharides (e.g., agarose), polyacrylamides, polystyrene, polyvinyl alcohol, and silicones. In certain embodiments, depending on the context, the solid phase can comprise the well of an assay plate; in others it is a purification column (e.g., an affinity chromatography column).

As used herein, the term "Notch3-mediated disorder" means a condition or disease which is characterized by the defective or underexpressed Notch3 receptor. Specifically it would be construed to include conditions associated with degenerative diseases such as. CADASIL, FHM, familial paroxytic ataxia, Alagille syndrome, and other degenerative diseases.

Notch 3 Receptor Immunogen for Generating Antibodies

Soluble targets or fragments thereof can be used as immunogens for generating antibodies. The antibody is directed against the target of interest. Preferably, the target is a biologically important polypeptide and administration of the antibody to a mammal suffering from a disease or disorder can result in a therapeutic benefit in that mammal. Whole cells may be used as the immunogen for making antibodies. The immunogen may be produced recombinantly or made using synthetic methods. The immunogen may also be isolated from a natural source.

For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to over-express the transmembrane molecule. Other forms of the immunogen useful for preparing antibodies will be apparent to those in the art.

Alternatively, a gene or a cDNA encoding human Notch3 receptor may be cloned into a plasmid or other expression vector and expressed in any of a number of expression systems according to methods well known to those of skill in the art. Methods of cloning and expressing Notch3 receptor and the nucleic acid sequence for human Notch3 receptor are known (see, for example, U.S. Pat. Nos. 5,821,332 and 5,759, 546). Because of the degeneracy of the genetic code, a multitude of nucleotide sequences encoding Notch3 receptor protein or polypeptides may be used. One may vary the nucleotide sequence by selecting combinations based on possible codon choices. These combinations are made in accordance with the standard triplet genetic code as applied to the nucleotide sequence that codes for naturally occurring Notch3 receptor and all such variations may be considered. Any one of these polypeptides may be used in the immunization of an animal to generate antibodies that bind to human Notch3 receptor.

Recombinant Notch3 proteins from other species may also be used as immunogen to generate antibodies because of the high degree of conservation of the amino acid sequence of Notch3. A comparison between human and mouse Notch3 showed that over 90% amino acid sequences are identical between the two species.

The immunogen Notch3 receptor may, when beneficial, be expressed as a fusion protein that has the Notch3 receptor attached to a fusion segment. The fusion segment often aids in protein purification, e.g., by permitting the fusion protein to be isolated and purified by affinity chromatography, but can also be used to increase immunogenicity. Fusion proteins can be produced by culturing a recombinant cell transformed with a fusion nucleic acid sequence that encodes a protein including the fusion segment attached to either the carboxyl and/or amino terminal end of the protein. Fusion segments may include, but are not limited to, immunoglobulin Fc regions, glutathione-S-transferase, β-galactosidase, a poly-histidine segment capable of binding to a divalent metal ion, and maltose binding protein.

Recombinant Notch3 receptor protein as described in Example 1 was used to immunize mice to generate the hybridomas that produce the monoclonal antibodies of the present invention. Exemplary polypeptides comprise all or a portion of SEQ ID NO. 1 or variants thereof.

Antibody Generation

The antibodies of the present invention may be generated by any suitable method known in the art. The antibodies of the present invention may comprise polyclonal antibodies. Methods of preparing polyclonal antibodies are known to the skilled artisan (Harlow, et al., Antibodies: a Laboratory Manual, Cold spring Harbor Laboratory Press, 2nd ed. (1988)), which is hereby incorporated herein by reference in its entirety).

For example, an immunogen as described in Example 1 may be administered to various host animals including, but not limited to, rabbits, mice, rats, etc., to induce the production of sera containing polyclonal antibodies specific for the antigen. The administration of the immunogen may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Additional examples of adjuvants which may be employed include the MPL-TDM adjuvant (monophosphoryl lipid A, synthetic trehalose dicorynomycolate). Immunization protocols are well known in the art in the art and may be performed by any method that elicits an immune response in the animal host chosen. Adjuvants are also well known in the art.

Typically, the immunogen (with or without adjuvant) is injected into the mammal by multiple subcutaneous or intraperitoneal injections, or intramuscularly or through IV. The immunogen may include a Notch3 polypeptide, a fusion protein, or variants thereof. Depending upon the nature of the polypeptides (i.e., percent hydrophobicity, percent hydrophilicity, stability, net charge, isoelectric point etc.), it may be useful to conjugate the immunogen to a protein known to be immunogenic in the mammal being immunized. Such conjugation includes either chemical conjugation by derivatizing active chemical functional groups to both the immunogen and the immunogenic protein to be conjugated such that a covalent bond is formed, or through fusion-protein based methodology, or other methods known to the skilled artisan. Examples of such immunogenic proteins include, but are not limited to, keyhole limpet hemocyanin, ovalbumin, serum albumin, bovine thyroglobulin, soybean trypsin inhibitor, and promiscuous T helper peptides. Various adjuvants may be used to increase the immunological response as described above.

The antibodies of the present invention comprise monoclonal antibodies. Monoclonal antibodies are antibodies which recognize a single antigenic site. Their uniform specificity makes monoclonal antibodies much more useful than polyclonal antibodies, which usually contain antibodies that recognize a variety of different antigenic sites. Monoclonal antibodies may be prepared using hybridoma technology, such as those described by Kohler, et al., *Nature* 256:495 (1975); U.S. Pat. No. 4,376,110; Harlow, et al., Antibodies: A Laboratory Manual, Cold spring Harbor Laboratory Press, 2nd ed. (1988) and Hammerling, et al., Monoclonal Antibodies and T-Cell Hybridomas, Elsevier (1981), recombinant DNA methods, or other methods known to the artisan. Other examples of methods which may be employed for producing monoclonal antibodies include, but are not limited to, the human B-cell hybridoma technique (Kosbor, et al., *Immunology Today* 4:72 (1983); Cole, et al., *Proc Natl Acad Sci USA* 80:2026 (1983)), and the EBV-hybridoma technique (Cole, et al., Monoclonal Antibodies and Cancer Therapy, pp. 77-96, Alan R. Liss (1985)). Such antibodies may be of any immunoglobulin class including IgG, IgM, IgE, IgA, IgD and any subclass thereof. The hybridoma producing the MAb of this invention may be cultivated in vitro or in vivo.

In the hybridoma model, a host such as a mouse, a humanized mouse, a mouse with a human immune system, hamster, rabbit, camel, or any other appropriate host animal, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, Academic Press, pp. 59-103 (1986)).

Generally, in making antibody-producing hybridomas, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, pp. 59-103 (1986)). Immortalized cell lines are usually transformed mammalian cells, particularly myeloma cells of rodent, bovine or human origin. Typically, a rat or mouse myeloma cell line is employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), substances that prevent the growth of HGPRT-deficient cells.

Preferred immortalized cell lines are those that fuse efficiently, support stable high-level production of antibody by the selected antibody-producing cells, and are sensitive to a medium such as HAT medium. Among these myeloma cell lines are murine myeloma lines, such as those derived from the MOPC-21 and MPC-11 mouse tumors available from the Salk Institute Cell Distribution Center, San Diego, Calif. U.S. Application No., and SP2/0 or X63-Ag8-653 cells available from the American Type Culture Collection, Rockville, Md. USA. Human myeloma and mouse-human heteromyeloma cell lines also have been described for the production of human monoclonal antibodies (Kozbor, *J Immunol* 133:3001 (1984); Brodeur, et al., Monoclonal Antibody Production Techniques and Applications, Marcel Dekker, Inc, pp. 51-63 (1987)). The mouse myeloma cell line NSO may also be used (European Collection of Cell Cultures, Salisbury, Wilshire, UK).

The culture medium in which hybridoma cells are grown is assayed for production of monoclonal antibodies directed against Notch3. The binding specificity of monoclonal antibodies produced by hybridoma cells may be determined by immunoprecipitation or by an in vitro binding assay, such as radioimmunoassay (RIA) or enzyme-linked immunoabsorbent assay (ELISA). Such techniques are known in the art and within the skill of the artisan. The binding affinity of the monoclonal antibody to Notch3 can, for example, be determined by a Scatchard analysis (Munson, et al., *Anal Biochem* 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, Academic Press, pp. 59-103 (1986)). Suitable culture media for this purpose include, for example, Dulbecco's Modified Eagle's Medium (D-MEM) or RPMI-1640 medium. In addition, the hybridoma cells may be grown in vivo as ascites tumors in an animal.

The monoclonal antibodies secreted by the subclones are suitably separated or isolated from the culture medium, ascites fluid, or serum by conventional immunoglobulin purification procedures such as, for example, protein A-SEPHAROSE® affinity media, hydroxylaptite chromatography, gel exclusion chromatography, gel electrophoresis, dialysis, or affinity chromatography.

A variety of methods exist in the art for the production of monoclonal antibodies and thus, the invention is not limited to their sole production in hybridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. DNA encoding the monoclonal antibodies of the invention is readily isolated and sequenced using conventional procedures (e.g., by using oligonucleotide probes that are capable of binding specifically to genes encoding the heavy and light chains of murine antibodies, or such chains from human, humanized, or other sources) (Innis, et al. In PCR Protocols. A Guide to Methods and Applications, Academic (1990), Sanger, et al., *Proc Natl Acad Sci* 74:5463 (1977)). The hybridoma cells serve as a source of such DNA. Once isolated, the DNA may be placed into expression vectors, which are then transfected into host cells such as *E. coli* cells, NS0 cells, Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison, et al., *Proc Natl Acad Sci USA* 81:6851 (1984)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

Antibody fragments which recognize specific epitopes may be generated by known techniques. Traditionally, these fragments were derived via proteolytic digestion of intact antibodies (see, e.g., Morimoto, et al., *J Biochem Biophys Methods* 24:107 (1992); Brennan, et al., *Science* 229:81 (1985)). For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. However, these fragments can now be produced directly by recombinant host ells. For example, the antibody fragments can be isolated from an antibody phage library. Alternatively, F(ab')$_2$—SH fragments can be directly recovered from *E. coli* and chemically coupled to form F(ab')$_2$ fragments (Carter, et al., *Bio/Technology* 10:163 (1992). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (Fv) (PCT patent application WO 93/16185).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science* 229:1202 (1985); Oi, et al., *BioTechniques* 4:214 (1986); Gillies, et al., *J Immunol Methods* 125:191 (1989); U.S. Pat. Nos. 5,807,715; 4,816,567; and 4,816397, which are incorporated herein by reference in their entirety.

A humanized antibody is designed to have greater homology to a human immunoglobulin than animal-derived monoclonal antibodies. Humanization is a technique for making a chimeric antibody wherein substantially less than an intact human variable domain has been substituted by the corresponding sequence from a non-human species. Humanized antibodies are antibody molecules generated in a non-human species that bind the desired antigen having one or more complementarity determining regions (CDRs) from the non-human species and framework (FR) regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., U.S. Pat. No. 5,585,089; Riechmann, et al., *Nature* 332:323 (1988), which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28:489 (1991); Studnicka, et al., *Protein Engineering* 7:805 (1994); Roguska, et al., *Proc Natl Acad Sci USA* 91:969 (1994)), and chain shuffling (U.S. Pat. No. 5,565,332).

Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones, et al., *Nature* 321:522 (1986); Riechmann, et al., *Nature* 332:323 (1988); Verhoeyen, et al., *Science* 239:1534 (1988)), by substituting non-human CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

It is further important that humanized antibodies retain higher affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of certain residues in the functioning of the candidate immunoglobulin sequence, i.e., the analysis of residues that influence the ability of the candidate immunoglobulin sequences, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is maximized, although it is the CDR residues that directly and most substantially influence antigen binding.

The choice of human variable domains, both light and heavy, to be used in making the humanized antibodies is important to reduce antigenicity. According to the so-called "best-fit" method, the sequence of the variable domain of a non-human antibody is screened against the entire library of known human variable-domain sequences. The human sequence which is closest to that of that of the non-human parent antibody is then accepted as the human FR for the humanized antibody (Sims, et al., *J Immunol* 151:2296 (1993); Chothia, et al., *J Mol Biol* 196:901 (1987)). Another method uses a particular framework derived from the consensus sequence of all human antibodies of a particular subgroup of light or heavy chains. The same framework may be used for several different humanized antibodies (Carter, et al., *Proc Natl Acad Sci USA* 89:4285 (1992); Presta, et al., *J Immunol* 151:2623 (1993)).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of Cole, et al. and Boerder, et al. are also available for the preparation of human monoclonal antibodies (Cole, et al., Monoclonal Antibodies and Cancer Therapy, Alan R. Riss (1985); and Boerner, et al., *J Immunol* 147:86 (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. See, e.g., Jakobovitis, et al., *Proc Nat/ Acad Sci USA* 90:2551 (1993); Jakobovitis, et al., *Nature* 362:255 (1993); Bruggermann, et al., *Year in Immunol* 7:33 (1993); Duchosal, et al., *Nature* 355:258 (1992)). The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg, et al., *Int Rev Immunol* 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Also human MAbs could be made by immunizing mice transplanted with human peripheral blood leukocytes, splenocytes or bone marrows (e.g., Trioma techniques of XTL). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers, et al., *Bio/technology* 12:899 (1988)).

Further, antibodies to the polypeptides of the invention can, in turn, be utilized to generate anti-idiotype antibodies that "mimic" polypeptides of the invention using techniques well known to those skilled in the art (See, e.g., Greenspan, et al., *FASEB J* 7:437 (1989); Nissinoff, *J Immunol* 147:2429 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The antibodies of the present invention may be bispecific antibodies. Bispecific antibodies are monoclonal, preferably human or humanized, antibodies that have binding specificities for at least two different antigens. In the present invention, one of the binding specificities may be directed towards Notch3, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are well known. Traditionally, the recombinant production of bispecific antibodies is based on the co-expression of two immunoglobulin heavy-chain/light-chain pairs, where the two heavy chains have different specificities (Milstein, et al., *Nature* 305:537 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker, et al., *EMBO J* 10:3655 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It may have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh, et al., *Meth In Enzym* 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980). It is contemplated that the antibodies may be prepared in vitro using known methods in synthetic protein chemistry, including those involving cross-linking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

In addition, one can generate single-domain antibodies to Notch3. Examples of this technology have been described in WO9425591 for antibodies derived from Camelidae heavy chain Ig, as well in US20030130496 describing the isolation of single domain fully human antibodies from phage libraries.

One can also create a single peptide chain binding molecules in which the heavy and light chain Fv regions are connected. Single chain antibodies ("scFv") and the method of their construction are described in U.S. Pat. No. 4,946,778. Alternatively, Fab can be constructed and expressed by similar means. All of the wholly and partially human antibodies are less immunogenic than wholly murine MAbs, and the fragments and single chain antibodies are also less immunogenic.

Antibodies or antibody fragments can be isolated from antibody phage libraries generated using the techniques described in McCafferty, et al., *Nature* 348:552 (1990). Clarkson, et al., *Nature* 352:624 (1991) and Marks, et al., *J Mol Biol* 222:581 (1991) describe the isolation of murine and human antibodies, respectively, using phage libraries. Subsequent publications describe the production of high affinity (nM range) human antibodies by chain shuffling (Marks, et al., *Bio/Technology* 10:779 (1992)), as well as combinatorial infection and in vivo recombination as a strategy for constructing very large phage libraries (Waterhouse, et al., *Nuc Acids Res* 21:2265 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc Natl Acad Sci USA* 81:6851 (1984)).

Another alternative is to use electrical fusion rather than chemical fusion to form hybridomas. This technique is well established. Instead of fusion, one can also transform a B cell to make it immortal using, for example, an Epstein Barr Virus, or a transforming gene. See, e.g., "Continuously Proliferating Human Cell Lines Synthesizing Antibody of Predetermined Specificity," Zurawaki, et al., in Monoclonal Antibodies, ed. by Kennett, et al., Plenum Press, pp. 19-33. (1980)). Anti-Notch3 MAbs can be raised by immunizing rodents (e.g., mice, rats, hamsters, and guinea pigs) with Notch3 protein, fusion protein, or its fragments expressed by either eukaryotic or prokaryotic systems. Other animals can be used for immunization, e.g., non-human primates, transgenic mice expression immunoglobulins, and severe combined immunodeficient (SCID) mice transplanted with human B lymphocytes. Hybridomas can be generated by conventional procedures by fusing B lymphocytes from the immunized animals with myeloma cells (e.g., Sp2/0 and NS0), as described earlier (Kohler, et al., *Nature* 256:495 (1975)). In addition, anti-Notch3 antibodies can be generated by screening of recombinant single-chain Fv or Fab libraries from human B lymphocytes in phage-display systems. The specificity of the MAbs to Notch3 can be tested by ELISA, Western immunoblotting, or other immunochemical techniques. The inhibitory activity of the antibodies on complement activation can be assessed by hemolytic assays, using sensitized chicken or sheep RBCs for the classical complement pathway. The hybridomas in the positive wells are cloned by limiting dilution. The antibodies are purified for characterization for specificity to human Notch3 by the assays described above.

Identification of Anti-Notch-3 Antibodies

The present invention provides agonist monoclonal antibodies that activate Notch3-mediated signaling independent of ligand. In particular, the antibodies of the present invention bind to and activate Notch3. The antibodies of the present invention include the antibody designated 256A-13. The present invention also includes antibodies that bind to the same epitope as 256A-13.

Candidate anti-Notch3 antibodies were tested by enzyme linked immunosorbent assay (ELISA), Western immunoblotting, or other immunochemical techniques. Assays performed to characterize the individual antibodies are described in the Examples.

Antibodies of the invention include, but are not limited to, polyclonal, monoclonal, monovalent, bispecific, heteroconjugate, multispecific, human, humanized or chimeric antibodies, single chain antibodies, single-domain antibodies, Fab fragments, F(ab') fragments, fragments produced by a Fab expression library, anti-idiotypic (anti-id) antibodies (including, e.g., anti-id antibodies to antibodies of the invention), and epitope-binding fragments of any of the above.

The antibodies may be human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and single-domain antibodies comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments comprising any combination of variable region(s) with a hinge region, CH1, CH2, and CH3 domains. The antibodies of the invention may be from any animal origin including birds and mammals. Preferably, the antibodies are from human, non-human primates, rodents (e.g., mouse and rat), donkey, sheep, rabbit, goat, guinea pig, camel, horse, or chicken.

As used herein, "human" antibodies" include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati, et al. The antibodies of the present invention may be monospecific, bispecific, trispecific or of greater multispecificity. Multispecific antibodies may be specific for different epitopes of Notch3 or may be specific for both Notch3 as well as for a heterologous epitope, such as a heterologous polypeptide or solid support material. See, e.g., PCT publications WO 93/17715; WO 92/08802; WO 91/00360; WO 92/05793; Tutt, et al., *J Immunol* 147:60 (1991); U.S. Pat. Nos. 4,474,893; 4,714,681; 4,925,648; 5,573,920; 5,601,819; Kostelny, et al., *J Immunol* 148:1547 (1992).

Antibodies of the present invention may be described or specified in terms of the epitope(s) or portion(s) of Notch3 which they recognize or specifically bind. The epitope(s) or polypeptide portion(s) may be specified as described herein, e.g., by N-terminal and C-terminal positions, by size in contiguous amino acid residues, or listed in the Tables and Figures.

Antibodies of the present invention may also be described or specified in terms of their cross-reactivity. Antibodies that bind Notch3 polypeptides, which have at least 95%, at least 90%, at least 85%, at least 80%, at least 75%, at least 70%, at least 65%, at least 60%, at least 55%, and at least 50% identity (as calculated using methods known in the art and described herein) to Notch3 are also included in the present invention. Anti-Notch3 antibodies may also bind with a $K_D$ of less than about $10^{-7}$ M, less than about $10^{-6}$ M, or less than about $10^{-5}$ M to other proteins, such as anti-Notch3 antibodies from species other than that against which the anti-Notch3 antibody is directed.

In specific embodiments, antibodies of the present invention cross-react with monkey homologues of human Notch3 and the corresponding epitopes thereof. In a specific embodiment, the above-described cross-reactivity is with respect to any single specific antigenic or immunogenic polypeptide, or combination(s) of the specific antigenic and/or immunogenic polypeptides disclosed herein.

Further included in the present invention are antibodies which bind polypeptides encoded by polynucleotides which hybridize to a polynucleotide encoding Notch3 under stringent hybridization conditions. Antibodies of the present invention may also be described or specified in terms of their binding affinity to a polypeptide of the invention. Preferred binding affinities include those with an equilibrium dissociation constant or $K_D$ from $10^{-8}$ to $10^{-15}$ M, $10^{-8}$ to $10^{-12}$ M, $10^{-8}$ to $10^{-10}$ M, or $10^{-10}$ to $10^{-12}$ M. The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Vectors and Host Cells

In another aspect, the present invention provides isolated nucleic acid sequences encoding an antibody variant as disclosed herein, vector constructs comprising a nucleotide sequence encoding the antibodies of the present invention, host cells comprising such a vector, and recombinant techniques for the production of the antibody.

For recombinant production of the antibody variant, the nucleic acid encoding it is isolated and inserted into a replicable vector for further cloning (amplification of the DNA) or for expression. DNA encoding the antibody variant is readily isolated and sequenced using conventional procedures (e.g., by using oligonucleotide probes that are capable of binding specifically to genes encoding the heavy and light chains of the antibody variant). Standard techniques for cloning and transformation may be used in the preparation of cell lines expressing the antibodies of the present invention.

Vectors

Many vectors are available. The vector components generally include, but are not limited to, one or more of the following: a signal sequence, an origin of replication, one or more marker genes, an enhancer element, a promoter, and a transcription termination sequence. Recombinant expression vectors containing a nucleotide sequence encoding the antibodies of the present invention can be prepared using well known techniques. The expression vectors include a nucleotide sequence operably linked to suitable transcriptional or translational regulatory nucleotide sequences such as those derived from mammalian, microbial, viral, or insect genes. Examples of regulatory sequences include transcriptional promoters, operators, enhancers, mRNA ribosomal binding sites, and/or other appropriate sequences which control transcription and translation initiation and termination. Nucleotide sequences are "operably linked" when the regulatory sequence functionally relates to the nucleotide sequence for the appropriate polypeptide. Thus, a promoter nucleotide sequence is operably linked to, e.g., the antibody heavy chain sequence if the promoter nucleotide sequence controls the transcription of the appropriate nucleotide sequence.

In addition, sequences encoding appropriate signal peptides that are not naturally associated with antibody heavy and/or light chain sequences can be incorporated into expression vectors. For example, a nucleotide sequence for a signal peptide (secretory leader) may be fused in-frame to the polypeptide sequence so that the antibody is secreted to the periplasmic space or into the medium. A signal peptide that is functional in the intended host cells enhances extracellular secretion of the appropriate antibody. The signal peptide may be cleaved from the polypeptide upon secretion of antibody from the cell. Examples of such secretory signals are well known and include, e.g., those described in U.S. Pat. Nos. 5,698,435; 5,698,417; and 6,204,023.

The vector may be a plasmid vector, a single or double-stranded phage vector, or a single or double-stranded RNA or DNA viral vector. Such vectors may be introduced into cells as polynucleotides by well known techniques for introducing DNA and RNA into cells. The vectors, in the case of phage and viral vectors also may be introduced into cells as packaged or encapsulated virus by well known techniques for infection and transduction. Viral vectors may be replication competent or replication defective. In the latter case, viral propagation generally will occur only in complementing host cells. Cell-free translation systems may also be employed to produce the protein using RNAs derived from the present DNA constructs. Such vectors may include the nucleotide sequence encoding the constant region of the antibody molecule (see, e.g., PCT Publications WO 86/05807 and WO 89/01036; and U.S. Pat. No. 5,122,464) and the variable domain of the antibody may be cloned into such a vector for expression of the entire heavy or light chain.

Host Cells

The antibodies of the present invention can be expressed from any suitable host cell. Examples of host cells useful in the present invention include prokaryotic, yeast, or higher eukaryotic cells and include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., Baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

Prokaryotes useful as host cells in the present invention include gram negative or gram positive organisms such as *E. coli, B. subtilis, Enterobacter, Erwinia, Klebsiella, Proteus, Salmonella, Serratia*, and *Shigella*, as well as *Bacilli, Pseudomonas*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the pKK223-3 vector (Pharmacia Fine Chemicals, Uppsala, Sweden), PGEM®1 vector (Promega Biotec, Madison, Wis., USA), and the pET (Novagen, Madison, Wis., USA) and pRSET (Invitrogen, Carlsbad, Calif.) series of vectors (Studier, *J Mol Biol* 219:37 (1991); Schoepfer, *Gene* 124:83 (1993)). Promoter sequences commonly used for recombinant prokaryotic host cell expression vectors include T7, (Rosenberg, et al., *Gene* 56:125 (1987)), β-lactamase (penicillinase), lactose promoter system (Chang, et al., *Nature* 275:615 (1978); Goeddel, et al., *Nature* 281:544 (1979)), tryptophan (trp) promoter system (Goeddel, et al., *Nucl Acids Res* 8:4057 (1980)), and tac promoter (Sambrook, et al., Molecular Cloning, A Laboratory Manual, 2nd ed., Cold Spring Harbor Laboratory (1990)).

Yeasts or filamentous fungi useful in the present invention include those from the genus *Saccharomyces, Pichia, Actinomycetes, Kluyveromyces, Schizosaccharomyces, Candida, Trichoderma, Neurospora*, and filamentous fungi such as *Neurospora, Penicillium, Tolypocladium*, and *Aspergillus*. Yeast vectors will often contain an origin of replication sequence from a 2µ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman, et al., *J Biol Chem* 255:2073 (1980)) or other glycolytic enzymes (Holland, et al., *Biochem* 17:4900 (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer, et al., *Gene* 107:285 (1991). Other suitable promoters and vectors for yeast and yeast transformation protocols are well known in the art. Yeast transformation protocols are well known. One such protocol is described by Hinnen, et al., *Proc Natl Acad Sci* 75:1929 (1978). The Hinnen protocol selects for Trp$^+$ transformants in a selective medium.

Mammalian or insect host cell culture systems may also be employed to express recombinant antibodies. In principle, any higher eukaryotic cell culture is workable, whether from vertebrate or invertebrate culture. Examples of invertebrate cells include plant and insect cells (Luckow, et al., *Bio/Technology* 6:47 (1988); Miller, et al., Genetics Engineering, Setlow, et al., eds. Vol. 8, pp. 277-9, Plenam Publishing (1986); Mseda, et al., *Nature* 315:592 (1985)). For example, Baculovirus systems may be used for production of heterologous proteins. In an insect system, -*Autographa californica* nuclear polyhedrosis virus (AcNPV) may be used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). Other hosts that have been identified include *Aedes, Drosophila melanogaster*, and *Bombyx mori*. A variety of viral strains for transfection are publicly available, e.g., the L-1 variant of AcNPV and the Bm-5 strain of *Bombyx mori* NPV, and such viruses may be used as the virus herein according to the present invention, particularly for transfection of *Spodoptera frugiperda* cells. Moreover, plant cells cultures of cotton, corn, potato, soybean, petunia, tomato, and tobacco and also be utilized as hosts.

Vertebrate cells, and propagation of vertebrate cells, in culture (tissue culture) has become a routine procedure. See Tissue Culture, Kruse, et al., eds., Academic Press (1973). Examples of useful mammalian host cell lines are monkey kidney; human embryonic kidney line; baby hamster kidney cells; Chinese hamster ovary cells/−DHFR (CHO, Urlaub, et al., *Proc Natl Acad Sci USA* 77:4216 (1980)); mouse sertoli cells; human cervical carcinoma cells (HELA); canine kidney cells; human lung cells; human liver cells; mouse mammary tumor; and NS0 cells.

Host cells are transformed with the above-described vectors for antibody production and cultured in conventional nutrient media modified as appropriate for inducing promoters, transcriptional and translational control sequences, selecting transformants, or amplifying the genes encoding the desired sequences. Commonly used promoter sequences and enhancer sequences are derived from polyoma virus, Adenovirus 2, Simian virus 40 (SV40), and human cytomegalovirus (CMV). DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are commercially available.

The host cells used to produce the antibody variant of this invention may be cultured in a variety of media. Commercially available media such as Ham's F10 (Sigma, St Louis, Mo.), Minimal Essential Medium (MEM, Sigma, St Louis, Mo.), RPMI-1640 (Sigma, St Louis, Mo.), and Dulbecco's Modified Eagle's Medium (DMEM, Sigma, St Louis, Mo.) are suitable for culturing host cells. In addition, any of the media described in Ham, et al., *Meth Enzymol* 58:44 (1979), Barnes, et al., *Anal Biochem* 102:255 (1980), and U.S. Pat. No. 4,767,704; 4,657,866; 4,560,655; 5,122,469; 5,712,163; or 6,048,728 may be used as culture media for the host cells. Any of these media may be supplemented as necessary with hormones and/or other growth factors (such as insulin, transferrin, or epidermal growth factor), salts (such as X-chlorides, where X is sodium, calcium, magnesium; and phosphates), buffers (such as HEPES), nucleotides (such as adenosine and thymidine), antibiotics (such as qentamicin), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Polynucleotides Encoding Antibodies

The invention further provides polynucleotides or nucleic acids, e.g., DNA, comprising a nucleotide sequence encoding an antibody of the invention and fragments thereof. Exemplary polynucleotides include those encoding antibody chains comprising one or more of the amino acid sequences described herein. The invention also encompasses polynucleotides that hybridize under stringent or lower stringency hybridization conditions to polynucleotides that encode an antibody of the present invention.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier, et al., *Bio/Techniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook, et al., *Molecular Cloning, A Laboratory Manual*, 2nd ed., Cold Spring Harbor Laboratory (1990); Ausubel, et al., eds., *Current Protocols in Molecular Biology*, John Wiley & Sons (1998), which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the CDRs by well known methods, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia, et al., *J Mol Biol* 278: 457 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison, et al., *Proc Natl Acad Sci* 81:851 (1984); Neuberger, et al., *Nature* 312:604 (1984); Takeda, et al., *Nature* 314:452 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine MAb and a human immunoglobulin constant region, e.g., humanized antibodies.

Alternatively, techniques described for the production of single chain antibodies (U.S. Pat. No. 4,946,778; Bird, *Science* 242:423 (1988); Huston, et al., *Proc Natl Acad Sci USA* 85:5879 (1988); and Ward, et al., *Nature* 334:544 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra, et al., *Science* 242:1038 (1988)).

Methods of Producing Anti-Notch3 Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative, or analog thereof, (e.g., a heavy or light chain of an antibody of the invention or a single chain antibody of the invention), requires construction of an expression vector containing a polynucleotide that encodes the antibody or a fragment of the antibody. Once a polynucleotide encoding an antibody molecule has been obtained, the vector for the production of the antibody may be produced by recombinant DNA technology. An expression vector is constructed containing antibody coding sequences and appropriate transcriptional and translational control signals. These methods include, for example, in vitro recombinant DNA techniques, synthetic techniques, and in vivo genetic recombination.

The expression vector is transferred to a host cell by conventional techniques and the transfected cells are then cultured by conventional techniques to produce an antibody of the invention. In one aspect of the invention, vectors encoding both the heavy and light chains may be co-expressed in the host cell for expression of the entire immunoglobulin molecule, as detailed below.

A variety of host-expression vector systems may be utilized to express the antibody molecules of the invention as described above. Such host-expression systems represent vehicles by which the coding sequences of interest may be produced and subsequently purified, but also represent cells which may, when transformed or transfected with the appropriate nucleotide coding sequences, express an antibody molecule of the invention in situ. Bacterial cells such as *E. coli*, and eukaryotic cells are commonly used for the expression of a recombinant antibody molecule, especially for the expression of whole recombinant antibody molecule. For example, mammalian cells such as CHO, in conjunction with a vector such as the major intermediate early gene promoter element from human cytomegalovirus, are an effective expression system for antibodies (Foecking, et al., *Gene* 45:101 (1986); Cockett, et al., *Bio/Technology* 8:2 (1990)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, COS, 293, 3T3, or myeloma cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for one to two days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler, et al., *Cell* 11:223 (1977)), hypoxanthine-guanine phosphoribosyltransferase (Szybalska, et al., *Proc Natl Acad Sci USA* 48:202 (1992)), and adenine phosphoribosyltransferase (Lowy, et al., *Cell* 22:817 (1980)) genes can be employed in tk, hgprt or aprt-cells, respectively. Also, antimetabolite resistance can be used as the basis of selection for the following genes: dhfr, which confers resistance to methotrexate (Wigler, et al., *Proc Natl Acad Sci USA* 77:357 (1980); O'Hare, et al., *Proc Natl Acad Sci USA* 78:1527 (1981)); gpt, which confers resistance to mycophenolic acid (Mulligan, et al., *Proc Natl Acad Sci USA* 78:2072 (1981)); neo, which confers resistance to the aminoglycoside G-418 (Wu, et al., *Biotherapy* 3:87 (1991)); and hygro, which confers resistance to hygromycin (Santerre, et al., *Gene* 30:147 (1984)). Methods commonly known in the art of recombinant DNA technology may be routinely applied to select the desired recombinant clone, and such methods are described, for example, in Ausubel, et al., eds., Current Protocols in Molecular Biology, John Wiley & Sons (1993); Kriegler, Gene Transfer and Expression, A Laboratory Manual, Stockton Press (1990); and in Chapters 12 and 13, Dracopoli, et al., eds, Current Protocols in Human Genetics, John Wiley & Sons (1994); Colberre-Garapin, et al., *J Mol Biol* 150:1 (1981), which are incorporated by reference herein in their entireties.

The expression levels of an antibody molecule can be increased by vector amplification (for a review, see Bebbington, et al., "The use of vectors based on gene amplification for the expression of cloned genes in mammalian cells," DNA Cloning, Vol. 3. Academic Press (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse, et al., *Mol Cell Biol* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature* 322:52 (1986); Kohler, *Proc Natl Acad Sci USA* 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and size-exclusion chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide. Fused or conjugated antibodies of the present invention may be used for ease in purification. See e.g., PCT publication WO 93/21232; EP 439,095; Naramura, et al., *Immunol Lett* 39:91 (1994); U.S. Pat. No. 5,474,981; Gillies, et al., *Proc*

*Natl Acad Sci USA* 89:1428 (1992); Fell, et al., *J Immunol* 146:2446 (1991), which are incorporated by reference in their entireties.

Moreover, the antibodies or fragments thereof of the present invention can be fused to marker sequences, such as a peptide to facilitate purification. In preferred embodiments, the marker amino acid sequence is a hexa-histidine peptide (SEQ ID NO: 38), such as the tag provided in a pQE vector (QIAGEN, Inc., Chatsworth, Calif.), among others, many of which are commercially available. As described in Gentz, et al., *Proc Natl Acad Sci USA* 86:821 (1989), for instance, hexa-histidine (SEQ ID NO: 38) provides for convenient purification of the fusion protein. Other peptide tags useful for purification include, but are not limited to, the "HA" tag, which corresponds to an epitope derived from the influenza hemagglutinin protein (Wilson, et al., Cell 37:767 (1984)) and the "flag" tag.

Antibody Purification

When using recombinant techniques, the antibody variant can be produced intracellularly, in the periplasmic space, or directly secreted into the medium. If the antibody variant is produced intracellularly, as a first step, the particulate debris, either host cells or lysed fragments, may be removed, for example, by centrifugation or ultrafiltration. Carter, et al., *Bio/Technology* 10:163 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody variant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel elecrophoresis, dialysis, and affinity chromatography, with affinity chromatography being the preferred purification technique. The suitability of protein A as an affinity ligand depends on the species and isotype of any immunoglobulin Fc domain that is present in the antibody variant. Protein A can be used to purify antibodies that are based on human IgG1, IgG2 or IgG4 heavy chains (Lindmark, et al., *J Immunol Meth* 62:1 (1983)). Protein G is recommended for all mouse isotypes and for human IgG3 (Guss, et al., *EMBO J.* 5:1567 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody variant comprises a CH3 domain, the Bakerbond ABX™ resin (J. T. Baker; Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE® chromatography on an anion or cation exchange resin (such as a polyaspartic acid column), chromatofocusing, SDS-PAGE, and ammonium sulfate precipitation are also available depending on the antibody variant to be recovered.

Following any preliminary purification step(s), the mixture comprising the antibody variant of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulation

Therapeutic formulations of the polypeptide or antibody may be prepared for storage as lyophilized formulations or aqueous solutions by mixing the polypeptide having the desired degree of purity with optional "pharmaceutically-acceptable" carriers, excipients or stabilizers typically employed in the art (all of which are termed "excipients"), i.e., buffering agents, stabilizing agents, preservatives, isotonifiers, non-ionic detergents, antioxidants, and other miscellaneous additives. See Remington's Pharmaceutical Sciences, 16th edition, Osol, Ed. (1980). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives may be added to retard microbial growth, and may be added in amounts ranging from 0.2%-1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, and alkyl parabens such as methyl or propyl paraben, catechol, resorcinol, cyclohexanol, and 3-pentanol.

Isotonicifiers sometimes known as "stabilizers" may be added to ensure isotonicity of liquid compositions of the present invention and include polyhydric sugar alcohols, preferably trihydric or higher sugar alcohols, such as glycerin, erythritol, arabitol, xylitol, sorbitol and mannitol.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, alpha.-monothioglycerol and sodium thio sulfate; low molecular weight polypeptides (i.e. <10 residues); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers may be present in the range from 0.1 to 10,000 weights per part of weight active protein.

Non-ionic surfactants or detergents (also known as "wetting agents") may be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (TWEEN-20®, TWEEN-80®, etc.). Non-ionic surfactants may be present in a range of about 0.05 mg/ml to about 1.0 mg/ml, preferably about 0.07 mg/ml to about 0.2 mg/ml.

Additional miscellaneous excipients include bulking agents, (e.g., starch), chelating agents (e.g., EDTA), antioxidants (e.g., ascorbic acid, methionine, vitamin E), and cosolvents. The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended. The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin micropheres, microemulsions, nano-particles and nanocapsules) or in macroemulsions. Such techniques are disclosed in Remington's Pharmaceutical Sciences, 16th edition, Osal, Ed. (1980).

The formulations to be used for in vivo administration must be sterile. This is readily accomplished, for example, by filtration through sterile filtration membranes. Sustained-release preparations may be prepared. Suitable examples of sustained-release preparations include semi-permeable matrices of solid hydrophobic polymers containing the antibody variant, which matrices are in the form of shaped articles, e.g., films, or microcapsules. Examples of sustained-release matrices include polyesters, hydrogels (for example, poly(2-hydroxyethyl-methacrylate), poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The amount of therapeutic polypeptide, antibody, or fragment thereof which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans.

In a preferred embodiment, an aqueous solution of therapeutic polypeptide, antibody or fragment thereof is administered by subcutaneous injection. Each dose may range from about 0.5 μg to about 50 μg per kilogram of body weight, or more preferably, from about 3 μg to about 30 μg per kilogram body weight.

The dosing schedule for subcutaneous administration may vary form once a month to daily depending on a number of clinical factors, including the type of disease, severity of disease, and the subject's sensitivity to the therapeutic agent.
Therapeutic Uses of Anti-Notch-3 Antibodies It is contemplated that the antibodies of the present invention may be used to treat a mammal. In one embodiment, the antibody is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed on the mammal.

An antibody administered alone or in combination with factor(s) can be used as a therapeutic. The present invention is directed to antibody-based therapies which involve administering antibodies of the invention to an animal, a mammal, or a human, for treating a Notch3-mediated disease, disorder, or condition. The animal or subject may be a mammal in need of a particular treatment, such as a mammal having been diagnosed with a particular disorder, e.g., one relating to Notch3. Antibodies directed against Notch3 are useful against degenerative diseases and other Notch3-associated diseases including CADASIL, FHM, Alagille syndrome, neurological and degenerative disorders in mammals, including but not limited to cows, pigs, horses, chickens, cats, dogs, non-human primates etc., as well as humans. For example, by administering a therapeutically acceptable dose of an anti-Notch3 antibody, or antibodies, of the present invention, or a cocktail of the present antibodies, or in combination with other antibodies of varying sources, disease symptoms may be ameliorated or prevented in the treated mammal, particularly humans.

Therapeutic compounds of the invention include, but are not limited to, antibodies of the invention (including fragments, analogs and derivatives thereof as described herein) and nucleic acids encoding antibodies of the invention as described below (including fragments, analogs and derivatives thereof and anti-idiotypic antibodies as described herein). The antibodies of the invention can be used to treat, inhibit, or prevent diseases, disorders, or conditions associated with aberrant expression and/or activity of Notch3, including, but not limited to, any one or more of the diseases, disorders, or conditions described herein. The treatment and/or prevention of diseases, disorders, or conditions associated with aberrant expression and/or activity of Notch3 includes, but is not limited to, alleviating at least one symptom associated with those diseases, disorders, or conditions. Antibodies of the invention may be provided in pharmaceutically acceptable compositions as known in the art or as described herein.

Anti-Notch3 antibodies of the present invention may be used therapeutically in a variety of diseases. The present invention provides a method for preventing or treating Notch3-mediated diseases in a mammal. The method comprises administering a disease preventing or treating amount of anti-Notch3 antibody to the mammal. The anti-Notch3 antibody binds to Notch3 and agonizes its function. Notch3 signaling has been linked to various diseases such as CADASAL, FHM, familial paroxytic ataxia, Alagille syndrome, and other degenerative diseases and neurological disorders (Joutel, et al., *Nature* 383:707 (1996); Flynn, et al., *J Pathol* 204:55 (2004)). It is speculated that anti-Notch3 antibodies will also be effective to prevent the above mentioned diseases.

The amount of the antibody which will be effective in the treatment, inhibition, and prevention of a disease or disorder associated with aberrant expression and/or activity of Notch3 can be determined by standard clinical techniques. The dosage will depend on the type of disease to be treated, the severity and course of the disease, whether the antibody is administered for preventive or therapeutic purposes, previous therapy, the patient's clinical history and response to the antibody, and the discretion of the attending physician. The antibody can be administered in treatment regimes consistent with the disease, e.g., a single or a few doses over one to several days to ameliorate a disease state or periodic doses over an extended time to inhibit disease progression and prevent disease recurrence. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 150 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody variant composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody variant to be administered will be governed by such considerations, and is the minimum amount necessary to prevent, ameliorate, or treat a disease or disorder. The antibody variant need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages.

The antibodies of the invention may be administered alone or in combination with other types of treatments.

In a preferred aspect, the antibody is substantially purified (e.g., substantially free from substances that limit its effect or produce undesired side-effects).

Various delivery systems are known and can be used to administer an antibody of the present invention, including injection, e.g., encapsulation in liposomes, microparticles, microcapsules, recombinant cells capable of expressing the compound, receptor-mediated endocytosis (see, e.g., Wu, et al., *J Biol Chem* 262:4429 (1987)), construction of a nucleic acid as part of a retroviral or other vector, etc.

The anti-Notch3 antibody can be administered to the mammal in any acceptable manner. Methods of introduction include but are not limited to parenteral, subcutaneous, intraperitoneal, intrapulmonary, intranasal, epidural, inhalation, and oral routes, and if desired for immunosuppressive treatment, intralesional administration. Parenteral infusions include intramuscular, intradermal, intravenous, intraarterial, or intraperitoneal administration. The antibodies or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the therapeutic antibodies or compositions of the invention into the central nervous system by any suitable route, including intraventricular and intrathecal injection; intraventricular injection may be facilitated by an intraventricular catheter, for example, attached to a reservoir, such as an Ommaya reservoir. In addition, the antibody is suitably administered by pulse infusion, particularly with declining doses of the antibody. Preferably the dosing is given by injections, most preferably intravenous or subcutaneous injections, depending in part on whether the administration is brief or chronic.

Pulmonary administration can also be employed, e.g., by use of an inhaler or nebulizer, and formulation with an aerosolizing agent. The antibody may also be administered into the lungs of a patient in the form of a dry powder composition (See e.g., U.S. Pat. No. 6,514,496).

In a specific embodiment, it may be desirable to administer the therapeutic antibodies or compositions of the invention locally to the area in need of treatment; this may be achieved by, for example, and not by way of limitation, local infusion, topical application, by injection, by means of a catheter, by means of a suppository, or by means of an implant, said implant being of a porous, non-porous, or gelatinous material, including membranes, such as silastic membranes, or fibers.

Preferably, when administering an antibody of the invention, care must be taken to use materials to which the protein does not absorb.

In another embodiment, the antibody can be delivered in a vesicle, in particular a liposome (see Langer, *Science* 249: 1527 (1990); Treat, et al., in Liposomes in the Therapy of Infectious Disease and Cancer, Lopez-Berestein, et al., eds., pp. 353-365 (1989); Lopez-Berestein, ibid., pp. 317-27; see generally ibid.).

In yet another embodiment, the antibody can be delivered in a controlled release system. In one embodiment, a pump may be used (see Langer, *Science* 249:1527 (1990); Sefton, *CRC Crit Ref Biomed Eng* 14:201 (1987); Buchwald, et al., *Surgery* 88:507 (1980); Saudek, et al., *N Engl J Med* 321:574 (1989)). In another embodiment, polymeric materials can be used (see Medical Applications of Controlled Release, Langer, et al., eds., CRC Press (1974); Controlled Drug Bioavailability, Drug Product Design and Performance, Smolen, et al., eds., Wiley (1984); Ranger, et al., *J Macromol Sci Rev Macromol Chem* 23:61 (1983); see also Levy, et al., *Science* 228:190 (1985); During, et al., *Ann Neurol* 25:351 (1989); Howard, et al., *J Neurosurg* 71:105 (1989)). In yet another embodiment, a controlled release system can be placed in proximity of the therapeutic target.

The present invention also provides pharmaceutical compositions. Such compositions comprise a therapeutically effective amount of the antibody and a physiologically acceptable carrier. In a specific embodiment, the term "physiologically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such physiological carriers can be sterile liquids, such as water and oils, including those of petroleum, animal, vegetable, or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable carriers are described in "Remington's Pharmaceutical Sciences" by E. W. Martin. Such compositions will contain an effective amount of the antibody, preferably in purified form, together with a suitable amount of carrier so as to provide the form for proper administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for preventing or treating the condition and may have a sterile access port (for example, the container may be an intravenous solution bag or a vial having a stopper pierceable by a hypodermic injection needle). The active agent in the composition is the antibody. The label on, or associated with, the container indicates that the composition is used for treating the condition of choice. The article of manufacture may further comprise a second container comprising a pharmaceutically acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

Antibody-Based Gene Therapy

In a another aspect of the invention, nucleic acids comprising sequences encoding antibodies or functional derivatives thereof, are administered to treat, inhibit or prevent a disease or disorder associated with aberrant expression and/or activity of Notch3, by way of gene therapy. Gene therapy refers to therapy performed by the administration to a subject of an expressed or expressible nucleic acid. In this embodiment of the invention, the nucleic acids produce their encoded protein that mediates a therapeutic effect. Any of the methods for gene therapy available can be used according to the present invention. Exemplary methods are described below.

For general reviews of the methods of gene therapy, see Goldspiel, et al., *Clinical Pharmacy* 12:488 (1993); Wu, et al., *Biotherapy* 3:87 (1991); Tolstoshev, *Ann Rev Pharmacol Toxicol* 32:573 (1993); Mulligan, *Science* 260:926 (1993); Morgan, et al., *Ann Rev Biochem* 62:191 (1993); May, *TIBTECH* 11:155 (1993).

In a one aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific.

In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller, et al., *Proc Natl Acad Sci USA* 86:8932 (1989); Zijlstra, et al., *Nature* 342:435 (1989)). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu, et al., *J Biol Chem* 262:4429 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller, et al., *Proc Natl Acad Sci USA* 86:8932 (1989); Zijlstra, et al., *Nature* 342:435 (1989)).

In a specific embodiment, viral vectors that contain nucleic acid sequences encoding an antibody of the invention are used. For example, a retroviral vector can be used (see Miller, et al., *Meth Enzymol* 217:581 (1993)). These retroviral vectors contain the components necessary for the correct packaging of the viral genome and integration into the host cell DNA. The nucleic acid sequences encoding the antibody to be used in gene therapy are cloned into one or more vectors, which facilitate the delivery of the gene into a patient. More detail about retroviral vectors can be found in Boesen, et al., *Biotherapy* 6:291 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes, et al., *J Clin Invest* 93:644 (1994); Kiem, et al., *Blood* 83:1467 (1994); Salmons, et al., *Human Gene Therapy* 4:129 (1993); and Grossman, et al., *Curr Opin Gen and Dev* 3:110 (1993).

Adenoviruses may also be used in the present invention. Adenoviruses are especially attractive vehicles in the present invention for delivering antibodies to respiratory epithelia. Adenoviruses naturally infect respiratory epithelia. Other targets for adenovirus-based delivery systems are liver, the central nervous system, endothelial cells, and muscle. Adenoviruses have the advantage of being capable of infecting non-dividing cells. Kozarsky, et al., *Curr Opin Gen Dev* 3:499 (1993) present a review of adenovirus-based gene therapy. Bout, et al., *Human Gene Therapy* 5:3 (1994) demonstrated the use of adenovirus vectors to transfer genes to the respiratory epithelia of rhesus monkeys. Other instances of the use of adenoviruses in gene therapy can be found in Rosenfeld, et al., *Science* 252:431 (1991); Rosenfeld, et al., *Cell* 68:143 (1992); Mastrangeli, et al., *J Clin Invest* 91:225 (1993); PCT Publication WO94/12649; Wang, et al., *Gene Therapy* 2:775 (1995). Adeno-associated virus (AAV) has also been proposed for use in gene therapy (Walsh, et al., *Proc Soc Exp Biol Med* 204:289 (1993); U.S. Pat. Nos. 5,436,146; 6,632,670; and 6,642,051).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler, et al., *Meth Enzymol* 217:599 (1993); Cohen, et al., *Meth Enzymol* 217:618 (1993); Cline, *Pharmac Ther* 29:69 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a one embodiment, the cell used for gene therapy is autologous to the patient. Nucleic acid sequences encoding an antibody of the present invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple, et al., *Cell* 71:973 (1992); Rheinwald, *Meth Cell Bio* 21A:229 (1980); Pittelkow, et al., *Mayo Clinic Proc* 61:771 (1986)).

EXAMPLES

Example 1

Generation of Immunogen: Notch3 Extracellular Domain-Fc Fusion Protein

Anti-Notch3 monoclonal antibodies that specifically bind to the LIN12/dimerization domain (herein after "LD") of human Notch3 were generated using a recombinant Notch3-Fc fusion protein as immunogen comprising Notch3 LD whose carboxy terminal end was fused to a gamma 1 Fc region. Specifically, the immunogen comprised amino acid residues 1378 to 1640 of Notch3 LD (See FIG. 1) and human γ1Fc fusion protein (Notch3 LD/Fc). A control antibody was generated using the Notch3 EGF repeat region from amino acid residue 43 to 1377 as immunogen.

Notch3 protein sequence was analyzed using an internet-based research software and service (Motif Search). Human liver and pancreatic RNAs (Ambion, Inc. Austin, Tex.) were used as templates to synthesize the first strand of cDNA using a standard commercially available cDNA synthesis kit. The cDNAs encoding the Notch 3 LD and the EGF repeat region were PCR-amplified in the presence of Betaine (1-2M) and DMSO (5%). The PCR-synthesized Notch3-LD DNA fragment (~0.8 kb) and Notch3-EGF repeat DNA fragment (~4 kb) were cloned into expression vectors comprising a His-γ1Fc in the commercially available vector pSec or in the commercially available vector pCD3.1, each bearing a different antibiotic marker. This cloning resulted in two expression plasmids, one expressing a Notch3-LD/Fc fusion protein and the other expressing a Notch3-EGF/Fc fusion protein.

To facilitate the plasmid construction and to enhance the expression of the various Notch 3 recombinant proteins, oligonucleotides corresponding to the leader peptide sequence comprising the first 135 base pairs of the Notch3 nucleic acid coding sequence were generated. These oligonucleotides contained some changes in the wobble coding positions to lower the GC content. All nucleotide sequence changes were silent, i.e., no amino acid sequence changes (FIGS. 8A and 8B). After annealing the oligonucleotides together, the engineered leader peptide coding sequence was linked to the rest of the coding sequence by PCR-SOE (Ho, et al., *Gene* 77:51 (1989); Horton, et al., *BioTechniques* 8:528 (1990)) (See FIG. 9). This leader peptide coding sequence was used in Notch3-LD/Fc and Notch3 expression constructs. Therefore, both of the Fc fusion proteins comprise a signal peptide linked to the N-terminus, and a human γ1Fc sequence fused to the C-terminus. The amino acid sequence of Notch3-LD, including the leader peptide, is shown in FIG. 8B and SEQ ID NO:6.

Expression of Notch3-EGF/Fc and Notch3-LD/Fc fusion proteins were verified by transient transfection of the Notch3 expression plasmids into 293T (ATCC Number CRL-11268, Manassas, Va.) and CHO cells (Invitrogen, Carlsbad, Calif.), respectively. Prior to transfection, cells were cultured in DMEM (Invitrogen, Carlsbad, Calif.) growth medium containing 10% fetal calf serum (FCS), 2 mM of glutamine, and 1× essential amino acid solution followed by seeding about 3-5×10$^5$ cells per well in 6-well plate and growing for approximately 24 hours. Three micrograms each of the Notch3 fusion protein expression plasmids were transfected into cells in each well using a LIPOFECTAMINE™2000 transfection system (Invitrogen, Carlsbad, Calif.) following the manufacturer's protocol. After transfection, the cells were cultured in fresh growth medium and cultured in a $CO_2$ incubator for approximately 40-48 hours before subjecting to Notch3 fusion protein expression analysis. Alternatively, after transfection, the cells were cultured in growth medium for 3-4 hours, then switched to DMEM medium containing 2% FCS and cultured for approximately 60-66 hours before drawing conditioned medium for secreted protein analysis.

Stable cell lines were generated for both Notch3-LD/Fc (His-Fcγ/pSec vector) and Notch3-EGF/Fc (His-Fcγ/pSec vector). Each plasmid was transfected into CHO cells. After transfection, the cells were cultured in DMEM growth medium overnight, then switched to growth medium with 800 μg/ml hygromycin and cultured at least two weeks until the cells not carrying Notch3 expression plasmid were eliminated by the antibiotics. Conditioned media from the stable cell lines were subjected to Western blot analysis.

Stable or transient transfected cells were assayed for expression and secretion of Notch3-LD/Fc or Notch3-EGF/Fc fusion protein. Transfected cells harvested from culture dishes were washed once with phosphate buffered saline (PBS) and resuspended in deionized water, mixed with an equal volume of 2× protein sample loading buffer (BioRad, Hercules, Calif.) and then heated at about 100° C. for 10 minutes. Secreted protein was analyzed using conditioned medium mixed with an equal volume of 2× protein sample loading buffer and heated at 100° C. for 10 minutes. The samples were separated using 4-15% gradient SDS-PAGE. The proteins were transferred from the gel to a PVDF membrane (BioRad, Hercules, Calif.), which was blocked in 5% non-fat dry milk in PBST (PBS with 0.05% TWEEN-20®) for at least one hour prior to transfer of protein.

Notch3-EGF/Fc and Notch3-LD/Fc fusion proteins were detected by incubating with γFc-specific, HRP-conjugated antibody (Sigma, St Louis, Mo.) in blocking buffer for one hour at room temperature. The membrane was washed three times in PBST and developed with a chemiluminescent substrate.

For Notch3 domain/Fc fusion protein purification, CHO stable cell lines as described above were cultured in DMEM with 2% FCS for up to 5 days. One liter of conditioned medium collected, and subjected to protein-A bead-packed column for affinity binding. The column was washed with PBS, and the bound proteins were eluted in 50 mM citrate buffer (pH 2.8), and the pH was brought to neutral by adding 1 M Tris-HCl buffer (pH 8). Purity of the protein was assessed by protein gel analysis using 4-15% gradient SDS-PAGE. Protein concentration was assayed using Coomassie blue reagent following the manufacturer's protocol (Pierce, Rockford, Ill.). Through this procedure, milligram quantities of Notch3-LD/Fc and Notch3-EGF/Fc protein were purified for immunization and ELISA binding assays.

Example 2

Generation of Anti-Notch3 MABs

Male A/J mice (Harlan, Houston, Tex.), 8-12 week old, were injected subcutaneously with 25 μg of Notch3-EGF/Fc or Notch3-LD/Fc in complete Freund's adjuvant (Difco Laboratories, Detroit, Mich.) in 200 μl of PBS. Two weeks after the injections and three days prior to sacrifice, the mice were again injected intraperitoneally with 25 μg of the same antigen in PBS. For each fusion, single cell suspensions were prepared from spleen of an immunized mouse and used for fusion with Sp2/0 myeloma cells; $5 \times 10^8$ of Sp2/0 and $5 \times 10^8$ of spleen cells were fused in a medium containing 50% polyethylene glycol (M.W. 1450) (Kodak, Rochester, N.Y.) and 5% dimethylsulfoxide (Sigma, St. Louis, Mo.). The cells were then adjusted to a concentration of $1.5 \times 10^5$ spleen cells per 200 µl of the suspension in Iscove medium (Invitrogen, Carlsbad, Calif.), supplemented with 10% fetal bovine serum, 100 units/ml of penicillin, 100 µg/ml of streptomycin, 0.1 µM hypoxanthine, 0.4 µM aminopterin, and 16 µM thymidine. Two hundred microliters of the cell suspension were added to each well of about sixty 96-well plates. After around ten days, culture supernatants were withdrawn for screening their antibody-binding activity using ELISA.

The 96-well flat bottom IMMULON® II microtest plates (Dynatech, Laboratories, Chantilly, Va.) were coated using 100 µl of Notch3-EGF/Fc or Notch3LD/Fc (0.1 µg/ml) in (PBS) containing 1× Phenol Red and 3-4 drops pHix/liter (Pierce, Rockford, Ill.) and incubated overnight at room temperature. After the coating solution was removed by flicking of the plate, 200 µl of blocking buffer containing 2% BSA in PBST containing 0.1% merthiolate was added to each well for one hour to block non-specific binding. The wells were then washed with PBST. Fifty microliters of culture supernatant from each fusion well was collected and mixed with 50 µl of blocking buffer and then added to the individual wells of the microtiter plates. After one hour of incubation, the wells were washed with PBST. The bound murine antibodies were then detected by reaction with horseradish peroxidase (HRP)-conjugated, Fc-specific goat anti-mouse IgG (Jackson ImmunoResearch Laboratories, West Grove, Pa.). HRP substrate solution containing 0.1% 3,3,5,5-tetramethyl benzidine and 0.0003% hydrogen peroxide was added to the wells for color development for 30 minutes. The reaction was terminated by the addition of 50 ml of 2 M $H_2SO_4$/well. The OD at 450 nm was read with an ELISA plate reader (Molecular Devices, Sunnyvale, Calif.).

Among 185 hybridomas isolated and analyzed, one hybridoma clone from mice immunized with Notch3-LD/Fc generated a Notch3 agonist antibody 256A-13 and this antibody was further characterized. An ELISA was performed using supernatant from the hybridoma clone producing MAbs 256A-13. The results showed strong binding activity to the purified Notch3 LD/FC fusion protein to which it was generated and did not bind to human Notch1-LD/Fc (LIN/dimerization domain fused to Fc region at the carboxyl terminus) or a control human Fc protein (data not shown) (Table 1).

TABLE 1

| ELISA OD readings of 256A-13 using hybridoma supernatant | | |
|---|---|---|
| Target protein | Notch3-LD/Fc | |
| Hybridoma supernatant | Control IgG1 MAb | 256A-13 |
| Mean | 0.019 | 2.828 |
| S.D. | 0.002 | 0.047 |

The positive hybridoma clone from this primary ELISA screening was further isolated by single colony-picking and a second ELISA assay as described above was done to verify specific binding to the chosen immunogen. The confirmed hybridoma clone was expanded in larger scale cultures. The monoclonal antibodies (MAbs) were purified from the medium of these large scale cultures using a protein A affinity column. The anti-Notch3 agonist MAbs were then characterized using cell-based binding assays, microscopy, Western blot, and FACS analysis.

Example 3

Cell-Based Binding Assays for Anti-Notch3 Mabs

The cell-based binding assays used to characterize the anti-Notch3 MAbs required cloning a full-length of human Notch3 open reading frame into a vector, in this case PCDNA™3.1/Hygro (Invitrogen, Carlsbad, Calif.). The Notch3-coding region was synthesized by RT-PCR using human liver tumor RNA (Ambion, Inc., Austin, Tex.) as a template. The final plasmid construct, Notch3/Hygro, expressed a full-length Notch3 protein as depicted in FIG. 1. A stable cell line expressing Notch3 was generated by transfection of Notch3/Hygro plasmid construct into 293T cells (ATCC No. CRL-11268) using a LIPOFECTAMINE™2000 kit following the same procedure as described in Example 1. After transfection, the cells were cultured in DMEM growth medium overnight, then reseeded in growth medium with 200 µg/ml hygromycin and cultured for 12-14 days. Well-isolated single colonies were picked and grown in separate wells until enough clonal cells were amplified. Stable 293T clones that were resistant to hygromycin selection and expressed high levels of Notch3 protein were identified by Western blot analysis, and by fluorescent electromicroscopy using polyclonal anti-Notch3 antibodies (R&D Systems, Minneapolis, Minn.).

A partial Notch3 expression plasmid containing only the Notch LIN12/dimerization (LD) domain and the transmembrane (TM) domain was also constructed by PCR and subcloned into PCDNA™3.1 vector.

Human Sup-T1 cell line (ATCC No. CRL-1942) naturally expressing Notch3 was also confirmed by Western blot. Sup-T1 cells were grown in RPMI1640 media containing 10% fetal calf serum, 2 mM of glutamine and 1× essential amino acid solution.

Cell-based antibody-binding was assessed using FMAT™ (fluorescence macro-confocal high-throughput screening) 8100 HTS System (Applied Biosystems, Foster City, Calif.) following the protocol provided by the manufacturer. Cell lines naturally expressing Notch3 or stably transfected with Notch3 expression constructs were seeded in 96-well plates. Alternatively, transiently transfected 293T or CHO cells were seeded in the 96-well plate. The cells were seeded at a density of 30,000-50,000 cells per well. After 20-24 hours, anti-Notch3 MAbs and 1×PBS reaction buffer were added to the wells and incubated for one hour at 37° C. Cy-5-conjugated anti-mouse IgG antibody was added in the wells after removal of primary antibodies.

Cell-based antibody-binding was also assessed by fluorescence-activated cell sorter (FACS) using internally generated 293T/Notch3-stable cell line and two cancer lines, human Sup-T1 and A2780 cell lines (UK ECACC No. Cat. No. 93112519), both naturally express Notch3 (data not shown). Cells were first incubated with anti-Notch3 MAbs in 1×PBS. After three washes, the cells were incubated with fluorescent molecule-conjugated secondary antibody. The cells were resuspended, fixed in 1×PBS with 0.1% paraformaldehyde, and analyzed by FACS (BD Sciences, Palo Alto, Calif.). The results indicated that 256A-13 binds to Notch3 receptor expressed either from recombinant plasmid constructs or as native protein in cultured cells (Table 2). Transiently transfected 293T cells containing a Notch3/Hygro plasmid were also stained with immunofluorescence as described above and observed by fluorescent microscopy.

TABLE 2

Binding activity of 256A-13 in cell-based FACS analysis shown as mean fluorescent intensity

|  | Control IgG1 | 256A-13 |
|---|---|---|
| Notch3/Hyg | 24.16 | 32.2 |
| Sup-T1 | 24.51 | 55.44 |

The cell-based FMAT and FACS analyses confirmed that MAbs 256A-13 indeed binds to the Notch3 receptor expressed either from recombinant plasmid constructs or as native protein in cultured cells (Table 2 and Table 3).

TABLE 3

Summary of anti-Notch3 MAbs binding activity in cell-based FMAT

| Antibody | Control IgG1 | 256A-13 |
|---|---|---|
| Notch3 (full-length) | no binding | weak binding |
| Notch3-LDTM | no binding | strong binding |

A positive binding signal was determined based on the FMAT™ system signal read-out that was significantly higher than that of the IgG1 control and other negative hybridoma clones (p>0.01). The IgG1 control binding read-out was considered background. 293T cells transiently transfected with Notch3/Hygro plasmid were also stained with immunofluorescence as described above and observed by fluorescent microscopy.

The binding affinity of MAb 256A-13 was analyzed by Biacore System (Biacore Inc., Piscataway, N.J.). The antibody was directly immobilized on a chip through amine coupling (immobilization level: 200 RU), and the Notch3-LD/Fc protein (antigen) was injected at 5 different concentrations (ranging from 37.5 to 120 nM with association time between 5-8 minutes, and dissociation time between 1 and 2 hours). The running buffer and the sample buffer are PBS contained 5 mM $Ca^{2+}$). The chip surface was regenerated with 10 mM glycine, pH2. The antibody was characterized in duplicate. Table 4 discloses the statistical mean, standard errors and Kinetic dissociation constant (KD) calculated. The antibody has a high affinity with a KD of 280 μM, and a slow off-rate. Both the standard errors and chi square are low with a good fit (dynamic curve not shown).

TABLE 4

Characterization of MAb 256A-13 binding affinity by Biacore

| Sample | KD [pM] | ka [$M-1s-1$] | SE (ka) | kd [$s-1$] | SE (kd) | $\chi 2$ |
|---|---|---|---|---|---|---|
| 256A-13 | 280 | 4.20e4 | 0.98 | 1.18e-5 | 1.02e-7 | 0.392 |

KD: 256A-13 and Notch3-LD/Fc dissociation constant. Ka: Rate of 256A-13 binding to Notch3-LD/Fc (or On-rate). Kd: Rate of 256A-13 dissociate from Notch3-LD/Fc (or Off-rate). SE: standard error.

Example 4

Western Blot Analysis of 256A-13 Binding Activity

Western blot was performed to assess the binding activity of 256A-13 to Notch3 receptor under denaturing conditions, as well as expression levels of Notch3 and other Notch-related proteins in human cell lines. Purified Notch3-LD/Fc fusion protein was combined with protein loading buffer. Protein samples were also prepared from the transiently or stably transfected cells described in Example 1, which were harvested from culture dishes, washed once with PBS, resuspended in total cellular protein extract buffer (Pierce, Rockford, Ill.), and heated at 100° C. for 10 minutes after adding equal volume of 2× protein sample loading buffer. All samples were separated by electrophoresis in a 4-15% gradient SDS-PAGE. The proteins were transferred from gel to PVDF membrane and 256A-13 was applied to the Western blot membrane as the primary detection antibody. An HRP-conjugated secondary antibody was used for detection and the signal generated using a chemiluminescent substrate as described above. Positive control antibodies against human Fc, V5 tag, Notch3 and Notch1 were purchased from (Invitrogen, R&D Systems, Santa Cruz Biotechnologies, and Orbigen).

Western blot analysis showed that MAb 256A-13 binds to Notch3-LD/Fc under denaturing condition, as well as native molecular conformation as observed in ELISA and FACS analysis.

Example 5

Assessing Functionality of 256A-13 by Luciferase Reporter Assay

A. Plasmid Constructs

The full length Notch3 expression construct described in Example 3 above was confirmed by sequencing, and is identical to the published sequence depicted in FIG. 1. The expression of Notch3 was verified by transient transfection and Western blot as described in Example 4.

To generate a luciferase reporter plasmid for Notch signaling, two complementary oligonucleotide primers containing tandem repeats of CBF1 binding motif were synthesized having the following sequences:

(SEQ ID NO 12)
5' GCTCGAGCTCGTGGGAAAATACCGTGGGAAAATGAACCGTGGGAAAAT

CTCGTGG (SEQ ID NO 13)
5' GCTCGAGATTTTCCCACGAGATTTTCCCACGGTTC

These two oligo primers were annealed at 65° C. in 100 mM of NaCl with each oligo at a concentration of 4 mM. After annealing to each other, the primers were extended by PCR. The PCR product was cloned into a commercially available vector. The insert was verified by sequencing, which contains four tandem repeats of CBF1 binding motif and two flanking Xho I sites. The insert was excised using Xho I and ligated downstream of the firefly luciferase reporter coding sequence. After luciferase reporter assay and sequencing analysis, plasmid clones with eight repeats of CBF1 binding motifs were selected and designated CBF1-Luc.

B. Stable Cell Line Generation

Two stable cell lines were generated for functional assays using human embryonic kidney cell lines (HEK293). One cell line contained the Notch3-expressing plasmid and CBF1-Luc reporter plasmid integrated into the nuclear genome. This cell line was generated by cotransfecting Notch3/hygromycin and CBF1-Luc plasmids into 293T cells using LIPO-FECTAMINE™ 2000 according to the manufacturer's protocol. Stable transfection cell clones were selected against 200 µg/ml hygromycin in DMEM growth medium, and screened by luciferase reporter assay and Western blot. A cell line with a relatively high level of Notch3 receptor expression (based on Western blot) and luciferase activity was selected for use in functional assays, and designated NC85.

C. Luciferase Reporter Assay with Notch3 Overexpressing Cells Alone

NC85 cells were cultured in the presence of MAb 256-A13 for 24 to 48 hours. The media was then removed by aspiration, cells were lysed in 1× Passive Lysis Buffer (E1501, Promega, Madison, Wis.) and luciferase activities were assayed using the Luciferase Assay System following manufacturer's protocol (E1501, Promega, Madison, Wis.) in TD-20/20 luminometer (Turner Designs Instrument, Sunnyvale, Calif.). As illustrated in FIG. 5, NC85 cells cultured in the presence of MAb 256-A13, the luciferase activity was increased almost 4 fold as compared to that with control antibody G3. The luciferase reporter assay demonstrated that MAb 256-A13 induced a dramatic increase in luciferase activity without ligand binding, while antagonist anti-Notch3 antibodies MAbs 256A-4 and 256A-8 did not (FIG. 5).

Example 8

Mapping the Binding Epitope of 256A-13

A. Epitope-Mapping Strategy and Rationale Using Notch3 Single Domain and Fc Fusion Protein Constructs Notch3 LIN12/heterodimerization domains, also called Notch3 LIN12-dimerization domain (Notch3-LD) consisted of three LIN12 domains, $1^{st}$ LIN12 (L1,), $2^{nd}$ L1N12 (L2) and $3^{rd}$ LIN12 (L3) (See FIG. 10). Five Notch3 single domain/Fc fusion protein expression constructs (FIG. 7) were generated, and a western blot was performed to assess which domain was sufficient for MAb 256A-13 binding. After transient transfection, the supernatants with secreted Notch3 single domain/Fc fusion proteins were analyzed by SDS-PAGE. The results showed that MAb 256A-13 only binds to Notch3-L1, and not to any other domains. ELISA experiments also showed that MAb 256A-13 has very strong binding to Notch3-L1 and weak binding to Notch3-L3, and not to other domains (Table 5).

TABLE 5

Suummary of Western blot results and ELISA Readings using MAb 256-13 against Notch3-domain/Fc fusion protein constructs

| | Western blot result | | ELISA OD reading | |
|---|---|---|---|---|
| MAb | 256A-13 | Anti-human Fc | 256A-13 | Anti-human Fc |
| Notch3-LD/Fc | positive band | positive band | 1.882 | 1.557 |
| Notch3-L1/Fc | positive band | positive band | 1.797 | 1.364 |
| Notch3-L2/Fc | no band | positive band | 0.015 | 1.337 |
| Notch3-L3/Fc | no band | positive band | 1.054 | 1.425 |
| Notch3-D1/Fc | no band | positive band | 0.015 | 1.608 |
| Notch3-D2/Fc | no band | positive band | 0.015 | 1.628 |

A. Identification of Binding Epitope(s) by Subdomain Swap

First, the agonist Notch3 MAb, 256A-13, binds to Notch3 LIN12/dimerization domain (LD), but not to the homologous human Notch1 LIN12/dimerization domain (Table 5) Second, the anti-Notch3 MAb binds to denatured Notch3 protein in Western blot as discussed in Example 4 and 8, indicating that 256A-13 binds to a single epitope or to discrete epitopes independent of each other. Third, Notch3 and Notch1 share approximately 55% amino acid sequence homology in LIN12/dimerization domain, therefore it was concluded that a subdomain swap between Notch3 and Notch1 within this region would not disrupt the protein conformation. Notch1-LD cDNA was PCR-amplified using standard PCR methods. The first strand cDNA template was synthesized from PA-1 cell total RNA (ATCC No. CRL-1572). The human IgG kappa chain leader peptide coding sequence was PCR-amplified, used as leader peptide to link to the 5' of Notch1-LD by PCR-SOE and subcloned in His-γ1Fc/pSec.

TABLE 6

ELISA OD readings of MAbs 256A-13 and control IgG1 binding to Notch3-LD/Fc or Notch1-LD/Fc

| | Notch1-LD/Fc | | Notch3-LD/Fc | |
|---|---|---|---|---|
| | Mean | S.D. | Mean | S.D. |
| 256A-13 | 0.094 | 0.007 | 4.000 | 0 |
| IgG1 control | 0.066 | 0.006 | 0.063 | 0.006 |

B. Generation of Subdomain Swap Fusion Protein Constructs

Based on the ELISA analysis results presented in Section A above, the target domain of the $1^{st}$ LIN12 domain, or L1 was further divided into three subdomains and individually swapped with the corresponding subdomain of Notch1-L1. The subdomain swap constructs were generated using PCR-SOE (Ho, et al., *Gene* 77:51 (1989); Horton, et al., *BioTechniques* 8:528 (1990)) as illustrated in FIGS. 9 and 10. PCR and PCR-SOE reactions were performed using PCR with 1M Betaine and 5% DMSO added to the reaction. The final PCR-SOE product was subcloned and verified by sequencing. The plasmid clone with the correct insert sequence was cleaved with Nhe I and Xho I to excise the insert, which was gel-purified and subcloned. The five Notch3/Notch1 subdomain swap constructs are illustrated in FIG. 7. To facilitate the epitope mapping, the human IgG kappa chain signaling peptide was used as leader peptide in the domain swap constructs. The amino acid sequences of the subdomain constructs are shown in FIG. 10.

C. Expression of Notch3/Notch1 Subdomain Swap Fusion Protein

Notch3/Notch1-LD domain swap plasmids were transiently transfected in CHO cells using LipoFectamine 2000. CHO cells were seeded in DMEM growth medium with 10% FCS at 0.8~1×10⁶ cells per well in 6-well plate, maintained in $CO_2$ incubator overnight before transfection. The cells were recovered after transfection in the growth medium for about 3 hours, then switched to DMEM with 2% FCS, and cultured for three days. The conditioned media were harvested and centrifuged at 3500 rpm for 10 minutes. The supernatant containing Notch3-LD domain swap protein secreted from CHO was collected and prepared for Western blot and ELISA binding analyses. ELISA showed that all the domain-swap fusion proteins were expressed and secreted in conditioned medium (Table 4), which was further confirmed by Western blot analysis (data not shown).

The ELISA readings used anti-human Fc antibody as detection antibody showing all the proteins were expressed in conditioned medium. Human IgG/Fc was used as a control. The starting point of human IgG/Fc coated in each well is 100 ng.

D. Epitope Binding Analysis Using ELISA

The 96-well flat bottom IMMULON® II microtest plates (Dynatech, Laboratories, Chantilly, Va.) were coated with anti-human Fc antibody (Jackson ImmunoResearch) by adding 100 μl of the antibody (0.1 μg/ml) in phosphate buffered saline (PBS) containing 1× Phenol Red and 3-4 drops pHix/liter (Pierce, Rockford, Ill.), and incubated overnight at room temperature. After the coating solution was removed by flicking of the plate, 200 μl of blocking buffer containing 2% BSA in PBST and 0.1% merthiolate was added to each well for one hour to block non-specific binding. The wells were then washed with PBST. Fifty microliters of the above conditioned medium from each transfection of Notch3/Notch1 domain swap construct were collected, mixed with 50 μl of blocking buffer, and added to the individual wells of the microtiter plates. After one hour of incubation, the Notch3/Notch1-LD domain swap protein was captured by the coated anti-Fc antibody, and the wells were washed with PBST. Anti-Notch3 MAbs and isotype-matched control MAbs were serially diluted in blocking buffer as above, and 50 μl of the diluted MAbs were added in each well to assess binding to the bound Notch3/Notch1 domain swap protein. Horseradish peroxidase (HRP)-conjugated, Fc-specific goat anti-mouse IgG was used for detection. HRP substrate solution containing 0.1% 3,3,5,5-tetramethyl benzidine and 0.0003% hydrogen peroxide was added to the wells for color development for 30 minutes. The reaction was terminated by addition of 50 ml of 2 M $H_2SO_4$/well. The OD at 450 nm was read with an ELISA reader. Subdomain swap constructs and clusters of mutations were similarly examined by ELISA analysis above.

ELISA binding experiments using MAb 256A-13 against the subdomain-swap proteins showed that the swap of the 1st subdomain in Notch3-L1 domain (L1) did not affect the binding, indicating that 256A-13 does not bind to this region. On the other hand, the swaps of the $2^{nd}$ and $3^{rd}$ subdomains in Notch3-L1 significantly reduced the binding. Therefore, those two subdomains contain the binding epitope(s) for MAb 256A-13. (FIG. 10). In contrast, isotype-matched negative control antibody, G3, does not bind to any of the domain swap fusion proteins in the ELISA assay (FIG. 10). It was concluded from the above experiments that the 1st LIN12 domain was required for MAb 256A-13 binding, and specifically within the $2^{nd}$ and $3^{rd}$ subdomain region.

To further map the specific epitope that MAb 256A-13 binds, the $2^{nd}$ and $3^{rd}$ subdomains of Notch3-L1 domain were further divided into five amino acids clusters, and swapped with the corresponding amino acid residues in Notch1 (FIG. 10). ELISA binding assay showed that the swap from DRE (Notch3 sequence) to SQL (Notch1 sequence) completely abolished the ELISA binding activity, indicating that only this epitope is required for MAb 256A-13 binding within Notch3-L1 domain.

Pinpoint analysis of amino acid residues required for MAb 256A-13 binding is done by using di-Alanine peptide scanning. The Alanine peptides cover the DRE epitope mapped by amino acid swap analysis. The peptide is synthesized as a spot cross-linked to nylon support membrane. Antibody blot binding is assessed by dot blot. MAb G3 is used as a control IgG1. The peptide sequences are presented in FIG. 11.

Example 9

Sequencing of Anti-Notch3 Mabs

Because antibody binding properties are fully-dependent on the variable regions of both heavy chain and light chain, the variable sequences of 256A-13 were subtyped and sequenced. The antibody IgG subtype was determined using an ISOSTRIP™ mouse monoclonal antibody isotyping kit (Roche Diagnostics, Indianapolis, Ind.). The results showed that 256A-13 has an $IgG_1$ heavy chain and a kappa light chain.

The variable region sequences of heavy chain and light chain were decoded through RT-PCR and cDNA cloning. Total RNAs from hybridoma clones 256A-13 were isolated using an RNeasy Mini kit following manufacturer's protocol (Qiagen Sciences, Valencia, Calif.). The first strand cDNA was synthesized using the RNA template and SUPERSCRIPT® III reverse transcriptase kit. The variable region of light chain and heavy chain cDNAs were PCR-amplified from the first strand cDNA using degenerative forward primers covering the 5'-end of mouse kappa chain coding region and a reverse primer matching the constant region at the juncture to the 3'-end of the variable region, or using degenerative forward primers covering the 5'-end of mouse heavy chain coding region and a constant region reverse primer in mouse heavy chain. The PCR product was cloned into a commercially available vector and sequenced by Lone Star Lab (Houston, Tex.). The nucleotide sequences were analyzed utilizing the DNASTAR® computer software program (DNASTAR, Inc., Madison, Wis.). Each anti-Notch3 MAb sequence was determined by sequences from multiple PCR clones derived from the same hybridoma clone.

Example 10

Impact of Notch3 Agonistic Antibodies on Metalloprotease Cleavage of Notch3

Notch receptor activation involves ligand induced metalloprotease cleavage at juxtamembrane site (S2) generating an extracellular subunit. This cleavage is an essential prerequisite to S3 cleavage to release the activated Notch intracellular region. To test whether the agonizing antibodies can induce ligand-independent sequential Notch activation events, including two proteolytic cleavages, 293T cells stably expressing a recombinant Notch3 receptor (NC85 cells) were treated with either G3 or 256-A13. The soluble extracellular subunits generated by proteolytic cleavage in the culture medium were detected by an ELISA assay using an antibody bound to a solid surface that recognizes the Notch3 cleavage product. As shown in FIG. 6, Notch3 agonistic MAb significantly increased the generation of soluble Notch3 extracellular subunits in the conditioned medium, whereas control antibody G3 did not.

Example 12

Assay for Notch3 Related Diseases

To identify other Notch3 related diseases, one can sequence the Notch3 gene from patient samples, or perform immunohistochemistry to check for the under-expression of Notch3 receptor using patient tissue. In addition, one can isolate and culture cells from a patient suspected of having a Notch3 associated disease and study the impact of an agonistic antibody of the present invention on Notch3 signaling.

Those skilled in the art will recognize, or be able to ascertain using no more than routine experimentation, many equivalents to the specific embodiments of the invention described herein. Such equivalents are intended to be encompassed by the following claims.

What is claimed is:

1. A monoclonal antibody that specifically binds to Notch 3 receptor, wherein the antibody specifically binds to an epitope in SEQ ID NO:10, and wherein the antibody activates Notch 3 receptor-mediated signaling through the Notch 3 receptor independent of ligand binding to the Notch 3 receptor.

2. The antibody of claim 1, wherein the antibody is an antigen-binding antibody fragment.

3. The antibody of claim 2, wherein the antibody is a single chain Fv.

4. The antibody of claim 1, which is a human, humanized, or chimeric antibody.

5. A monoclonal antibody that specifically binds to Notch 3 receptor, wherein the antibody specifically binds to an epitope in SEQ ID NO:11, and wherein the antibody activates Notch 3 receptor-mediated signaling through the Notch 3 receptor independent of ligand binding to the Notch 3 receptor.

6. The antibody of claim 5, which is an antigen-binding antibody fragment.

7. The antibody of claim 6, which is a single chain Fv.

8. The antibody of claim 5, which is a human, humanized, or chimeric antibody.

9. The monoclonal antibody of claim 1, wherein the antibody comprises a variable heavy (VH) chain region comprising CDR-H1 of SEQ ID NO:4, CDR-H2 of SEQ ID NO:5, and CDR-H3 of SEQ ID NO:6, and a variable light (VL) chain region comprising CDR-L1 of SEQ ID NO:7, CDR-L2 of SEQ ID NO:8, and CDR-L3 of SEQ ID NO:9.

10. The antibody of claim 9, wherein the VH chain region comprises SEQ ID NO:2, and the VL chain region comprises SEQ ID NO:3.

11. A humanized form of the antibody of claim 10, wherein the humanized form specifically binds to an epitope in SEQ ID NO:10.

12. The antibody of claim 1, further comprising a label.

13. The antibody of claim 5, further comprising a label.

14. A polypeptide comprising the amino acid sequence of the VH chain region of a monoclonal antibody that specifically binds to Notch 3 receptor, wherein the antibody specifically binds to an epitope in SEQ ID NO: 10 and activates Notch 3 receptor-mediated signaling through the Notch 3 receptor independent of ligand binding to the Notch 3 receptor.

15. The polypeptide of claim 14, wherein the VH chain region comprises CDR-H1 of SEQ ID NO: 4, CDR-H2 of SEQ ID NO: 5, and CDR-H3 of SEQ ID NO: 6.

16. The polypeptide of claim 15, wherein the VH chain region comprises SEQ ID NO: 2.

17. A polypeptide comprising the amino acid sequence of the VL chain region of a monoclonal antibody that specifically binds to Notch 3 receptor, wherein the antibody specifically binds to an epitope in SEQ ID NO: 10 and activates Notch 3 receptor-mediated signaling through the Notch 3 receptor independent of ligand binding to the Notch 3 receptor.

18. The polypeptide of claim 17, wherein the VL chain region comprises CDR-L1 of SEQ ID NO: 7, CDR-L2 of SEQ ID NO: 8, and CDR-L3 of SEQ ID NO: 9.

19. The polypeptide of claim 18, wherein the VL chain region comprises SEQ ID NO: 3.

* * * * *

SEQUENCE LISTING

<160> NUMBER OF SEQ ID NOS: 44

<210> SEQ ID NO 1
<211> LENGTH: 2321
<212> TYPE: PRT
<213> ORGANISM: Homo sapiens

<400> SEQUENCE: 1

```
Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
            20                  25                  30

Leu Ala Gly Pro Gly Ala Ala Ala Pro Pro Cys Leu Asp Gly Ser Pro
            35                  40                  45

Cys Ala Asn Gly Gly Arg Cys Thr Gln Leu Pro Ser Arg Glu Ala Ala
50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
            115                 120                 125

Ala His Gly Ala Arg Cys Ser Val Gly Pro Asp Gly Arg Phe Leu Cys
130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
            195                 200                 205

Gly Gly Thr Cys Arg Gln Ser Gly Asp Leu Thr Tyr Asp Cys Ala Cys
210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
            275                 280                 285

Gly Thr Cys Phe Asn Thr Leu Gly Gly His Ser Cys Val Cys Val Asn
290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
            355                 360                 365
```

-continued

```
Asn Pro Val Asn Gly Arg Ala Ile Cys Thr Cys Pro Pro Gly Phe Thr
    370                 375                 380
Gly Gly Ala Cys Asp Gln Asp Val Asp Glu Cys Ser Ile Gly Ala Asn
385                 390                 395                 400
Pro Cys Glu His Leu Gly Arg Cys Val Asn Thr Gln Gly Ser Phe Leu
                405                 410                 415
Cys Gln Cys Gly Arg Gly Tyr Thr Gly Pro Arg Cys Glu Thr Asp Val
            420                 425                 430
Asn Glu Cys Leu Ser Gly Pro Cys Arg Asn Gln Ala Thr Cys Leu Asp
                435                 440                 445
Arg Ile Gly Gln Phe Thr Cys Ile Cys Met Ala Gly Phe Thr Gly Thr
    450                 455                 460
Tyr Cys Glu Val Asp Ile Asp Glu Cys Gln Ser Ser Pro Cys Val Asn
465                 470                 475                 480
Gly Gly Val Cys Lys Asp Arg Val Asn Gly Phe Ser Cys Thr Cys Pro
                485                 490                 495
Ser Gly Phe Ser Gly Ser Thr Cys Gln Leu Asp Val Asp Glu Cys Ala
            500                 505                 510
Ser Thr Pro Cys Arg Asn Gly Ala Lys Cys Val Asp Gln Pro Asp Gly
                515                 520                 525
Tyr Glu Cys Arg Cys Ala Glu Gly Phe Glu Gly Thr Leu Cys Asp Arg
    530                 535                 540
Asn Val Asp Asp Cys Ser Pro Asp Pro Cys His His Gly Arg Cys Val
545                 550                 555                 560
Asp Gly Ile Ala Ser Phe Ser Cys Ala Cys Ala Pro Gly Tyr Thr Gly
                565                 570                 575
Thr Arg Cys Glu Ser Gln Val Asp Glu Cys Arg Ser Gln Pro Cys Arg
            580                 585                 590
His Gly Gly Lys Cys Leu Asp Leu Val Asp Lys Tyr Leu Cys Arg Cys
                595                 600                 605
Pro Ser Gly Thr Thr Gly Val Asn Cys Glu Val Asn Ile Asp Asp Cys
    610                 615                 620
Ala Ser Asn Pro Cys Thr Phe Gly Val Cys Arg Asp Gly Ile Asn Arg
625                 630                 635                 640
Tyr Asp Cys Val Cys Gln Pro Gly Phe Thr Gly Pro Leu Cys Asn Val
                645                 650                 655
Glu Ile Asn Glu Cys Ala Ser Ser Pro Cys Gly Glu Gly Gly Ser Cys
            660                 665                 670
Val Asp Gly Glu Asn Gly Phe Arg Cys Leu Cys Pro Pro Gly Ser Leu
                675                 680                 685
Pro Pro Leu Cys Leu Pro Pro Ser His Pro Cys Ala His Glu Pro Cys
    690                 695                 700
Ser His Gly Ile Cys Tyr Asp Ala Pro Gly Gly Phe Arg Cys Val Cys
705                 710                 715                 720
Glu Pro Gly Trp Ser Gly Pro Arg Cys Ser Gln Ser Leu Ala Arg Asp
                725                 730                 735
Ala Cys Glu Ser Gln Pro Cys Arg Ala Gly Gly Thr Cys Ser Ser Asp
            740                 745                 750
Gly Met Gly Phe His Cys Thr Cys Pro Pro Gly Val Gln Gly Arg Gln
                755                 760                 765
Cys Glu Leu Leu Ser Pro Cys Thr Pro Asn Pro Cys Glu His Gly Gly
    770                 775                 780
Arg Cys Glu Ser Ala Pro Gly Gln Leu Pro Val Cys Ser Cys Pro Gln
785                 790                 795                 800
```

```
Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
            835                 840                 845

Asp Ile Asn Asp Cys Asp Pro Asn Pro Cys Leu Asn Gly Gly Ser Cys
        850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
            915                 920                 925

Ser Pro Ser Ser Cys Phe Asn Gly Gly Thr Cys Val Asp Gly Val Asn
        930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                965                 970                 975

Cys Ser Ala Ala His Pro Gly Phe Arg Cys Thr Cys Leu Glu Ser Phe
            980                 985                 990

Thr Gly Pro Gln Cys Gln Thr Leu Val Asp Trp Cys Ser Arg Gln Pro
            995                 1000                1005

Cys Gln Asn Gly Gly Arg Cys Val Gln Thr Gly Ala Tyr Cys Leu
    1010                1015                1020

Cys Pro Pro Gly Trp Ser Gly Arg Leu Cys Asp Ile Arg Ser Leu
    1025                1030                1035

Pro Cys Arg Glu Ala Ala Ala Gln Ile Gly Val Arg Leu Glu Gln
    1040                1045                1050

Leu Cys Gln Ala Gly Gly Gln Cys Val Asp Glu Asp Ser Ser His
    1055                1060                1065

Tyr Cys Val Cys Pro Glu Gly Arg Thr Gly Ser His Cys Glu Gln
    1070                1075                1080

Glu Val Asp Pro Cys Leu Ala Gln Pro Cys Gln His Gly Gly Thr
    1085                1090                1095

Cys Arg Gly Tyr Met Gly Gly Tyr Met Cys Glu Cys Leu Pro Gly
    1100                1105                1110

Tyr Asn Gly Asp Asn Cys Glu Asp Asp Val Asp Glu Cys Ala Ser
    1115                1120                1125

Gln Pro Cys Gln His Gly Gly Ser Cys Ile Asp Leu Val Ala Arg
    1130                1135                1140

Tyr Leu Cys Ser Cys Pro Pro Gly Thr Leu Gly Val Leu Cys Glu
    1145                1150                1155

Ile Asn Glu Asp Asp Cys Gly Pro Gly Pro Pro Leu Asp Ser Gly
    1160                1165                1170

Pro Arg Cys Leu His Asn Gly Thr Cys Val Asp Leu Val Gly Gly
    1175                1180                1185

Phe Arg Cys Thr Cys Pro Pro Gly Tyr Thr Gly Leu Arg Cys Glu
    1190                1195                1200

Ala Asp Ile Asn Glu Cys Arg Ser Gly Ala Cys His Ala Ala His
    1205                1210                1215
```

-continued

```
Thr Arg Asp Cys Leu Gln Asp Pro Gly Gly Phe Arg Cys Leu
1220                1225                1230

Cys His Ala Gly Phe Ser Gly Pro Arg Cys Gln Thr Val Leu Ser
1235                1240                1245

Pro Cys Glu Ser Gln Pro Cys Gln His Gly Gly Gln Cys Arg Pro
1250                1255                1260

Ser Pro Gly Pro Gly Gly Leu Thr Phe Thr Cys His Cys Ala
1265                1270                1275

Gln Pro Phe Trp Gly Pro Arg Cys Glu Arg Val Ala Arg Ser Cys
1280                1285                1290

Arg Glu Leu Gln Cys Pro Val Gly Val Pro Cys Gln Gln Thr Pro
1295                1300                1305

Arg Gly Pro Arg Cys Ala Cys Pro Pro Gly Leu Ser Gly Pro Ser
1310                1315                1320

Cys Arg Ser Phe Pro Gly Ser Pro Pro Gly Ala Ser Asn Ala Ser
1325                1330                1335

Cys Ala Ala Ala Pro Cys Leu His Gly Gly Ser Cys Arg Pro Ala
1340                1345                1350

Pro Leu Ala Pro Phe Phe Arg Cys Ala Cys Ala Gln Gly Trp Thr
1355                1360                1365

Gly Pro Arg Cys Glu Ala Pro Ala Ala Ala Pro Glu Val Ser Glu
1370                1375                1380

Glu Pro Arg Cys Pro Arg Ala Ala Cys Gln Ala Lys Arg Gly Asp
1385                1390                1395

Gln Arg Cys Asp Arg Glu Cys Asn Ser Pro Gly Cys Gly Trp Asp
1400                1405                1410

Gly Gly Asp Cys Ser Leu Ser Val Gly Asp Pro Trp Arg Gln Cys
1415                1420                1425

Glu Ala Leu Gln Cys Trp Arg Leu Phe Asn Asn Ser Arg Cys Asp
1430                1435                1440

Pro Ala Cys Ser Ser Pro Ala Cys Leu Tyr Asp Asn Phe Asp Cys
1445                1450                1455

His Ala Gly Gly Arg Glu Arg Thr Cys Asn Pro Val Tyr Glu Lys
1460                1465                1470

Tyr Cys Ala Asp His Phe Ala Asp Gly Arg Cys Asp Gln Gly Cys
1475                1480                1485

Asn Thr Glu Glu Cys Gly Trp Asp Gly Leu Asp Cys Ala Ser Glu
1490                1495                1500

Val Pro Ala Leu Leu Ala Arg Gly Val Leu Val Leu Thr Val Leu
1505                1510                1515

Leu Pro Pro Glu Glu Leu Leu Arg Ser Ser Ala Asp Phe Leu Gln
1520                1525                1530

Arg Leu Ser Ala Ile Leu Arg Thr Ser Leu Arg Phe Arg Leu Asp
1535                1540                1545

Ala His Gly Gln Ala Met Val Phe Pro Tyr His Arg Pro Ser Pro
1550                1555                1560

Gly Ser Glu Pro Arg Ala Arg Arg Glu Leu Ala Pro Glu Val Ile
1565                1570                1575

Gly Ser Val Val Met Leu Glu Ile Asp Asn Arg Leu Cys Leu Gln
1580                1585                1590

Ser Pro Glu Asn Asp His Cys Phe Pro Asp Ala Gln Ser Ala Ala
1595                1600                1605

Asp Tyr Leu Gly Ala Leu Ser Ala Val Glu Arg Leu Asp Phe Pro
1610                1615                1620
```

-continued

Tyr Pro Leu Arg Asp Val Arg Gly Glu Pro Leu Glu Pro Pro Glu
1625                1630                1635

Pro Ser Val Pro Leu Leu Pro Leu Leu Val Ala Gly Ala Val Leu
1640                1645                1650

Leu Leu Val Ile Leu Val Leu Gly Val Met Val Ala Arg Arg Lys
1655                1660                1665

Arg Glu His Ser Thr Leu Trp Phe Pro Glu Gly Phe Ser Leu His
1670                1675                1680

Lys Asp Val Ala Ser Gly His Lys Gly Arg Arg Glu Pro Val Gly
1685                1690                1695

Gln Asp Ala Leu Gly Met Lys Asn Met Ala Lys Gly Glu Ser Leu
1700                1705                1710

Met Gly Glu Val Ala Thr Asp Trp Met Asp Thr Glu Cys Pro Glu
1715                1720                1725

Ala Lys Arg Leu Lys Val Glu Glu Pro Gly Met Gly Ala Glu Glu
1730                1735                1740

Ala Val Asp Cys Arg Gln Trp Thr Gln His His Leu Val Ala Ala
1745                1750                1755

Asp Ile Arg Val Ala Pro Ala Met Ala Leu Thr Pro Pro Gln Gly
1760                1765                1770

Asp Ala Asp Ala Asp Gly Met Asp Val Asn Val Arg Gly Pro Asp
1775                1780                1785

Gly Phe Thr Pro Leu Met Leu Ala Ser Phe Cys Gly Gly Ala Leu
1790                1795                1800

Glu Pro Met Pro Thr Glu Glu Asp Glu Ala Asp Thr Ser Ala
1805                1810                1815

Ser Ile Ile Ser Asp Leu Ile Cys Gln Gly Ala Gln Leu Gly Ala
1820                1825                1830

Arg Thr Asp Arg Thr Gly Glu Thr Ala Leu His Leu Ala Ala Arg
1835                1840                1845

Tyr Ala Arg Ala Asp Ala Ala Lys Arg Leu Leu Asp Ala Gly Ala
1850                1855                1860

Asp Thr Asn Ala Gln Asp His Ser Gly Arg Thr Pro Leu His Thr
1865                1870                1875

Ala Val Thr Ala Asp Ala Gln Gly Val Phe Gln Ile Leu Ile Arg
1880                1885                1890

Asn Arg Ser Thr Asp Leu Asp Ala Arg Met Ala Asp Gly Ser Thr
1895                1900                1905

Ala Leu Ile Leu Ala Ala Arg Leu Ala Val Glu Gly Met Val Glu
1910                1915                1920

Glu Leu Ile Ala Ser His Ala Asp Val Asn Ala Val Asp Glu Leu
1925                1930                1935

Gly Lys Ser Ala Leu His Trp Ala Ala Ala Val Asn Asn Val Glu
1940                1945                1950

Ala Thr Leu Ala Leu Leu Lys Asn Gly Ala Asn Lys Asp Met Gln
1955                1960                1965

Asp Ser Lys Glu Glu Thr Pro Leu Phe Leu Ala Ala Arg Glu Gly
1970                1975                1980

Ser Tyr Glu Ala Ala Lys Leu Leu Leu Asp His Phe Ala Asn Arg
1985                1990                1995

Glu Ile Thr Asp His Leu Asp Arg Leu Pro Arg Asp Val Ala Gln
2000                2005                2010

Glu Arg Leu His Gln Asp Ile Val Arg Leu Leu Asp Gln Pro Ser
2015                2020                2025

```
Gly Pro Arg Ser Pro Pro Gly Pro His Gly Leu Gly Pro Leu Leu
    2030                2035                2040

Cys Pro Pro Gly Ala Phe Leu Pro Gly Leu Lys Ala Ala Gln Ser
    2045                2050                2055

Gly Ser Lys Lys Ser Arg Arg Pro Pro Gly Lys Ala Gly Leu Gly
    2060                2065                2070

Pro Gln Gly Pro Arg Gly Arg Gly Lys Lys Leu Thr Leu Ala Cys
    2075                2080                2085

Pro Gly Pro Leu Ala Asp Ser Ser Val Thr Leu Ser Pro Val Asp
    2090                2095                2100

Ser Leu Asp Ser Pro Arg Pro Phe Gly Pro Pro Ala Ser Pro
    2105                2110                2115

Gly Gly Phe Pro Leu Glu Gly Pro Tyr Ala Ala Ala Thr Ala Thr
    2120                2125                2130

Ala Val Ser Leu Ala Gln Leu Gly Gly Pro Gly Arg Ala Gly Leu
    2135                2140                2145

Gly Arg Gln Pro Pro Gly Gly Cys Val Leu Ser Leu Gly Leu Leu
    2150                2155                2160

Asn Pro Val Ala Val Pro Leu Asp Trp Ala Arg Leu Pro Pro Pro
    2165                2170                2175

Ala Pro Pro Gly Pro Ser Phe Leu Leu Pro Leu Ala Pro Gly Pro
    2180                2185                2190

Gln Leu Leu Asn Pro Gly Thr Pro Val Ser Pro Gln Glu Arg Pro
    2195                2200                2205

Pro Pro Tyr Leu Ala Val Pro Gly His Gly Glu Glu Tyr Pro Val
    2210                2215                2220

Ala Gly Ala His Ser Ser Pro Pro Lys Ala Arg Phe Leu Arg Val
    2225                2230                2235

Pro Ser Glu His Pro Tyr Leu Thr Pro Ser Pro Glu Ser Pro Glu
    2240                2245                2250

His Trp Ala Ser Pro Ser Pro Pro Ser Leu Ser Asp Trp Ser Glu
    2255                2260                2265

Ser Thr Pro Ser Pro Ala Thr Ala Thr Gly Ala Met Ala Thr Thr
    2270                2275                2280

Thr Gly Ala Leu Pro Ala Gln Pro Leu Pro Leu Ser Val Pro Ser
    2285                2290                2295

Ser Leu Ala Gln Ala Gln Thr Gln Leu Gly Pro Gln Pro Glu Val
    2300                2305                2310

Thr Pro Lys Arg Gln Val Leu Ala
    2315                2320

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Gln Val Gln Leu Gln Gln Ser Gly Ala Glu Leu Ala Lys Pro Gly
1               5                   10                  15

Thr Ser Val Lys Met Ala Cys Lys Ala Ser Gly Tyr Thr Phe Thr Thr
            20                  25                  30

His Trp Met Asn Trp Val Lys Gln Arg Pro Gly Gln Gly Leu Glu Trp
        35                  40                  45
```

-continued

Ile Gly Thr Ile Asn Pro Ser Asn Asp Phe Thr Asp Cys Asn Gln Lys
50                  55                  60

Phe Lys Asp Lys Ala Ile Leu Thr Ala Asp Lys Ser Ser Ser Thr Ala
65                  70                  75                  80

Tyr Met Gln Leu Ser Ser Leu Thr Ser Glu Asp Ser Ala Ile Tyr Tyr
                85                  90                  95

Cys Ala Ser Gly Leu Thr Ala Arg Ala Trp Phe Ala Tyr Trp Gly Gln
                100                 105                 110

Gly Thr Leu Val Thr Val Ser Ala Ala
            115                 120

<210> SEQ ID NO 3
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Arg Ala Thr Ile Ser Cys Arg Ala Ser Gln Ser Val Thr Thr Ser Asn
1               5                   10                  15

Tyr Ser Tyr Met His Trp Phe Gln Gln Lys Pro Gly Gln Pro Pro Lys
                20                  25                  30

Leu Leu Ile Lys Tyr Ala Ser Asn Leu Asp Ser Gly Val Pro Ala Arg
            35                  40                  45

Phe Ser Gly Ser Gly Ser Gly Thr Asp Phe Thr Leu Asn Ile His Pro
    50                  55                  60

Val Glu Glu Glu Asp Thr Ala Thr Phe Tyr Cys Gln His Ser Trp Glu
65                  70                  75                  80

Ile Pro Tyr Thr Phe Gly Gly Gly Thr Asn Leu Glu Ile Lys Arg Ala
                85                  90                  95

Asp Ala Ala Pro Thr Val
            100

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Thr Phe Thr Thr His Trp Met Asn Trp
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Asn Pro Ser Asn Asp Phe Thr Asp Cys Asn
1               5                   10

<210> SEQ ID NO 6
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Thr Ala Arg Ala Trp Phe Ala Tyr
1               5

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Ser Gln Ser Val Thr Thr Ser Asn Tyr Ser Tyr Met His
1               5                   10                  15

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Ala Ser Asn Leu Asp Ser Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln His Ser Trp Glu Ile Pro Tyr Thr
1               5

<210> SEQ ID NO 10
<211> LENGTH: 39
<212> TYPE: PRT
<213> ORGANISM: Homo sapiens

<400> SEQUENCE: 10

Glu Pro Arg Cys Pro Arg Ala Ala Cys Gln Ala Lys Arg Gly Asp Gln
1               5                   10                  15

Arg Cys Asp Arg Glu Cys Asn Ser Pro Gly Cys Gly Trp Asp Gly Gly
            20                  25                  30

Asp Cys Ser Leu Ser Val Gly
                35

<210> SEQ ID NO 11
<211> LENGTH: 29
<212> TYPE: PRT
<213> ORGANISM: Homo sapiens
```

-continued

```
<400> SEQUENCE: 11

Ala Lys Arg Gly Asp Gln Arg Cys Asp Arg Glu Cys Asn Ser Pro Gly
1               5                   10                  15

Cys Gly Trp Asp Gly Gly Asp Cys Ser Leu Ser Val Gly
            20                  25

<210> SEQ ID NO 12
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gctcgagctc gtgggaaaat accgtgggaa aatgaaccgt gggaaaatct cgtgg           55

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctcgagatt ttcccacgag attttcccac ggttc                                35

<210> SEQ ID NO 14
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Glu Ala Cys Glu Leu Pro Glu Cys Gln Ala Lys Arg Gly Asp Gln
1               5                   10                  15

Arg Cys Asp Arg Glu Cys Asn Ser Pro Gly Cys Gly Trp Asp Gly Gly
            20                  25                  30

Asp Cys Ser Leu Ser Val Gly
        35

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Pro Arg Cys Pro Arg Ala Ala Cys Gln Glu Asp Ala Gly Asn Lys
1               5                   10                  15

Val Cys Ser Arg Glu Cys Asn Ser Pro Gly Cys Gly Trp Asp Gly Gly
            20                  25                  30

Asp Cys Ser Leu Ser Val Gly
        35

<210> SEQ ID NO 16
<211> LENGTH: 39
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 16

Glu Pro Arg Cys Pro Arg Ala Ala Cys Gln Ala Lys Arg Gly Asp Gln
1               5                   10                  15

Arg Cys Asp Leu Gln Cys Asn Asn His Ala Cys Gly Trp Asp Gly Gly
            20                  25                  30

Asp Cys Ser Leu Asn Phe Asn
        35

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Pro Arg Cys Pro Arg Ala Ala Cys Gln Glu Asp Ala Gly Asp Gln
1               5                   10                  15

Arg Cys Asp Arg Glu Cys Asn Ser Pro Gly Cys Gly Trp Asp Gly Gly
            20                  25                  30

Asp Cys Ser Leu Ser Val Gly
        35

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Pro Arg Cys Pro Arg Ala Ala Cys Gln Ala Lys Arg Gly Asn Lys
1               5                   10                  15

Val Cys Asp Arg Glu Cys Asn Ser Pro Gly Cys Gly Trp Asp Gly Gly
            20                  25                  30

Asp Cys Ser Leu Ser Val Gly
        35

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Pro Arg Cys Pro Arg Ala Ala Cys Gln Ala Lys Arg Gly Asp Gln
1               5                   10                  15

Arg Cys Ser Leu Gln Cys Asn Ser Pro Gly Cys Gly Trp Asp Gly Gly
            20                  25                  30

Asp Cys Ser Leu Ser Val Gly
        35

<210> SEQ ID NO 20
<211> LENGTH: 39
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 20

Glu Pro Arg Cys Pro Arg Ala Ala Cys Gln Ala Lys Arg Gly Asp Gln
1               5                   10                  15

Arg Cys Asp Arg Glu Cys Asn Asn His Ala Cys Gly Trp Asp Gly Gly
            20                  25                  30

Asp Cys Ser Leu Ser Val Gly
            35

<210> SEQ ID NO 21
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Pro Arg Cys Pro Arg Ala Ala Cys Gln Ala Lys Arg Gly Asp Gln
1               5                   10                  15

Arg Cys Asp Arg Glu Cys Asn Ser Pro Gly Cys Gly Trp Asp Gly Gly
            20                  25                  30

Asp Cys Ser Leu Asn Phe Asn
            35

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Cys Gln Ala Ala Ala Gly Asp Gln Arg Cys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Cys Gln Ala Lys Ala Ala Asp Gln Arg Cys Asp
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Gln Ala Lys Arg Ala Ala Gln Arg Cys Asp Arg
1               5                   10
```

```
<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ala Lys Arg Gly Ala Ala Arg Cys Asp Arg Glu
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Lys Arg Gly Asp Ala Ala Cys Asp Arg Glu Cys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Arg Gly Asp Gln Ala Ala Asp Arg Glu Cys Asn
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Gly Asp Gln Arg Ala Ala Arg Glu Cys Asn Ser
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Asp Gln Arg Cys Ala Ala Glu Cys Asn Ser Pro
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Asp Gln Arg Cys Asp Ala Ala Cys Asn Ser Pro Gly
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Arg Cys Asp Arg Ala Ala Asn Ser Pro Gly Cys
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Cys Asp Arg Glu Ala Ala Ser Pro Gly Cys Gly
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Asp Arg Glu Cys Ala Ala Pro Gly Cys Gly Trp
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Arg Glu Cys Asn Ala Ala Gly Cys Gly Trp Asp
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Glu Cys Asn Ser Ala Ala Cys Gly Trp Asp Gly
1               5                   10

<210> SEQ ID NO 36
<211> LENGTH: 12
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 36

Glu Cys Asn Ser Pro Ala Ala Gly Trp Asp Gly Gly
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Asn Ser Pro Gly Ala Ala Trp Asp Gly Gly Asp
1               5                   10

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 38

His His His His His His
1               5

<210> SEQ ID NO 39
<211> LENGTH: 2556
<212> TYPE: PRT
<213> ORGANISM: Homo sapiens

<400> SEQUENCE: 39

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

-continued

```
Gly Thr Cys His Asn Glu Val Gly Ser Tyr Arg Cys Val Cys Arg Ala
            195                 200                 205
Thr His Thr Gly Pro Asn Cys Glu Arg Pro Tyr Val Pro Cys Ser Pro
        210                 215                 220
Ser Pro Cys Gln Asn Gly Gly Thr Cys Arg Pro Thr Gly Asp Val Thr
225                 230                 235                 240
His Glu Cys Ala Cys Leu Pro Gly Phe Thr Gly Gln Asn Cys Glu Glu
                245                 250                 255
Asn Ile Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Trp Thr
        275                 280                 285
Gly Gln Tyr Cys Thr Glu Asp Val Asp Glu Cys Gln Leu Met Pro Asn
    290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe His Gly Ala Thr Cys His Asp
            340                 345                 350
Arg Val Ala Ser Phe Tyr Cys Glu Cys Pro His Gly Arg Thr Gly Leu
        355                 360                 365
Leu Cys His Leu Asn Asp Ala Cys Ile Ser Asn Pro Cys Asn Glu Gly
    370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
                405                 410                 415
Ser Leu Gly Ala Asn Pro Cys Glu His Ala Gly Lys Cys Ile Asn Thr
            420                 425                 430
Leu Gly Ser Phe Glu Cys Gln Cys Leu Gln Gly Tyr Thr Gly Pro Arg
        435                 440                 445
Cys Glu Ile Asp Val Asn Glu Cys Val Ser Asn Pro Cys Gln Asn Asp
    450                 455                 460
Ala Thr Cys Leu Asp Gln Ile Gly Glu Phe Gln Cys Ile Cys Met Pro
465                 470                 475                 480
Gly Tyr Glu Gly Val His Cys Glu Val Asn Thr Asp Glu Cys Ala Ser
                485                 490                 495
Ser Pro Cys Leu His Asn Gly Arg Cys Leu Asp Lys Ile Asn Glu Phe
            500                 505                 510
Gln Cys Glu Cys Pro Thr Gly Phe Thr Gly His Leu Cys Gln Tyr Asp
        515                 520                 525
Val Asp Glu Cys Ala Ser Thr Pro Cys Lys Asn Gly Ala Lys Cys Leu
    530                 535                 540
Asp Gly Pro Asn Thr Tyr Thr Cys Val Cys Thr Glu Gly Tyr Thr Gly
545                 550                 555                 560
Thr His Cys Glu Val Asp Ile Asp Glu Cys Asp Pro Asp Pro Cys His
                565                 570                 575
Tyr Gly Ser Cys Lys Asp Gly Val Ala Thr Phe Thr Cys Leu Cys Arg
            580                 585                 590
Pro Gly Tyr Thr Gly His His Cys Glu Thr Asn Ile Asn Glu Cys Ser
        595                 600                 605
Ser Gln Pro Cys Arg His Gly Gly Thr Cys Gln Asp Arg Asp Asn Ala
    610                 615                 620
```

-continued

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
            645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
            725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
            805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Trp Gln Ala Gly
    850                 855                 860

Gln Thr Cys Glu Val Asp Ile Asn Glu Cys Val Leu Ser Pro Cys Arg
865                 870                 875                 880

His Gly Ala Ser Cys Gln Asn Thr His Gly Gly Tyr Arg Cys His Cys
            885                 890                 895

Gln Ala Gly Tyr Ser Gly Arg Asn Cys Glu Thr Asp Ile Asp Asp Cys
            900                 905                 910

Arg Pro Asn Pro Cys His Asn Gly Gly Ser Cys Thr Asp Gly Ile Asn
        915                 920                 925

Thr Ala Phe Cys Asp Cys Leu Pro Gly Phe Arg Gly Thr Phe Cys Glu
    930                 935                 940

Glu Asp Ile Asn Glu Cys Ala Ser Asp Pro Cys Arg Asn Gly Ala Asn
945                 950                 955                 960

Cys Thr Asp Cys Val Asp Ser Tyr Thr Cys Thr Cys Pro Ala Gly Phe
            965                 970                 975

Ser Gly Ile His Cys Glu Asn Asn Thr Pro Asp Cys Thr Glu Ser Ser
            980                 985                 990

Cys Phe Asn Gly Gly Thr Cys Val Asp Gly Ile Asn Ser Phe Thr Cys
        995                 1000                1005

Leu Cys Pro Pro Gly Phe Thr Gly Ser Tyr Cys Gln His Asp Val
    1010                1015                1020

Asn Glu Cys Asp Ser Gln Pro Cys Leu His Gly Gly Thr Cys Gln
    1025                1030                1035

Asp Gly Cys Gly Ser Tyr Arg Cys Thr Cys Pro Gln Gly Tyr Thr
    1040                1045                1050

```
Gly Pro Asn Cys Gln Asn Leu Val His Trp Cys Asp Ser Ser Pro
    1055                1060                1065

Cys Lys Asn Gly Gly Lys Cys Trp Gln Thr His Thr Gln Tyr Arg
    1070                1075                1080

Cys Glu Cys Pro Ser Gly Trp Thr Gly Leu Tyr Cys Asp Val Pro
    1085                1090                1095

Ser Val Ser Cys Glu Val Ala Ala Gln Arg Gln Gly Val Asp Val
    1100                1105                1110

Ala Arg Leu Cys Gln His Gly Gly Leu Cys Val Asp Ala Gly Asn
    1115                1120                1125

Thr His His Cys Arg Cys Gln Ala Gly Tyr Thr Gly Ser Tyr Cys
    1130                1135                1140

Glu Asp Leu Val Asp Glu Cys Ser Pro Ser Pro Cys Gln Asn Gly
    1145                1150                1155

Ala Thr Cys Thr Asp Tyr Leu Gly Gly Tyr Ser Cys Lys Cys Val
    1160                1165                1170

Ala Gly Tyr His Gly Val Asn Cys Ser Glu Glu Ile Asp Glu Cys
    1175                1180                1185

Leu Ser His Pro Cys Gln Asn Gly Gly Thr Cys Leu Asp Leu Pro
    1190                1195                1200

Asn Thr Tyr Lys Cys Ser Cys Pro Arg Gly Thr Gln Gly Val His
    1205                1210                1215

Cys Glu Ile Asn Val Asp Asp Cys Asn Pro Pro Val Asp Pro Val
    1220                1225                1230

Ser Arg Ser Pro Lys Cys Phe Asn Asn Gly Thr Cys Val Asp Gln
    1235                1240                1245

Val Gly Gly Tyr Ser Cys Thr Cys Pro Pro Gly Phe Val Gly Glu
    1250                1255                1260

Arg Cys Glu Gly Asp Val Asn Glu Cys Leu Ser Asn Pro Cys Asp
    1265                1270                1275

Ala Arg Gly Thr Gln Asn Cys Val Gln Arg Val Asn Asp Phe His
    1280                1285                1290

Cys Glu Cys Arg Ala Gly His Thr Gly Arg Arg Cys Glu Ser Val
    1295                1300                1305

Ile Asn Gly Cys Lys Gly Lys Pro Cys Lys Asn Gly Gly Thr Cys
    1310                1315                1320

Ala Val Ala Ser Asn Thr Ala Arg Gly Phe Ile Cys Lys Cys Pro
    1325                1330                1335

Ala Gly Phe Glu Gly Ala Thr Cys Glu Asn Asp Ala Arg Thr Cys
    1340                1345                1350

Gly Ser Leu Arg Cys Leu Asn Gly Gly Thr Cys Ile Ser Gly Pro
    1355                1360                1365

Arg Ser Pro Thr Cys Leu Cys Leu Gly Pro Phe Thr Gly Pro Glu
    1370                1375                1380

Cys Gln Phe Pro Ala Ser Ser Pro Cys Leu Gly Gly Asn Pro Cys
    1385                1390                1395

Tyr Asn Gln Gly Thr Cys Glu Pro Thr Ser Glu Ser Pro Phe Tyr
    1400                1405                1410

Arg Cys Leu Cys Pro Ala Lys Phe Asn Gly Leu Leu Cys His Ile
    1415                1420                1425

Leu Asp Tyr Ser Phe Gly Gly Gly Ala Gly Arg Asp Ile Pro Pro
    1430                1435                1440

Pro Leu Ile Glu Glu Ala Cys Glu Leu Pro Glu Cys Gln Glu Asp
    1445                1450                1455
```

```
Ala Gly Asn Lys Val Cys Ser Leu Gln Cys Asn Asn His Ala Cys
     1460                1465                1470
Gly Trp Asp Gly Gly Asp Cys Ser Leu Asn Phe Asn Asp Pro Trp
     1475                1480                1485
Lys Asn Cys Thr Gln Ser Leu Gln Cys Trp Lys Tyr Phe Ser Asp
     1490                1495                1500
Gly His Cys Asp Ser Gln Cys Asn Ser Ala Gly Cys Leu Phe Asp
     1505                1510                1515
Gly Phe Asp Cys Gln Arg Ala Glu Gly Gln Cys Asn Pro Leu Tyr
     1520                1525                1530
Asp Gln Tyr Cys Lys Asp His Phe Ser Asp Gly His Cys Asp Gln
     1535                1540                1545
Gly Cys Asn Ser Ala Glu Cys Glu Trp Asp Gly Leu Asp Cys Ala
     1550                1555                1560
Glu His Val Pro Glu Arg Leu Ala Ala Gly Thr Leu Val Val Val
     1565                1570                1575
Val Leu Met Pro Pro Glu Gln Leu Arg Asn Ser Ser Phe His Phe
     1580                1585                1590
Leu Arg Glu Leu Ser Arg Val Leu His Thr Asn Val Val Phe Lys
     1595                1600                1605
Arg Asp Ala His Gly Gln Gln Met Ile Phe Pro Tyr Tyr Gly Arg
     1610                1615                1620
Glu Glu Glu Leu Arg Lys His Pro Ile Lys Arg Ala Ala Glu Gly
     1625                1630                1635
Trp Ala Ala Pro Asp Ala Leu Leu Gly Gln Val Lys Ala Ser Leu
     1640                1645                1650
Leu Pro Gly Gly Ser Glu Gly Gly Arg Arg Arg Glu Leu Asp
     1655                1660                1665
Pro Met Asp Val Arg Gly Ser Ile Val Tyr Leu Glu Ile Asp Asn
     1670                1675                1680
Arg Gln Cys Val Gln Ala Ser Ser Gln Cys Phe Gln Ser Ala Thr
     1685                1690                1695
Asp Val Ala Ala Phe Leu Gly Ala Leu Ala Ser Leu Gly Ser Leu
     1700                1705                1710
Asn Ile Pro Tyr Lys Ile Glu Ala Val Gln Ser Glu Thr Val Glu
     1715                1720                1725
Pro Pro Pro Pro Ala Gln Leu His Phe Met Tyr Val Ala Ala Ala
     1730                1735                1740
Ala Phe Val Leu Leu Phe Phe Val Gly Cys Gly Val Leu Leu Ser
     1745                1750                1755
Arg Lys Arg Arg Arg Gln His Gly Gln Leu Trp Phe Pro Glu Gly
     1760                1765                1770
Phe Lys Val Ser Glu Ala Ser Lys Lys Lys Arg Arg Glu Pro Leu
     1775                1780                1785
Gly Glu Asp Ser Val Gly Leu Lys Pro Leu Lys Asn Ala Ser Asp
     1790                1795                1800
Gly Ala Leu Met Asp Asp Asn Gln Asn Glu Trp Gly Asp Glu Asp
     1805                1810                1815
Leu Glu Thr Lys Lys Phe Arg Phe Glu Glu Pro Val Val Leu Pro
     1820                1825                1830
Asp Leu Asp Asp Gln Thr Asp His Arg Gln Trp Thr Gln Gln His
     1835                1840                1845
Leu Asp Ala Ala Asp Leu Arg Met Ser Ala Met Ala Pro Thr Pro
     1850                1855                1860
```

-continued

Pro Gln Gly Glu Val Asp Ala Asp Cys Met Asp Val Asn Val Arg
1865                1870                1875

Gly Pro Asp Gly Phe Thr Pro Leu Met Ile Ala Ser Cys Ser Gly
1880                1885                1890

Gly Gly Leu Glu Thr Gly Asn Ser Glu Glu Glu Asp Ala Pro
1895                1900                1905

Ala Val Ile Ser Asp Phe Ile Tyr Gln Gly Ala Ser Leu His Asn
1910                1915                1920

Gln Thr Asp Arg Thr Gly Glu Thr Ala Leu His Leu Ala Ala Arg
1925                1930                1935

Tyr Ser Arg Ser Asp Ala Ala Lys Arg Leu Leu Glu Ala Ser Ala
1940                1945                1950

Asp Ala Asn Ile Gln Asp Asn Met Gly Arg Thr Pro Leu His Ala
1955                1960                1965

Ala Val Ser Ala Asp Ala Gln Gly Val Phe Gln Ile Leu Ile Arg
1970                1975                1980

Asn Arg Ala Thr Asp Leu Asp Ala Arg Met His Asp Gly Thr Thr
1985                1990                1995

Pro Leu Ile Leu Ala Ala Arg Leu Ala Val Glu Gly Met Leu Glu
2000                2005                2010

Asp Leu Ile Asn Ser His Ala Asp Val Asn Ala Val Asp Asp Leu
2015                2020                2025

Gly Lys Ser Ala Leu His Trp Ala Ala Ala Val Asn Asn Val Asp
2030                2035                2040

Ala Ala Val Val Leu Leu Lys Asn Gly Ala Asn Lys Asp Met Gln
2045                2050                2055

Asn Asn Arg Glu Glu Thr Pro Leu Phe Leu Ala Ala Arg Glu Gly
2060                2065                2070

Ser Tyr Glu Thr Ala Lys Val Leu Leu Asp His Phe Ala Asn Arg
2075                2080                2085

Asp Ile Thr Asp His Met Asp Arg Leu Pro Arg Asp Ile Ala Gln
2090                2095                2100

Glu Arg Met His His Asp Ile Val Arg Leu Leu Asp Glu Tyr Asn
2105                2110                2115

Leu Val Arg Ser Pro Gln Leu His Gly Ala Pro Leu Gly Gly Thr
2120                2125                2130

Pro Thr Leu Ser Pro Pro Leu Cys Ser Pro Asn Gly Tyr Leu Gly
2135                2140                2145

Ser Leu Lys Pro Gly Val Gln Gly Lys Lys Val Arg Lys Pro Ser
2150                2155                2160

Ser Lys Gly Leu Ala Cys Gly Ser Lys Glu Ala Lys Asp Leu Lys
2165                2170                2175

Ala Arg Arg Lys Lys Ser Gln Asp Gly Lys Gly Cys Leu Leu Asp
2180                2185                2190

Ser Ser Gly Met Leu Ser Pro Val Asp Ser Leu Glu Ser Pro His
2195                2200                2205

Gly Tyr Leu Ser Asp Val Ala Ser Pro Pro Leu Leu Pro Ser Pro
2210                2215                2220

Phe Gln Gln Ser Pro Ser Val Pro Leu Asn His Leu Pro Gly Met
2225                2230                2235

Pro Asp Thr His Leu Gly Ile Gly His Leu Asn Val Ala Ala Lys
2240                2245                2250

Pro Glu Met Ala Ala Leu Gly Gly Gly Gly Arg Leu Ala Phe Glu
2255                2260                2265

```
Thr Gly Pro Pro Arg Leu Ser His Leu Pro Val Ala Ser Gly Thr
    2270                2275                2280

Ser Thr Val Leu Gly Ser Ser Gly Gly Ala Leu Asn Phe Thr
    2285                2290                2295

Val Gly Gly Ser Thr Ser Leu Asn Gly Gln Cys Glu Trp Leu Ser
    2300                2305                2310

Arg Leu Gln Ser Gly Met Val Pro Asn Gln Tyr Asn Pro Leu Arg
    2315                2320                2325

Gly Ser Val Ala Pro Gly Pro Leu Ser Thr Gln Ala Pro Ser Leu
    2330                2335                2340

Gln His Gly Met Val Gly Pro Leu His Ser Ser Leu Ala Ala Ser
    2345                2350                2355

Ala Leu Ser Gln Met Met Ser Tyr Gln Gly Leu Pro Ser Thr Arg
    2360                2365                2370

Leu Ala Thr Gln Pro His Leu Val Gln Thr Gln Val Gln Pro
    2375                2380                2385

Gln Asn Leu Gln Met Gln Gln Gln Asn Leu Gln Pro Ala Asn Ile
    2390                2395                2400

Gln Gln Gln Gln Ser Leu Gln Pro Pro Pro Pro Pro Gln Pro
    2405                2410                2415

His Leu Gly Val Ser Ser Ala Ala Ser Gly His Leu Gly Arg Ser
    2420                2425                2430

Phe Leu Ser Gly Glu Pro Ser Gln Ala Asp Val Gln Pro Leu Gly
    2435                2440                2445

Pro Ser Ser Leu Ala Val His Thr Ile Leu Pro Gln Glu Ser Pro
    2450                2455                2460

Ala Leu Pro Thr Ser Leu Pro Ser Ser Leu Val Pro Pro Val Thr
    2465                2470                2475

Ala Ala Gln Phe Leu Thr Pro Pro Ser Gln His Ser Tyr Ser Ser
    2480                2485                2490

Pro Val Asp Asn Thr Pro Ser His Gln Leu Gln Val Pro Glu His
    2495                2500                2505

Pro Phe Leu Thr Pro Ser Pro Glu Ser Pro Asp Gln Trp Ser Ser
    2510                2515                2520

Ser Ser Pro His Ser Asn Val Ser Asp Trp Ser Glu Gly Val Ser
    2525                2530                2535

Ser Pro Pro Thr Ser Met Gln Ser Gln Ile Ala Arg Ile Pro Glu
    2540                2545                2550

Ala Phe Lys
    2555

<210> SEQ ID NO 40
<211> LENGTH: 2471
<212> TYPE: PRT
<213> ORGANISM: Homo sapiens

<400> SEQUENCE: 40

Met Pro Ala Leu Arg Pro Ala Leu Leu Trp Ala Leu Ala Leu Trp
1               5                   10                  15

Leu Cys Cys Ala Ala Pro Ala His Ala Leu Gln Cys Arg Asp Gly Tyr
                20                  25                  30

Glu Pro Cys Val Asn Glu Gly Met Cys Val Thr Tyr His Asn Gly Thr
            35                  40                  45

Gly Tyr Cys Lys Cys Pro Glu Gly Phe Leu Gly Glu Tyr Cys Gln His
        50                  55                  60
```

```
Arg Asp Pro Cys Glu Lys Asn Arg Cys Gln Asn Gly Gly Thr Cys Val
 65                  70                  75                  80

Ala Gln Ala Met Leu Gly Lys Ala Thr Cys Arg Cys Ala Ser Gly Phe
                 85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
            115                 120                 125

Tyr Glu Cys Thr Cys Gln Val Gly Phe Thr Gly Lys Glu Cys Gln Trp
            130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
            195                 200                 205

Cys Pro Gln Gly Phe Thr Gly Gln Tyr Cys Asp Ser Leu Tyr Val Pro
210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
            275                 280                 285

Gln Trp Thr Gly Gln Phe Cys Thr Glu Asp Val Asp Glu Cys Leu Leu
290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
            355                 360                 365

Ala Gly Leu Leu Cys His Leu Asp Asp Ala Cys Ile Ser Asn Pro Cys
            370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
            435                 440                 445

Ala Gly Pro Arg Cys Glu Met Asp Ile Asn Glu Cys His Ser Asp Pro
            450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495
```

-continued

```
Glu Cys Gln Ser Asn Pro Cys Val Asn Asn Gly Gln Cys Val Asp Lys
            500                 505                 510
Val Asn Arg Phe Gln Cys Leu Cys Pro Pro Gly Phe Thr Gly Pro Val
        515                 520                 525
Cys Gln Ile Asp Ile Asp Asp Cys Ser Ser Thr Pro Cys Leu Asn Gly
    530                 535                 540
Ala Lys Cys Ile Asp His Pro Asn Gly Tyr Glu Cys Gln Cys Ala Thr
545                 550                 555                 560
Gly Phe Thr Gly Val Leu Cys Glu Glu Asn Ile Asp Asn Cys Asp Pro
                565                 570                 575
Asp Pro Cys His His Gly Gln Cys Gln Asp Gly Ile Asp Ser Tyr Thr
            580                 585                 590
Cys Ile Cys Asn Pro Gly Tyr Met Gly Ala Ile Cys Ser Asp Gln Ile
        595                 600                 605
Asp Glu Cys Tyr Ser Ser Pro Cys Leu Asn Asp Gly Arg Cys Ile Asp
    610                 615                 620
Leu Val Asn Gly Tyr Gln Cys Asn Cys Gln Pro Gly Thr Ser Gly Val
625                 630                 635                 640
Asn Cys Glu Ile Asn Phe Asp Asp Cys Ala Ser Asn Pro Cys Ile His
                645                 650                 655
Gly Ile Cys Met Asp Gly Ile Asn Arg Tyr Ser Cys Val Cys Ser Pro
            660                 665                 670
Gly Phe Thr Gly Gln Arg Cys Asn Ile Asp Ile Asp Glu Cys Ala Ser
        675                 680                 685
Asn Pro Cys Arg Lys Gly Ala Thr Cys Ile Asn Gly Val Asn Gly Phe
    690                 695                 700
Arg Cys Ile Cys Pro Glu Gly Pro His His Pro Ser Cys Tyr Ser Gln
705                 710                 715                 720
Val Asn Glu Cys Leu Ser Asn Pro Cys Ile His Gly Asn Cys Thr Gly
                725                 730                 735
Gly Leu Ser Gly Tyr Lys Cys Leu Cys Asp Ala Gly Trp Val Gly Ile
            740                 745                 750
Asn Cys Glu Val Asp Lys Asn Glu Cys Leu Ser Asn Pro Cys Gln Asn
        755                 760                 765
Gly Gly Thr Cys Asp Asn Leu Val Asn Gly Tyr Arg Cys Thr Cys Lys
    770                 775                 780
Lys Gly Phe Lys Gly Tyr Asn Cys Gln Val Asn Ile Asp Glu Cys Ala
785                 790                 795                 800
Ser Asn Pro Cys Leu Asn Gln Gly Thr Cys Phe Asp Asp Ile Ser Gly
                805                 810                 815
Tyr Thr Cys His Cys Val Leu Pro Tyr Thr Gly Lys Asn Cys Gln Thr
            820                 825                 830
Val Leu Ala Pro Cys Ser Pro Asn Pro Cys Glu Asn Ala Ala Val Cys
        835                 840                 845
Lys Glu Ser Pro Asn Phe Glu Ser Tyr Thr Cys Leu Cys Ala Pro Gly
    850                 855                 860
Trp Gln Gly Gln Arg Cys Thr Ile Asp Ile Asp Glu Cys Ile Ser Lys
865                 870                 875                 880
Pro Cys Met Asn His Gly Leu Cys His Asn Thr Gln Gly Ser Tyr Met
                885                 890                 895
Cys Glu Cys Pro Pro Gly Phe Ser Gly Met Asp Cys Glu Glu Asp Ile
            900                 905                 910
Asp Asp Cys Leu Ala Asn Pro Cys Gln Asn Gly Gly Ser Cys Met Asp
        915                 920                 925
```

-continued

```
Gly Val Asn Thr Phe Ser Cys Leu Cys Leu Pro Gly Phe Thr Gly Asp
930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
                965                 970                 975

Ala Gly Phe Asp Gly Val His Cys Glu Asn Asn Ile Asn Glu Cys Thr
            980                 985                 990

Glu Ser Ser Cys Phe Asn Gly Gly Thr Cys Val Asp Gly Ile Asn Ser
        995                 1000                1005

Phe Ser Cys Leu Cys Pro Val Gly Phe Thr Gly Ser Phe Cys Leu
    1010                1015                1020

His Glu Ile Asn Glu Cys Ser Ser His Pro Cys Leu Asn Glu Gly
    1025                1030                1035

Thr Cys Val Asp Gly Leu Gly Thr Tyr Arg Cys Ser Cys Pro Leu
    1040                1045                1050

Gly Tyr Thr Gly Lys Asn Cys Gln Thr Leu Val Asn Leu Cys Ser
    1055                1060                1065

Arg Ser Pro Cys Lys Asn Lys Gly Thr Cys Val Gln Lys Lys Ala
    1070                1075                1080

Glu Ser Gln Cys Leu Cys Pro Ser Gly Trp Ala Gly Ala Tyr Cys
    1085                1090                1095

Asp Val Pro Asn Val Ser Cys Asp Ile Ala Ala Ser Arg Arg Gly
    1100                1105                1110

Val Leu Val Glu His Leu Cys Gln His Ser Gly Val Cys Ile Asn
    1115                1120                1125

Ala Gly Asn Thr His Tyr Cys Gln Cys Pro Leu Gly Tyr Thr Gly
    1130                1135                1140

Ser Tyr Cys Glu Glu Gln Leu Asp Glu Cys Ala Ser Asn Pro Cys
    1145                1150                1155

Gln His Gly Ala Thr Cys Ser Asp Phe Ile Gly Gly Tyr Arg Cys
    1160                1165                1170

Glu Cys Val Pro Gly Tyr Gln Gly Val Asn Cys Glu Tyr Glu Val
    1175                1180                1185

Asp Glu Cys Gln Asn Gln Pro Cys Gln Asn Gly Gly Thr Cys Ile
    1190                1195                1200

Asp Leu Val Asn His Phe Lys Cys Ser Cys Pro Pro Gly Thr Arg
    1205                1210                1215

Gly Leu Leu Cys Glu Glu Asn Ile Asp Asp Cys Ala Arg Gly Pro
    1220                1225                1230

His Cys Leu Asn Gly Gly Gln Cys Met Asp Arg Ile Gly Gly Tyr
    1235                1240                1245

Ser Cys Arg Cys Leu Pro Gly Phe Ala Gly Glu Arg Cys Glu Gly
    1250                1255                1260

Asp Ile Asn Glu Cys Leu Ser Asn Pro Cys Ser Ser Glu Gly Ser
    1265                1270                1275

Leu Asp Cys Ile Gln Leu Thr Asn Asp Tyr Leu Cys Val Cys Arg
    1280                1285                1290

Ser Ala Phe Thr Gly Arg His Cys Glu Thr Phe Val Asp Val Cys
    1295                1300                1305

Pro Gln Met Pro Cys Leu Asn Gly Gly Thr Cys Ala Val Ala Ser
    1310                1315                1320

Asn Met Pro Asp Gly Phe Ile Cys Arg Cys Pro Pro Gly Phe Ser
    1325                1330                1335
```

```
Gly Ala Arg Cys Gln Ser Ser Cys Gly Gln Val Lys Cys Arg Lys
    1340                1345                1350

Gly Glu Gln Cys Val His Thr Ala Ser Gly Pro Arg Cys Phe Cys
    1355                1360                1365

Pro Ser Pro Arg Asp Cys Glu Ser Gly Cys Ala Ser Ser Pro Cys
    1370                1375                1380

Gln His Gly Gly Ser Cys His Pro Gln Arg Gln Pro Pro Tyr Tyr
    1385                1390                1395

Ser Cys Gln Cys Ala Pro Pro Phe Ser Gly Ser Arg Cys Glu Leu
    1400                1405                1410

Tyr Thr Ala Pro Pro Ser Thr Pro Pro Ala Thr Cys Leu Ser Gln
    1415                1420                1425

Tyr Cys Ala Asp Lys Ala Arg Asp Gly Val Cys Asp Glu Ala Cys
    1430                1435                1440

Asn Ser His Ala Cys Gln Trp Asp Gly Gly Asp Cys Ser Leu Thr
    1445                1450                1455

Met Glu Asn Pro Trp Ala Asn Cys Ser Ser Pro Leu Pro Cys Trp
    1460                1465                1470

Asp Tyr Ile Asn Asn Gln Cys Asp Glu Leu Cys Asn Thr Val Glu
    1475                1480                1485

Cys Leu Phe Asp Asn Phe Glu Cys Gln Gly Asn Ser Lys Thr Cys
    1490                1495                1500

Lys Tyr Asp Lys Tyr Cys Ala Asp His Phe Lys Asp Asn His Cys
    1505                1510                1515

Asp Gln Gly Cys Asn Ser Glu Glu Cys Gly Trp Asp Gly Leu Asp
    1520                1525                1530

Cys Ala Ala Asp Gln Pro Glu Asn Leu Ala Glu Gly Thr Leu Val
    1535                1540                1545

Ile Val Val Leu Met Pro Pro Glu Gln Leu Leu Gln Asp Ala Arg
    1550                1555                1560

Ser Phe Leu Arg Ala Leu Gly Thr Leu Leu His Thr Asn Leu Arg
    1565                1570                1575

Ile Lys Arg Asp Ser Gln Gly Glu Leu Met Val Tyr Pro Tyr Tyr
    1580                1585                1590

Gly Glu Lys Ser Ala Ala Met Lys Lys Gln Arg Met Thr Arg Arg
    1595                1600                1605

Ser Leu Pro Gly Glu Gln Glu Gln Glu Val Ala Gly Ser Lys Val
    1610                1615                1620

Phe Leu Glu Ile Asp Asn Arg Gln Cys Val Gln Asp Ser Asp His
    1625                1630                1635

Cys Phe Lys Asn Thr Asp Ala Ala Ala Ala Leu Leu Ala Ser His
    1640                1645                1650

Ala Ile Gln Gly Thr Leu Ser Tyr Pro Leu Val Ser Val Val Ser
    1655                1660                1665

Glu Ser Leu Thr Pro Glu Arg Thr Gln Leu Leu Tyr Leu Leu Ala
    1670                1675                1680

Val Ala Val Val Ile Ile Leu Phe Ile Ile Leu Leu Gly Val Ile
    1685                1690                1695

Met Ala Lys Arg Lys Arg Lys His Gly Ser Leu Trp Leu Pro Glu
    1700                1705                1710

Gly Phe Thr Leu Arg Arg Asp Ala Ser Asn His Lys Arg Arg Glu
    1715                1720                1725

Pro Val Gly Gln Asp Ala Val Gly Leu Lys Asn Leu Ser Val Gln
    1730                1735                1740
```

-continued

```
Val Ser Glu Ala Asn Leu Ile Gly Thr Gly Thr Ser Glu His Trp
1745                1750                1755

Val Asp Asp Glu Gly Pro Gln Pro Lys Lys Val Lys Ala Glu Asp
1760                1765                1770

Glu Ala Leu Leu Ser Glu Glu Asp Asp Pro Ile Asp Arg Arg Pro
1775                1780                1785

Trp Thr Gln Gln His Leu Glu Ala Ala Asp Ile Arg Arg Thr Pro
1790                1795                1800

Ser Leu Ala Leu Thr Pro Pro Gln Ala Glu Gln Glu Val Asp Val
1805                1810                1815

Leu Asp Val Asn Val Arg Gly Pro Asp Gly Cys Thr Pro Leu Met
1820                1825                1830

Leu Ala Ser Leu Arg Gly Gly Ser Ser Asp Leu Ser Asp Glu Asp
1835                1840                1845

Glu Asp Ala Glu Asp Ser Ser Ala Asn Ile Ile Thr Asp Leu Val
1850                1855                1860

Tyr Gln Gly Ala Ser Leu Gln Ala Gln Thr Asp Arg Thr Gly Glu
1865                1870                1875

Met Ala Leu His Leu Ala Ala Arg Tyr Ser Arg Ala Asp Ala Ala
1880                1885                1890

Lys Arg Leu Leu Asp Ala Gly Ala Asp Ala Asn Ala Gln Asp Asn
1895                1900                1905

Met Gly Arg Cys Pro Leu His Ala Ala Val Ala Ala Asp Ala Gln
1910                1915                1920

Gly Val Phe Gln Ile Leu Ile Arg Asn Arg Val Thr Asp Leu Asp
1925                1930                1935

Ala Arg Met Asn Asp Gly Thr Thr Pro Leu Ile Leu Ala Ala Arg
1940                1945                1950

Leu Ala Val Glu Gly Met Val Ala Glu Leu Ile Asn Cys Gln Ala
1955                1960                1965

Asp Val Asn Ala Val Asp Asp His Gly Lys Ser Ala Leu His Trp
1970                1975                1980

Ala Ala Ala Val Asn Asn Val Glu Ala Thr Leu Leu Leu Leu Lys
1985                1990                1995

Asn Gly Ala Asn Arg Asp Met Gln Asp Asn Lys Glu Glu Thr Pro
2000                2005                2010

Leu Phe Leu Ala Ala Arg Glu Gly Ser Tyr Glu Ala Ala Lys Ile
2015                2020                2025

Leu Leu Asp His Phe Ala Asn Arg Asp Ile Thr Asp His Met Asp
2030                2035                2040

Arg Leu Pro Arg Asp Val Ala Arg Asp Arg Met His His Asp Ile
2045                2050                2055

Val Arg Leu Leu Asp Glu Tyr Asn Val Thr Pro Ser Pro Pro Gly
2060                2065                2070

Thr Val Leu Thr Ser Ala Leu Ser Pro Val Ile Cys Gly Pro Asn
2075                2080                2085

Arg Ser Phe Leu Ser Leu Lys His Thr Pro Met Gly Lys Lys Ser
2090                2095                2100

Arg Arg Pro Ser Ala Lys Ser Thr Met Pro Thr Ser Leu Pro Asn
2105                2110                2115

Leu Ala Lys Glu Ala Lys Asp Ala Lys Gly Ser Arg Arg Lys Lys
2120                2125                2130

Ser Leu Ser Glu Lys Val Gln Leu Ser Glu Ser Ser Val Thr Leu
2135                2140                2145
```

| | | | | | | | | | | |
|---|---|---|---|---|---|---|---|---|---|---|
| Ser | Pro | Val | Asp | Ser | Leu | Glu | Ser | Pro | His | Thr | Tyr | Val | Ser | Asp |
| | 2150 | | | | 2155 | | | | 2160 | |

| Thr | Thr | Ser | Ser | Pro | Met | Ile | Thr | Ser | Pro | Gly | Ile | Leu | Gln | Ala |
| 2165 | | | | | 2170 | | | | | 2175 | |

| Ser | Pro | Asn | Pro | Met | Leu | Ala | Thr | Ala | Ala | Pro | Ala | Pro | Val |
| | 2180 | | | | | 2185 | | | | | 2190 |

| His | Ala | Gln | His | Ala | Leu | Ser | Phe | Ser | Asn | Leu | His | Glu | Met | Gln |
| | 2195 | | | | | 2200 | | | | | 2205 | |

| Pro | Leu | Ala | His | Gly | Ala | Ser | Thr | Val | Leu | Pro | Ser | Val | Ser | Gln |
| | 2210 | | | | | 2215 | | | | | 2220 | |

| Leu | Leu | Ser | His | His | His | Ile | Val | Ser | Pro | Gly | Ser | Gly | Ser | Ala |
| | 2225 | | | | | 2230 | | | | | 2235 | |

| Gly | Ser | Leu | Ser | Arg | Leu | His | Pro | Val | Pro | Val | Pro | Ala | Asp | Trp |
| | 2240 | | | | | 2245 | | | | | 2250 | |

| Met | Asn | Arg | Met | Glu | Val | Asn | Glu | Thr | Gln | Tyr | Asn | Glu | Met | Phe |
| | 2255 | | | | | 2260 | | | | | 2265 | |

| Gly | Met | Val | Leu | Ala | Pro | Ala | Glu | Gly | Thr | His | Pro | Gly | Ile | Ala |
| | 2270 | | | | | 2275 | | | | | 2280 | |

| Pro | Gln | Ser | Arg | Pro | Pro | Glu | Gly | Lys | His | Ile | Thr | Thr | Pro | Arg |
| | 2285 | | | | | 2290 | | | | | 2295 | |

| Glu | Pro | Leu | Pro | Pro | Ile | Val | Thr | Phe | Gln | Leu | Ile | Pro | Lys | Gly |
| | 2300 | | | | | 2305 | | | | | 2310 | |

| Ser | Ile | Ala | Gln | Pro | Ala | Gly | Ala | Pro | Gln | Pro | Gln | Ser | Thr | Cys |
| | 2315 | | | | | 2320 | | | | | 2325 | |

| Pro | Pro | Ala | Val | Ala | Gly | Pro | Leu | Pro | Thr | Met | Tyr | Gln | Ile | Pro |
| | 2330 | | | | | 2335 | | | | | 2340 | |

| Glu | Met | Ala | Arg | Leu | Pro | Ser | Val | Ala | Phe | Pro | Thr | Ala | Met | Met |
| | 2345 | | | | | 2350 | | | | | 2355 | |

| Pro | Gln | Gln | Asp | Gly | Gln | Val | Ala | Gln | Thr | Ile | Leu | Pro | Ala | Tyr |
| | 2360 | | | | | 2365 | | | | | 2370 | |

| His | Pro | Phe | Pro | Ala | Ser | Val | Gly | Lys | Tyr | Pro | Thr | Pro | Pro | Ser |
| | 2375 | | | | | 2380 | | | | | 2385 | |

| Gln | His | Ser | Tyr | Ala | Ser | Ser | Asn | Ala | Ala | Glu | Arg | Thr | Pro | Ser |
| | 2390 | | | | | 2395 | | | | | 2400 | |

| His | Ser | Gly | His | Leu | Gln | Gly | Glu | His | Pro | Tyr | Leu | Thr | Pro | Ser |
| | 2405 | | | | | 2410 | | | | | 2415 | |

| Pro | Glu | Ser | Pro | Asp | Gln | Trp | Ser | Ser | Ser | Pro | His | Ser | Ala |
| | 2420 | | | | | 2425 | | | | | 2430 |

| Ser | Asp | Trp | Ser | Asp | Val | Thr | Thr | Ser | Pro | Thr | Pro | Gly | Gly | Ala |
| | 2435 | | | | | 2440 | | | | | 2445 | |

| Gly | Gly | Gly | Gln | Arg | Gly | Pro | Gly | Thr | His | Met | Ser | Glu | Pro | Pro |
| | 2450 | | | | | 2455 | | | | | 2460 | |

| His | Asn | Asn | Met | Gln | Val | Tyr | Ala |
| | 2465 | | | | 2470 | |

```
<210> SEQ ID NO 41
<211> LENGTH: 2002
<212> TYPE: PRT
<213> ORGANISM: Homo sapiens

<400> SEQUENCE: 41
```

| Met | Gln | Pro | Pro | Ser | Leu | Leu | Leu | Leu | Leu | Leu | Leu | Leu | Cys |
| 1 | | | | 5 | | | | | 10 | | | | | 15 |

| Val | Ser | Val | Val | Arg | Pro | Arg | Gly | Leu | Leu | Cys | Gly | Ser | Phe | Pro | Glu |
| | | | 20 | | | | | 25 | | | | | 30 |

-continued

```
Pro Cys Ala Asn Gly Gly Thr Cys Leu Ser Leu Ser Leu Gly Gln Gly
        35                  40                  45

Thr Cys Gln Cys Ala Pro Gly Phe Leu Gly Glu Thr Cys Gln Phe Pro
 50                  55                  60

Asp Pro Cys Gln Asn Ala Gln Leu Cys Gln Asn Gly Gly Ser Cys Gln
 65                  70                  75                  80

Ala Leu Leu Pro Ala Pro Leu Gly Leu Pro Ser Ser Pro Ser Pro Leu
                 85                  90                  95

Thr Pro Ser Phe Leu Cys Thr Cys Leu Pro Gly Phe Thr Gly Glu Arg
                100                 105                 110

Cys Gln Ala Lys Leu Glu Asp Pro Cys Pro Ser Phe Cys Ser Lys
                115                 120                 125

Arg Gly Arg Cys His Ile Gln Ala Ser Gly Arg Pro Gln Cys Ser Cys
        130                 135                 140

Met Pro Gly Trp Thr Gly Glu Gln Cys Gln Leu Arg Asp Phe Cys Ser
145                 150                 155                 160

Ala Asn Pro Cys Val Asn Gly Gly Val Cys Leu Ala Thr Tyr Pro Gln
                165                 170                 175

Ile Gln Cys His Cys Pro Pro Gly Phe Glu Gly His Ala Cys Glu Arg
                180                 185                 190

Asp Val Asn Glu Cys Phe Gln Asp Pro Gly Pro Cys Pro Lys Gly Thr
                195                 200                 205

Ser Cys His Asn Thr Leu Gly Ser Phe Gln Cys Leu Cys Pro Val Gly
        210                 215                 220

Gln Glu Gly Pro Arg Cys Glu Leu Arg Ala Gly Pro Cys Pro Pro Arg
225                 230                 235                 240

Gly Cys Ser Asn Gly Gly Thr Cys Gln Leu Met Pro Glu Lys Asp Ser
                245                 250                 255

Thr Phe His Leu Cys Leu Cys Pro Pro Gly Phe Ile Gly Pro Gly Cys
                260                 265                 270

Glu Val Asn Pro Asp Asn Cys Val Ser His Gln Cys Gln Asn Gly Gly
        275                 280                 285

Thr Cys Gln Asp Gly Leu Asp Thr Tyr Thr Cys Leu Cys Pro Glu Thr
        290                 295                 300

Trp Thr Gly Trp Asp Cys Ser Glu Asp Val Asp Glu Cys Glu Ala Gln
305                 310                 315                 320

Gly Pro Pro His Cys Arg Asn Gly Gly Thr Cys Gln Asn Ser Ala Gly
                325                 330                 335

Ser Phe His Cys Val Cys Val Ser Gly Trp Gly Gly Thr Ser Cys Glu
                340                 345                 350

Glu Asn Leu Asp Asp Cys Ile Ala Ala Thr Cys Ala Pro Gly Ser Thr
        355                 360                 365

Cys Ile Asp Arg Val Gly Ser Phe Ser Cys Leu Cys Pro Pro Gly Arg
370                 375                 380

Thr Gly Leu Leu Cys His Leu Glu Asp Met Cys Leu Ser Gln Pro Cys
385                 390                 395                 400

His Gly Asp Ala Gln Cys Ser Thr Asn Pro Leu Thr Gly Ser Thr Leu
                405                 410                 415

Cys Leu Cys Gln Pro Gly Tyr Ser Gly Pro Thr Cys His Gln Asp Leu
                420                 425                 430

Asp Glu Cys Leu Met Ala Gln Gln Gly Pro Ser Pro Cys Glu His Gly
        435                 440                 445

Gly Ser Cys Leu Asn Thr Pro Gly Ser Phe Asn Cys Leu Cys Pro Pro
450                 455                 460
```

```
Gly Tyr Thr Gly Ser Arg Cys Glu Ala Asp His Asn Glu Cys Leu Ser
465                 470                 475                 480

Gln Pro Cys His Pro Gly Ser Thr Cys Leu Asp Leu Leu Ala Thr Phe
                485                 490                 495

His Cys Leu Cys Pro Pro Gly Leu Glu Gly Gln Leu Cys Glu Val Glu
            500                 505                 510

Thr Asn Glu Cys Ala Ser Ala Pro Cys Leu Asn His Ala Asp Cys His
        515                 520                 525

Asp Leu Leu Asn Gly Phe Gln Cys Ile Cys Leu Pro Gly Phe Ser Gly
    530                 535                 540

Thr Arg Cys Glu Glu Asp Ile Asp Glu Cys Arg Ser Pro Cys Ala
545                 550                 555                 560

Asn Gly Gly Gln Cys Gln Asp Gln Pro Gly Ala Phe His Cys Lys Cys
                565                 570                 575

Leu Pro Gly Phe Glu Gly Pro Arg Cys Gln Thr Glu Val Asp Glu Cys
            580                 585                 590

Leu Ser Asp Pro Cys Pro Val Gly Ala Ser Cys Leu Asp Leu Pro Gly
        595                 600                 605

Ala Phe Phe Cys Leu Cys Pro Ser Gly Phe Thr Gly Gln Leu Cys Glu
    610                 615                 620

Val Pro Leu Cys Ala Pro Asn Leu Cys Gln Pro Lys Gln Ile Cys Lys
625                 630                 635                 640

Asp Gln Lys Asp Lys Ala Asn Cys Leu Cys Pro Asp Gly Ser Pro Gly
                645                 650                 655

Cys Ala Pro Pro Glu Asp Asn Cys Thr Cys His His Gly His Cys Gln
            660                 665                 670

Arg Ser Ser Cys Val Cys Asp Val Gly Trp Thr Gly Pro Glu Cys Glu
        675                 680                 685

Ala Glu Leu Gly Gly Cys Ile Ser Ala Pro Cys Ala His Gly Gly Thr
    690                 695                 700

Cys Tyr Pro Gln Pro Ser Gly Tyr Asn Cys Thr Cys Pro Thr Gly Tyr
705                 710                 715                 720

Thr Gly Pro Thr Cys Ser Glu Glu Met Thr Ala Cys His Ser Gly Pro
                725                 730                 735

Cys Leu Asn Gly Gly Ser Cys Asn Pro Ser Pro Gly Gly Tyr Tyr Cys
            740                 745                 750

Thr Cys Pro Pro Ser His Thr Gly Pro Gln Cys Gln Thr Ser Thr Asp
        755                 760                 765

Tyr Cys Val Ser Ala Pro Cys Phe Asn Gly Gly Thr Cys Val Asn Arg
    770                 775                 780

Pro Gly Thr Phe Ser Cys Leu Cys Ala Met Gly Phe Gln Gly Pro Arg
785                 790                 795                 800

Cys Glu Gly Lys Leu Arg Pro Ser Cys Ala Asp Ser Pro Cys Arg Asn
                805                 810                 815

Arg Ala Thr Cys Gln Asp Ser Pro Gln Gly Pro Arg Cys Leu Cys Pro
            820                 825                 830

Thr Gly Tyr Thr Gly Gly Ser Cys Gln Thr Leu Met Asp Leu Cys Ala
        835                 840                 845

Gln Lys Pro Cys Pro Arg Asn Ser His Cys Leu Gln Thr Gly Pro Ser
    850                 855                 860

Phe His Cys Leu Cys Leu Gln Gly Trp Thr Gly Pro Leu Cys Asn Leu
865                 870                 875                 880

Pro Leu Ser Ser Cys Gln Lys Ala Ala Leu Ser Gln Gly Ile Asp Val
                885                 890                 895
```

-continued

```
Ser Ser Leu Cys His Asn Gly Gly Leu Cys Val Asp Ser Gly Pro Ser
            900                 905                 910

Tyr Phe Cys His Cys Pro Pro Gly Phe Gln Gly Ser Leu Cys Gln Asp
            915                 920                 925

His Val Asn Pro Cys Glu Ser Arg Pro Cys Gln Asn Gly Ala Thr Cys
            930                 935                 940

Met Ala Gln Pro Ser Gly Tyr Leu Cys Gln Cys Ala Pro Gly Tyr Asp
945                 950                 955                 960

Gly Gln Asn Cys Ser Lys Glu Leu Asp Ala Cys Gln Ser Gln Pro Cys
                965                 970                 975

His Asn His Gly Thr Cys Thr Pro Lys Pro Gly Gly Phe His Cys Ala
            980                 985                 990

Cys Pro Pro Gly Phe Val Gly Leu Arg Cys Glu Gly Asp Val Asp Glu
            995                 1000                1005

Cys Leu Asp Gln Pro Cys His Pro Thr Gly Thr Ala Ala Cys His
            1010                1015                1020

Ser Leu Ala Asn Ala Phe Tyr Cys Gln Cys Leu Pro Gly His Thr
            1025                1030                1035

Gly Gln Trp Cys Glu Val Glu Ile Asp Pro Cys His Ser Gln Pro
            1040                1045                1050

Cys Phe His Gly Gly Thr Cys Glu Ala Thr Ala Gly Ser Pro Leu
            1055                1060                1065

Gly Phe Ile Cys His Cys Pro Lys Gly Phe Glu Gly Pro Thr Cys
            1070                1075                1080

Ser His Arg Ala Pro Ser Cys Gly Phe His Cys His His Gly
            1085                1090                1095

Gly Leu Cys Leu Pro Ser Pro Lys Pro Gly Phe Pro Pro Arg Cys
            1100                1105                1110

Ala Cys Leu Ser Gly Tyr Gly Gly Pro Asp Cys Leu Thr Pro Pro
            1115                1120                1125

Ala Pro Lys Gly Cys Gly Pro Pro Ser Pro Cys Leu Tyr Asn Gly
            1130                1135                1140

Ser Cys Ser Glu Thr Thr Gly Leu Gly Gly Pro Gly Phe Arg Cys
            1145                1150                1155

Ser Cys Pro His Ser Ser Pro Gly Pro Arg Cys Gln Lys Pro Gly
            1160                1165                1170

Ala Lys Gly Cys Glu Gly Arg Ser Gly Asp Gly Ala Cys Asp Ala
            1175                1180                1185

Gly Cys Ser Gly Pro Gly Gly Asn Trp Asp Gly Gly Asp Cys Ser
            1190                1195                1200

Leu Gly Val Pro Asp Pro Trp Lys Gly Cys Pro Ser His Ser Arg
            1205                1210                1215

Cys Trp Leu Leu Phe Arg Asp Gly Gln Cys His Pro Gln Cys Asp
            1220                1225                1230

Ser Glu Glu Cys Leu Phe Asp Gly Tyr Asp Cys Glu Thr Pro Pro
            1235                1240                1245

Ala Cys Thr Pro Ala Tyr Asp Gln Tyr Cys His Asp His Phe His
            1250                1255                1260

Asn Gly His Cys Glu Lys Gly Cys Asn Thr Ala Glu Cys Gly Trp
            1265                1270                1275

Asp Gly Gly Asp Cys Arg Pro Glu Asp Gly Asp Pro Glu Trp Gly
            1280                1285                1290

Pro Ser Leu Ala Leu Leu Val Val Leu Ser Pro Pro Ala Leu Asp
            1295                1300                1305
```

-continued

```
Gln Gln Leu Phe Ala Leu Ala Arg Val Leu Ser Leu Thr Leu Arg
    1310                1315                1320

Val Gly Leu Trp Val Arg Lys Asp Arg Asp Gly Arg Asp Met Val
    1325                1330                1335

Tyr Pro Tyr Pro Gly Ala Arg Ala Glu Glu Lys Leu Gly Gly Thr
    1340                1345                1350

Arg Asp Pro Thr Tyr Gln Glu Arg Ala Ala Pro Gln Thr Gln Pro
    1355                1360                1365

Leu Gly Lys Glu Thr Asp Ser Leu Ser Ala Gly Phe Val Val Val
    1370                1375                1380

Met Gly Val Asp Leu Ser Arg Cys Gly Pro Asp His Pro Ala Ser
    1385                1390                1395

Arg Cys Pro Trp Asp Pro Gly Leu Leu Leu Arg Phe Leu Ala Ala
    1400                1405                1410

Met Ala Ala Val Gly Ala Leu Glu Pro Leu Leu Pro Gly Pro Leu
    1415                1420                1425

Leu Ala Val His Pro His Ala Gly Thr Ala Pro Pro Ala Asn Gln
    1430                1435                1440

Leu Pro Trp Pro Val Leu Cys Ser Pro Val Ala Gly Val Ile Leu
    1445                1450                1455

Leu Ala Leu Gly Ala Leu Leu Val Leu Gln Leu Ile Arg Arg Arg
    1460                1465                1470

Arg Arg Glu His Gly Ala Leu Trp Leu Pro Pro Gly Phe Thr Arg
    1475                1480                1485

Arg Pro Arg Thr Gln Ser Ala Pro His Arg Arg Pro Pro Leu
    1490                1495                1500

Gly Glu Asp Ser Ile Gly Leu Lys Ala Leu Lys Pro Lys Ala Glu
    1505                1510                1515

Val Asp Glu Asp Gly Val Val Met Cys Ser Gly Pro Glu Glu Gly
    1520                1525                1530

Glu Glu Val Gly Gln Ala Glu Glu Thr Gly Pro Pro Ser Thr Cys
    1535                1540                1545

Gln Leu Trp Ser Leu Ser Gly Gly Cys Gly Ala Leu Pro Gln Ala
    1550                1555                1560

Ala Met Leu Thr Pro Pro Gln Glu Ser Glu Met Glu Ala Pro Asp
    1565                1570                1575

Leu Asp Thr Arg Gly Pro Asp Gly Val Thr Pro Leu Met Ser Ala
    1580                1585                1590

Val Cys Cys Gly Glu Val Gln Ser Gly Thr Phe Gln Gly Ala Trp
    1595                1600                1605

Leu Gly Cys Pro Glu Pro Trp Glu Pro Leu Leu Asp Gly Gly Ala
    1610                1615                1620

Cys Pro Gln Ala His Thr Val Gly Thr Gly Glu Thr Pro Leu His
    1625                1630                1635

Leu Ala Ala Arg Phe Ser Arg Pro Thr Ala Ala Arg Arg Leu Leu
    1640                1645                1650

Glu Ala Gly Ala Asn Pro Asn Gln Pro Asp Arg Ala Gly Arg Thr
    1655                1660                1665

Pro Leu His Ala Ala Val Ala Ala Asp Ala Arg Glu Val Cys Gln
    1670                1675                1680

Leu Leu Leu Arg Ser Arg Gln Thr Ala Val Asp Ala Arg Thr Glu
    1685                1690                1695
```

-continued

Asp Gly Thr Thr Pro Leu Met Leu Ala Ala Arg Leu Ala Val Glu
1700                1705                1710

Asp Leu Val Glu Glu Leu Ile Ala Ala Gln Ala Asp Val Gly Ala
1715                1720                1725

Arg Asp Lys Trp Gly Lys Thr Ala Leu His Trp Ala Ala Val
1730                1735                1740

Asn Asn Ala Arg Ala Ala Arg Ser Leu Leu Gln Ala Gly Ala Asp
1745                1750                1755

Lys Asp Ala Gln Asp Asn Arg Glu Gln Thr Pro Leu Phe Leu Ala
1760                1765                1770

Ala Arg Glu Gly Ala Val Glu Val Ala Gln Leu Leu Leu Gly Leu
1775                1780                1785

Gly Ala Ala Arg Glu Leu Arg Asp Gln Ala Gly Leu Ala Pro Ala
1790                1795                1800

Asp Val Ala His Gln Arg Asn His Trp Asp Leu Leu Thr Leu Leu
1805                1810                1815

Glu Gly Ala Gly Pro Pro Glu Ala Arg His Lys Ala Thr Pro Gly
1820                1825                1830

Arg Glu Ala Gly Pro Phe Pro Arg Ala Arg Thr Val Ser Val Ser
1835                1840                1845

Val Pro Pro His Gly Gly Gly Ala Leu Pro Arg Cys Arg Thr Leu
1850                1855                1860

Ser Ala Gly Ala Gly Pro Arg Gly Gly Gly Ala Cys Leu Gln Ala
1865                1870                1875

Arg Thr Trp Ser Val Asp Leu Ala Ala Arg Gly Gly Gly Ala Tyr
1880                1885                1890

Ser His Cys Arg Ser Leu Ser Gly Val Gly Ala Gly Gly Gly Pro
1895                1900                1905

Thr Pro Arg Gly Arg Arg Phe Ser Ala Gly Met Arg Gly Pro Arg
1910                1915                1920

Pro Asn Pro Ala Ile Met Arg Gly Arg Tyr Gly Val Ala Ala Gly
1925                1930                1935

Arg Gly Gly Arg Val Ser Thr Asp Asp Trp Pro Cys Asp Trp Val
1940                1945                1950

Ala Leu Gly Ala Cys Gly Ser Ala Ser Asn Ile Pro Ile Pro Pro
1955                1960                1965

Pro Cys Leu Thr Pro Ser Pro Glu Arg Gly Ser Pro Gln Leu Asp
1970                1975                1980

Cys Gly Pro Pro Ala Leu Gln Glu Met Pro Ile Asn Gln Gly Gly
1985                1990                1995

Glu Gly Lys Lys
   2000

<210> SEQ ID NO 42
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atgggtccag gtgcaagagg tagaaggcgt agaaggagac caatgagccc acctcctccg        60
ccacctccag tgagagcact gcctttgctg ttgctgctgg ctggacctgg tgcagcagct       120
cctccttgcc tggac                                                         135

```
<210> SEQ ID NO 43
<211> LENGTH: 135
<212> TYPE: DNA
<213> ORGANISM: Homo sapiens

<400> SEQUENCE: 43
atggggccgg gggcccgtgg ccgccgccgc cgccgtcgcc cgatgtcgcc gccaccgcca         60
ccgccacccg tgcgggcgct gccoctgctg ctgctgctag cggggccggg ggctgcagcc       120
cccccttgcc tggac                                                        135

<210> SEQ ID NO 44
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Gly Pro Gly Ala Arg Gly Arg Arg Arg Arg Arg Pro Met Ser
1               5                   10                  15

Pro Pro Pro Pro Pro Pro Pro Val Arg Ala Leu Pro Leu Leu Leu Leu
            20                  25                  30

Leu Ala Gly Pro Gly Ala Ala Ala Pro Pro Cys Leu Asp
        35                  40                  45
```